US012747295B2

(12) United States Patent
Garnache-Ottou et al.

(10) Patent No.: US 12,747,295 B2
(45) Date of Patent: Sep. 29, 2026

(54) ANTI-CD123 ANTIBODIES, ANTI-CD123 CHIMERIC ANTIGEN RECEPTORS AND ANTI-CD123 CHIMERIC ANTIGEN RECEPTORS T CELLS

(71) Applicants: UNIVERSITE DE FRANCHE-COMTE, Besançon Cedex (FR); INSTITUT NATIONAL DE LA SANTE ET DE LA RECHERCHE MEDICALE, Paris Cedex (FR); ETABLISSEMENT FRANÇAIS DU SANG, La Plaine Saint Denis Cedex (FR); CENTRE HOSPITALIER REGIONAL UNIVERSITAIRE DE BESANÇON, Besançon Cedex (FR)

(72) Inventors: Francine Garnache-Ottou, Besançon (FR); Christophe Ferrand, La Plaine Saint Denis (FR); Fanny Angelot-Delettre, La Plaine Saint Denis (FR); Marina Deschamps, La Plaine Saint Denis (FR); Elodie Bole-Richard, Paris (FR); Olivier Adotevi, Besançon (FR)

(73) Assignees: UNIVERSITE DE FRANCHE-COMTE, Besançon Cedex (FR); INSTITUT NATIONAL DE LA SANTE ET DE LA RECHERCHE MEDICALE, Paris Cedex (FR); ETABLISSEMENT FRANÇAIS DU SANG, La Plaine Saint Denis Cedex (FR); CENTRE HOSPITALIER REGIONAL UNIVERSITAIRE DE BESANÇON, Besançon Cedex (FR)

( * ) Notice: Subject to any disclaimer, the term of this patent is extended or adjusted under 35 U.S.C. 154(b) by 1257 days.

(21) Appl. No.: 17/621,504

(22) PCT Filed: Jun. 22, 2020

(86) PCT No.: PCT/EP2020/067303
§ 371 (c)(1),
(2) Date: Dec. 21, 2021

(87) PCT Pub. No.: WO2020/254682
PCT Pub. Date: Dec. 24, 2020

(65) Prior Publication Data
US 2022/0348668 A1 Nov. 3, 2022

(30) Foreign Application Priority Data
Jun. 21, 2019 (EP) .................................... 19305816

(51) Int. Cl.
*C07K 16/28* (2006.01)
*A61K 38/17* (2006.01)
*A61P 35/00* (2006.01)
*C12N 15/63* (2006.01)

(52) U.S. Cl.
CPC ...... *C07K 16/2866* (2013.01); *A61K 38/1793* (2013.01); *A61P 35/00* (2018.01); *C12N 15/63* (2013.01); *C12N 2510/00* (2013.01)

(58) Field of Classification Search
None
See application file for complete search history.

(56) References Cited

U.S. PATENT DOCUMENTS

2022/0281997 A1* 9/2022 Qin .................... G01N 33/6854

FOREIGN PATENT DOCUMENTS

| | | | |
|---|---|---|---|
| CN | 108409840 | A | 8/2018 |
| WO | 2018/057802 | A1 | 3/2018 |
| WO | 2019/018538 | A1 | 1/2019 |
| WO | 2019/072824 | A1 | 4/2019 |

OTHER PUBLICATIONS

Cai (Blood, vol. 130, Suppl. 1, Abstract/Poster 2625, 2017) (Year: 2017).*
Harris (Biotechnology, vol. 11, p. 1293-1297, 1993) (Year: 1993).*
Johnson and Wu (Methods in Molecular Biology, Antibody Engineering: Methods and Protocols, vol. 248, p. 11-25, 2004) (Year: 2004).*
Dubel (Handbook of Therapeutic Antibodies, 2007, p. 100-101) (Year: 2007).*
Rudikoff et al. (Proceedings of the National Academy of Sciences USA, vol. 79, p. 1979-1983, 1982) (Year: 1982).*
Bendig M. M. (Methods: A Companion to Methods in Enzymology, 1995; 8:83-93) (Year: 1995).*
(Continued)

*Primary Examiner* — Julie Wu
(74) *Attorney, Agent, or Firm* — Volpe Koenig

(57) ABSTRACT

The invention is relative to monoclonal anti-CD123 antibodies, or fragments thereof that specifically bind to the alpha chain of the human interleukin 3 (IL3) receptor. Further, the invention is relative to an isolated nucleic acid molecule encoding a chimeric antigen receptor (CAR), wherein the CAR comprises an antibody or an antibody fragment which includes an anti-CD123 binding domain, a transmembrane domain, and an intracellular signaling domain comprising at least a stimulatory domain, polypeptides encoded by said nucleic acid molecule as well as an isolated chimeric antigen receptor (CAR) molecules comprising such an antibody or antibody fragment. The invention is also relative to a vector comprising a nucleic acid molecule encoding a CAR, as well as a T cell CN comprising said vector, and to the use of a T cell expressing a CAR molecule for a treatment of a proliferative disease in a mammal, such as cancer.

11 Claims, 24 Drawing Sheets

Specification includes a Sequence Listing.

(56) References Cited

OTHER PUBLICATIONS

Paul, Fundamental Immunology, 3rd Edition, 1993, pp. 292-295 (Year: 1993).*

Cai, T. et al. "Pre-clinical Studies of Allogeneic Anti-CD123 CAR-T Cells for the Treatment of Blastic plasmacytoid dendritic cell neoplasm (BPDCN)" (2016) Cellectis.

Cai, T. et al. "Pre-Clinical Studies of Anti-CD123 CAR-T Cells for the Treatment of Blastic Plasmacytoid Dendritic Cell Neoplasm (BPDCN)" (2016) Blood 128(22): 4039.

Khoury, J. D. "Blastic Plasmacytoid Dendritic Cell Neoplasm" (2018) Current Hematologic Malignancy Reports 13(6): 477-483.

Sorrento Therapeutics "Sorrento's TNK Therapeutics Provides Progress Update for its Anti-CD38 and CD123 CAR-T Programs for Treatment of Hematological Malignancies" (2016).

Stevens, B. M. et al. "CD123 CAR T cells for the treatment of myelodysplastic syndrome" (2019) Experimental Hematology 74(1): 52-63.

Xu, J. L. and Davis, M. M. "Diversity in the CDR3 region of VH is sufficient for most antibody specificities" (2000) Immunity 13: 37-45.

Office Action issued in corresponding Japanese Patent Application No. 2021-576366 on Jul. 23, 2024, consisting of 5 pp. (English Translation Provided).

* cited by examiner

| MAb | HEAVY CHAIN | | | | | LIGHT CHAIN | | | |
|---|---|---|---|---|---|---|---|---|---|
| | VH | DH | JH | CDR1 | CDR1(AA) | VK | JK | CDR1 | CDR1(AA) |
| 18B4D5 | VH 3-2*02* | DH 3-1*01 | JH2*01 | ggctactcaatcacc.........agtgattatacc SEQ ID NO: 158 | GYSITSDYT SEQ ID NO: 25 | VK 4-74*01 | JK 1*01 | tcaagtataagt..............tccagttac SEQ ID NO: 170 | SSISSSY SEQ ID NO: 26 |
| 17F7B2 | VH 1-5*01* | DH 2-14*01 | JH 3*01 | ggctacagcttt.........accagctactgg SEQ ID NO: 159 | GYSFTSYW SEQ ID NO: 27 | VK 1-110*01 | JK 4*01 | cagagccttgtacacagt...aatggaatcacctat SEQ ID NO: 171 | QSLVHSNGITY SEQ ID NO: 28 |
| 11B6E6 | VH 2-9-2*01* | DH 1-2*01 | JH 4*01 | gggttctcatta.........accagctatgat SEQ ID NO: 160 | GFSLTSYD SEQ ID NO: 29 | VK 8-21*01 | JK 4*01 | cagagtctgctcaacagtagcacccgaaagaactact SEQ ID NO: 172 | QSLLNSSTRKNY SEQ ID NO: 30 |
| 14G12D7 | VH 3-2*02 | DH 1-1*02 | JH 2*01 | ggctactcagtcacc.........agtgattatgcc SEQ ID NO: 161 | GYSVTSDYA SEQ ID NO: 31 | VK 4-57-1*01 | JK 2*01 | tcaagtgtacgt..............tccagttac SEQ ID NO: 173 | SSVRSSY SEQ ID NO: 32 |
| 11A12C6 | VH 2-9*01 | DH 2-3*01 | JH 1*01 | gggttctcatta.........accagctatgat SEQ ID NO: 162 | GFSLTSYD SEQ ID NO: 33 | VK 8-21*01 | JK 4*01 | cagagtctgttcagcagtatgcccgaaagaactac SEQ ID NO: 174 | QSLFSSSARKNY SEQ ID NO: 34 |
| 15E11B7 | VH 1-20*01 | DH 2-14*01 | JH 3*01 | ggttactcattt.........actggctacttt SEQ ID NO: 163 | GYSFTGYF SEQ ID NO: 35 | VK 3-12*01 | JK 2*01 | aaaagtgtcagtaca......tctggctataattat SEQ ID NO: 175 | KSVSTSGYNY SEQ ID NO: 36 |

| MAb | HEAVY CHAIN | | | | | LIGHT CHAIN | | | |
|---|---|---|---|---|---|---|---|---|---|
| | VH | DH | JH | CDR2 | CDR2(AA) | VK | JK | CDR2 | CDR2(AA) |
| 18B4D5 | VH 3-2*02* | DH 3-1*01 | JH2*01 | ataagcttcagt.........ggtagcact SEQ ID NO: 152 | ISFSGST SEQ ID NO: 13 | VK 4-74*01 | JK 1*01 | agcaca.................. tcc | STS SEQ ID NO: 14 |
| 17F7B2 | VH 1-5*01* | DH 2-14*01 | JH 3*01 | ttttatcctgga......aaaagtgatact SEQ ID NO: 153 | FYPGKSDT SEQ ID NO: 15 | VK 1-110*01 | JK 4*01 | aaagtt.................. tcc | KVS SEQ ID NO: 16 |
| 11B6E6 | VH 2-9-2*01* | DH 1-2*01 | JH 4*01 | atatggactggt.........ggaggcaca SEQ ID NO: 154 | IWTGGGT SEQ ID NO: 17 | VK 8-21*01 | JK 4*01 | tgggca.................. tcc | WAS SEQ ID NO: 18 |
| 14G12D7 | VH 3-2*02 | DH 1-1*02 | JH 2*01 | ataatctacagt.........ggtaccact SEQ ID NO: 155 | IIYSGTT SEQ ID NO: 19 | VK 4-57-1*01 | JK 2*01 | agcaca.................. tcc | STS SEQ ID NO: 20 |
| 11A12C6 | VH 2-9*01 | DH 2-3*01 | JH 1*01 | atatggactggt.........ggaggcaca SEQ ID NO: 156 | IWTGGGT SEQ ID NO: 21 | VK 8-21*01 | JK 4*01 | tgggca.................. tcc | WAS SEQ ID NO: 22 |
| 15E11B7 | VH 1-20*01 | DH 2-14*01 | JH 3*01 | attaatccttac......aatgattatact SEQ ID NO: 157 | INPYNDYT SEQ ID NO: 23 | VK 3-12*01 | JK 2*01 | cttgca.................. tcc | LAS SEQ ID NO: 24 |

| MAb | HEAVY CHAIN | | | | | LIGHT CHAIN | | | |
|---|---|---|---|---|---|---|---|---|---|
| | VH | DH | JH | CDR3 (nt) VH ... n DH n ... JH | CDR3(AA) | VK | JK | CDR3 (nt) VK ... JK | CDR3(AA) |
| 18B4D5 | VH 3-2*02* | DH 3-1*01 | JH2*01 | gcaaga ... gggct c ... gactac SEQ ID NO: 146 | ARGLDY SEQ ID NO: 1 | VK 4-74*01 | JK 1*01 | caccagttgcatcgttcccc ... gtggacg SEQ ID NO: 164 | HQLHRSPWT SEQ ID NO: 2 |
| 17F7B2 | VH 1-5*01* | DH 2-14*01 | JH 3*01 | acaa aggg ... ctataggtacga ... ctggtttgcttat SEQ ID NO: 147 | TKGYRYDWFAY SEQ ID NO: 3 | VK 1-110*01 | JK 4*01 | tctcaaaatacacatgttcc ... attcacg SEQ ID NO: 165 | SQNTHVPFT SEQ ID NO: 4 |
| 11B6E6 | VH 2-9-2*01* | DH 1-2*01 | JH 4*01 | gtgagag ... ctc acggct ... attactttgctatggactac SEQ ID NO: 148 | VRAHGYYFAMDY SEQ ID NO: 5 | VK 8-21*01 | JK 4*01 | aagcaatcttataatct ... attcacg SEQ ID NO: 166 | KQSYNLFT SEQ ID NO: 6 |
| 14G12D7 | VH 3-2*02 | DH 1-1*02 | JH 2*01 | acaag ... ggggg ... ttgactac SEQ ID NO: 149 | TRGVDY SEQ ID NO: 7 | VK 4-57-1*01 | JK 2*01 | ctgcagttcagtggttacccgttcac ... g SEQ ID NO: 167 | LQFSGYPFT SEQ ID NO: 8 |
| 11A12C6 | VH 2-9*01 | DH 2-3*01 | JH 1*01 | gtaagag g ... tgatggtta ... ctactggtacttcgatgtc SEQ ID NO: 150 | VRGDGYYWYFDV SEQ ID NO: 9 | VK 8-21*01 | JK 4*01 | aagcaatcttatagtct ... attcacg SEQ ID NO: 168 | KQSYSLFT SEQ ID NO: 10 |
| 15E11B7 | VH 1-20*01 | DH 2-14*01 | JH 3*01 | g gaggggg ... ggtacga gggg ... cctggtttgcttc SEQ ID NO: 151 | GGGVRGAWFAF SEQ ID NO: 11 | VK 3-12*01 | JK 2*01 | cagcacagtgcggatcttcct ... tacacg SEQ ID NO: 169 | QHSADLPYT SEQ ID NO: 12 |

FIG. 1

FIG. 2

| MAb | HEAVY CHAIN | |
|---|---|---|
| | FR1 | FR1(AA) |
| 18B4D5 | gaggtcaagctgcaggagtcaggacct...ggcctggtgaaaccttctcagtctctgtccctcacctgcactgtcact SEQ ID NO: 98 | EVKLQESGP.GLVKPSQSLSLTCTVT SEQ ID NO: 37 |
| 17F7B2 | gaggttcagctccagcagtctgggact...gtgctggcaaggcctggggcttccgtgaagatgtcctgaaggcttct SEQ ID NO: 99 | EVQLQQSGT.VLARPGASVKMSCKAS SEQ ID NO: 41 |
| 11B6E6 | caggtcaagctggaggagtcaggacct...ggcctggtggcgccctcacagagcctgtccattacctgcactgtctct SEQ ID NO: 100 | QVKLEESGP.GLVAPSQSLSITVTVS SEQ ID NO: 45 |
| 14G12D7 | gaggttcagctgcaggagtctggacct...ggcctggtgaaaccttctcagtctctgtccctcacctgcactgtcact SEQ ID NO: 101 | EVQLQESGP.GLVKPSQSLSLTCTVT SEQ ID NO: 49 |
| 11A12C6 | caggtgcagctgaaggagtcaggacct...ggcctggtggcgccctcacagagcctgtccattacctgcactgtctct SEQ ID NO: 102 | QVQLKESGP.GLVAPSQSLSITCTVS SEQ ID NO: 53 |
| 15E11B7 | gaggttcagctggagcagtctggacct...gagctggtgaagcctggggattcagtgaagatatcctgcaaggcttct SEQ ID NO: 103 | EVQLEQSGPELVKPGDSVKISCKAS SEQ ID NO: 57 |

| MAb | HEAVY CHAIN | |
|---|---|---|
| | FR2 | FR2(AA) |
| 18B4D5 | tggaactggatccggcagtttccaggaaacaaactggagtggatgggctac SEQ ID NO: 104 | WNWIRQFPGNKLEWMGY SEQ ID NO: 38 |
| 17F7B2 | atgcactgggtaaaacagaggcctgggcagggtctagaatggattggtgct SEQ ID NO: 105 | MHWVKQRPGQGLEWIGA SEQ ID NO: 42 |
| 11B6E6 | ataagctggattcgccagccaccaggaaagggtctggagtggctggagta SEQ ID NO: 106 | ISWIRQPPGKGLEWLGV SEQ ID NO: 46 |
| 14G12D7 | tggaactggatccggcagtttcccggaaacaaactggagtggatgggctac SEQ ID NO: 107 | WNWIRQFPGNKLEWMGY SEQ ID NO: 50 |
| 11A12C6 | ataaactggattcgccagacaccaggaaagggtctggagtggctggagta SEQ ID NO: 108 | INWIRQTPGKGLEWLGV SEQ ID NO: 54 |
| 15E11B7 | atgaac tgggtgaaacagagccatggaaagagccttgagtggattggacgt SEQ ID NO: 109 | MNWVKQSHGKSLEWIGR SEQ ID NO: 58 |

| MAb | HEAVY CHAIN | |
|---|---|---|
| | FR3 | FR3(AA) |
| 18B4D5 | agctacaacccatctctcaaa...agtcgactctctatcactcgagacacatccaagaaccagttcttcctgcagttgaattctgtgactactgaggacacagccacatattactgt SEQ ID NO: 110 | SYNPSLK.SRLSITRDTSKNQFFLQLNSVTTEDTATYYC SEQ ID NO: 39 |
| 17F7B2 | acctacaaccagaagttcaag...ggcaaggccaaactgactgccgtcacatccgccagtactgcctacatggagctcagcagcctgacaaatgaggactctgcggtctattactgt SEQ ID NO: 111 | TYNQKFK.GKAKLTAVTSASTAYMELSSLTNEDSAVYYC SEQ ID NO: 43 |
| 11B6E6 | aattataattcagctttcatg...tccagactgagcatcagcaaggacaactccaagagccaagttttcttaaaaatgttcagtctgcaaactgatgacacagccatatattactgt SEQ ID NO: 112 | NYNSAFM.SRLSISKDNSKSQVFLKMFSLQTDDTAIYYC SEQ ID NO: 47 |
| 14G12D7 | agctacaacccatctctcaaa...agtcgaatctctatcactcgagacacatccaagaaccagttcttcctgcagttgaattctgtgactactgaggacacagccacatattactgt SEQ ID NO: 113 | SYNPSKLK.SRISITRDTSKNQFFLQLNSVTTEDTATYYC SEQ ID NO: 51 |
| 11A12C6 | aattataattcagctttcatg...tccagactgagcatcagcagggacaactccaagagccaggttttcttaaaaatgaacagtctgcaaactgatgacacagccatatattactgt SEQ ID NO: 114 | NYNSAFM.SRLSISRDNSKSQVFLKMNSLQTDDTAIYYC SEQ ID NO: 55 |
| 15E11B7 | ttcaacaaccagaagttcaag...gacaaggccacattgactgtagacaaatcctcgagcacagcccacatggagctcctgagcctacatctgaggactctgcagtctattattgt SEQ ID NO: 115 | FNNQKFK.DKATLTVDKSSSTAHMELLSLTSEDSAVYYC SEQ ID NO: 59 |

| MAb | HEAVY CHAIN | |
|---|---|---|
| | FR3 | FR3(AA) |
| 18B4D5 | tggggccaaggcaccactctcacagtctcctcagccaaaacaacagcccccatcggtctatccactggcccctgtgtgtggagatacaactggctcctcggtgactctaggatgcctggtc SEQ ID NO: 116 | WGQGTTLTVSSAKTTAPSVYPLAPVCGDTTGSSVTLGCLVKS SEQ ID NO: 40 |
| 17F7B2 | tggggccaagggactctggtcactgtctctgcagccaaaacgacacccccatctgtctattcca SEQ ID NO: 117 | WGQGTLVTVSAAKTTPPSVYS SEQ ID NO: 44 |
| 11B6E6 | tggggtcaaggaacctcagtcaccgtctcctcagccaaaacaacagcccccatcggtctatccactggcccctgtgtgtggagatacaactggctcctcggtgactcaggatgcctggtcaagtcc SEQ ID NO: 118 | WGQGTSVTVSSAKTTAPSVYPLAPVCGDTTGSSVTLGCLVKS SEQ ID NO: 48 |
| 14G12D7 | tggggccaaggcaccactctcacagtctcctcagccaaaacgacacccccatctgtctattcca SEQ ID NO: 119 | WGQGTTLTVSSAKTTPPSVYS SEQ ID NO: 52 |
| 11A12C6 | tggggcgcagggaccacggtcacagtctcctcagccaaaacgacacccccatctgtctattcca SEQ ID NO: 120 | WGAGTTVTVSSAKTTPPSVYS SEQ ID NO: 56 |
| 15E11B7 | tggggccaagggactctggtcactgtctctgaagccaaaacaacagcccccatcggtctatccactggcccctgtgtgtggagatacaactggctcctcggtgactctaggatgcctggtcaagtcca SEQ ID NO: 121 | WGQGTLVYVSEAKTTAPSVYPLAPVCGDTTGSSVTLGCLVKS SEQ ID NO: 60 |

FIG.3

| MAb | LIGHT CHAIN FR1 | LIGHT CHAIN FR1(AA) |
|---|---|---|
| 18B4D5 | gatattgtgatgacacagtctccagcaatcatgtctgcatctcttggggaacgggtcaccatgacctgcactgccagc SEQ ID NO: 122 | DIVMTQSPAIMSASLGERVTMTCTAS SEQ ID NO: 61 |
| 17F7B2 | gatgttgtgatgacccaaactccactctccctgcctgtcagtcttggagatcaagcctccatctcttgcagatctagt SEQ ID NO: 123 | DVVMTQTPLSLPVSLGDQASISCRSS SEQ ID NO: 65 |
| 11B6E6 | gatattgtgctgacacagtctccatcctccctggctgtgtcagcaggagagaaggtcactatgaggtgcaaatccagt SEQ ID NO: 124 | DIVLTQSPSSLAVSAGEKVTMRCKSS SEQ ID NO: 69 |
| 14G12D7 | gaaattgtgatcacccagtctccagcaatcatgtctgcatctccaggggaaaaggtcaccatgacctgcagggccagc SEQ ID NO: 125 | EIVITQSPAIMSASPGEKVTMTCRAS SEQ ID NO: 73 |
| 11A12C6 | gatattgtgatgacacagtctccatcctccctggctgtgcagcaggagagaaggtcactatgagctgcaaatccagt SEQ ID NO: 126 | DIVMTQSPSSLAVSAGEKVTMSCKSS SEQ ID NO: 77 |
| 15E11B7 | gatattgtgctgacacagtctacaacttccttagctgtgtctctgggccacgagggccaccatctcatgcagggccagc SEQ ID NO: 127 | DIVLTQSTTSLAVSLGQRATISCRAS SEQ ID NO: 81 |

| MAb | LIGHT CHAIN FR2 | LIGHT CHAIN FR2(AA) |
|---|---|---|
| 18B4D5 | ttgtactggtaccagcagaagccaggatcctcccccaaactctggatttat SEQ ID NO: 128 | LYWYQQKPGSSPKLWIY SEQ ID NO: 62 |
| 17F7B2 | ttacattggtacctgcagaagccaggccagtctccaaagctcctgatctac SEQ ID NO: 129 | LHWYLQKPGQSPKLLIY SEQ ID NO: 66 |
| 11B6E6 | ttggcttggtaccagcagaaaccagggcagtctcctaaactgctgatctac SEQ ID NO: 130 | LAWYQQKPGQSPKLLIY SEQ ID NO: 70 |
| 14G12D7 | ttgcactggtaccagcagaagtcaggtgcctcccccaaactctggatttat SEQ ID NO: 131 | LHWYQQKSGASPKLWIY SEQ ID NO: 74 |
| 11A12C6 | ttggcttggtaccagcagagaccagggcagtctcctaaactgctgatctac SEQ ID NO: 132 | LAWYQQRPGQSPKLLIY SEQ ID NO: 78 |
| 15E11B7 | atgcactggtaccaacagaaaccaggacagccacccaaactcctcatctat SEQ ID NO: 133 | MHWYQQKPGQPPKLLIY SEQ ID NO: 82 |

| MAb | LIGHT CHAIN FR3 | LIGHT CHAIN FR3(AA) |
|---|---|---|
| 18B4D5 | aacctggcttctggagtccca...gctcgcttcagtggcagtggg......tctgggacctcttactctctcacaatcagcagcatggaggctgaagatgctgccacttattactgc SEQ ID NO: 134 | NLASGVP.ARFSGSG..SGTSYSLTISSMEAEDAATYYC SEQ ID NO: 63 |
| 17F7B2 | aaccgattttctggggtccca...gacaggttcagtggcagtgga......tctgggacagatttcacactcaagatcagcagagtggaggctgaggatctgggagtttatttctgc SEQ ID NO: 135 | NRFSGVP.DRFSGSG..SGTDFTLKISRVEAEDLGVYFC SEQ ID NO: 67 |
| 11B6E6 | actaggggaatctggggtccct...gatcgcttcacaggcagtgga......tctgggacagatttcactctcaccatcagcagtgtgcaggctgaagacctggcagtttattactgc SEQ ID NO: 136 | TRESGVP.DRFTGSG..SGTDFTLTISSVQAEDLAVYYC SEQ ID NO: 71 |
| 14G12D7 | aacttggcttctggagtccct...gctcgcttcagtggcagtggg......tctgggacctcttactctctcacaatcagcagtgtggaggctgaagatgctgccacttattactgc SEQ ID NO: 137 | NLASGVP.ARFSGSG..SGTSYSLTISSVEAEDAATYYC SEQ ID NO: 75 |
| 11A12C6 | accaggggaatctggggtccct...gatcgcttcacaggcagtgga ......tctgggacagatttcactctcaccatcggcagtgtcaggctgaagacctggcagtttattactgc SEQ ID NO: 138 | TRESGVP.DRFTGSG..SGTDFTLTIGSVQAEDLAVYYC SEQ ID NO: 79 |
| 15E11B7 | aacctcgaatctggggtccct...gccaggttcagtggcagtggg ......tctgggacagacttcaccctcaacatccatcctgtggaggaggaggatgctgcaacctattactgt SEQ ID NO: 139 | NLESGVP.ARFSGSG..SGTDFTLNIHPVEEEDAATYYC SEQ ID NO: 83 |

| MAb | LIGHT CHAIN FR4 | LIGHT CHAIN FR4(AA) |
|---|---|---|
| 18B4D5 | ttcggtggaggcaccaagctggaaatcaaacgggctgatgctgcaccaactgtatccacc SEQ ID NO: 140 | FGGGTKLEIKRADAAPTVST SEQ ID NO: 64 |
| 17F7B2 | ttcggctcggggacaaagttggaaataaaacgggctgatgctgcaccaactgtatccacc SEQ ID NO: 141 | FGSGTKLEIKRADAAPTVST SEQ ID NO: 68 |
| 11B6E6 | ttcggctcggggacaaagttggaaataaaacgggctgatgctgcaccaactgtatccacca SEQ ID NO: 142 | FGSGTKLEIKRADAAPTVST SEQ ID NO: 72 |
| 14G12D7 | ttcggagggggggaccaagctggaaataaaacgggctgatgctgcaccaactgtatccacc SEQ ID NO: 143 | FGGGTKLEIKRADAAPTVST SEQ ID NO: 76 |
| 11A12C6 | ttcggctcggggacaaagttggaaataaaacgggctgatgctgcaccaactgtatccacc SEQ ID NO: 144 | FGSGTKLEIKRADAAPTVST SEQ ID NO: 80 |
| 15E11B7 | ttcggagggggggaccaagctggaaataaaacgggctgatgctgcaccaactgtatccacc SEQ ID NO: 145 | FGGGTKLEIKRADAAPTVST SEQ ID NO: 84 |

LIGHT CHAIN 18B4D5

>CONSENSUS LIGHT CHAIN 18B4D5
DIVMTQSPAIMSASLGERVTMTCTASSSISSSYLYWYQQKPGSSPKLWIYSTSNLASGVPARFSGSGSGTSYSLTISSMEAEDAATYYCHQLHRSPWTFGGGTKLEIKRA
DAAPTVST SEQ ID NO: 86

FIG.4

HEAVY CHAIN 18B4D5

>CONSENSUS HEAVY CHAIN 18B4D5
EVKLQESGPGLVKPSQSLSLTCTVTGYSITSDYTWNWIRQRPGNKLEWMGYISFSGSTSYNPSLKSRLSITRDTSKNQFFLQLNSVTTEDTATYYCARGLDYWGQGTTLT
VSSAKTTAPSVYPLAPVCGDTTGSSVTLGCLVKS SEQ ID NO: 85

FIG.5

LIGHT CHAIN 17F7B2

>CONSENSUS LIGHT CHAIN 17F7B2
DVVMTQTPLSLPVSLGDQASISCRSSQSLVHSNGITYLHWYLQKPGQSPKLLIYKVSNRFSGVPDRFSGSGSGTDFTLKISRVEAEDLGVYFCSQNTHVPFTFGSGTKLEI
KRADAAPTVST SEQ ID NO: 88

HEAVY CHAIN 17F7B2

>CONSENSUS HEAVY CHAIN 17F7B2
EVQLQQSGTVLARPGASVKMSCKASGYSFTSYWMHWVKQRPGQGLEWIGAFYPGKSDTTYNQKFKGKAKLTAVTSASTAYMELSSLTNEDSAVYYCTKGYRYDWF
AYWGQGTLVTVSAAKTTPPSVYS SEQ ID NO: 87

FIG.6

LIGHT CHAIN 11B6E6

>CONSENSUS LIGHT CHAIN 11B6E6
DIVLTQSPSSLAVSAGEKVTMRCKSSQSLLNSSTRKNYLAWYQQKPGQSPKLLIYWASTRESGVPDRFTGSGSGTDFTLTISSVQAEDLAVYYCKQSYNLFTFGSGTKLEI
KRADAAPTVST SEQ ID NO: 90

HEAVY CHAIN 11B6E6

>CONSENSUS HEAVY CHAIN 11B6E6
QVKLEESGPGLVAPSQSLSITCTVSGFSLTSYDISWIRQPPGKGLEWLGVIWTGGGTNYNSAFMSRLSISKDNSKSQVFLKMFSLQTDDTAIYYCVRAHGYYFAMDYW
GQGTSVTVSSAKTTAPSVYPLAPVCGDTTGSSVTLGCLVKS SEQ ID NO: 89

FIG.7

LIGHT CHAIN 14G12D7

>CONSENSUS LIGHT CHAIN 14G12D
DIVLTQSPAIMSASPGEKVTMTCRASSSVRSSYLHWYQQKSQGASPKLWIYSTSNLASGVPARFSGSGSGTSYSLTISSVEAEDAATYYCLQFSGYPFTFGGGTKLEIKRAD
AAPTVST SEQ ID NO: 92

HEAVY CHAIN 14G12D7

>CONSENSUS HEAVY CHAIN 14G12D7
EVQLQESGPGLVKPSQSLSLTCTVTGYSVTSDYAWNWIRQFPGNKLEWMGYIIYSGTTSYNPSLKSRISITRDTSKNQFFLQLNSVTTEDTATYYCTRGVDYWGQGTTL
TVSSAKTTPPSVYS SEQ ID NO: 91

FIG.8

LIGHT CHAIN 11A12C6

>CONSENSUS LIGHT CHAIN 11A12C6
DIVMTQSPSSLAVSAGEKVTMSCKSSQSLFSSSARKNYLAWYQQRPGQSPKLLIYWASTRESGVPDRFTGSGSGTDFTLTIGSVQAEDLAVYYCKQSYSLFTFGSGTKLE
IKRADAAPTVST SEQ ID NO: 94

HEAVY CHAIN 11A12C6

>CONSENSUS HEAVY CHAIN 11A12C6
QVQLKESGPGLVAPSQSLSITCTVSGFSLTSYDINWIRQTPGKGLEWLGVIWTGGGTNYNSAFMRSRLSISRDNSKSQVFLKMNSLQTDDTAIYYCVRGDGYYWYFDV
WGAGTTVTVSSAKTTPPSVYS SEQ ID NO: 93

LIGHT CHAIN 15E11B7

>CONSENSUS LIGHT CHAIN 15E11B7
DIVLTQSTTSLAVSLGQRATISCRASKSVSTSGYNYMHWYQQKPGQPPKLLIYLASNLESGVPARFSGSGSGTDFTLNIHPVEEEDAATYYCQHSADLPYTFGGGTKLEIK
RADAAPTVST SEQ ID NO: 96

HEAVY CHAIN 15E11B7

>CONSENSUS HEAVY CHAIN 15E11B7
EVQLEQSGPELVKPGDSVKISCKASGYSFTGYFMNWVKQSHGKSLEWIGRINPYNDYTFNNQKFKDKATLTVDKSSSTAHMELLSLTSEDSAVYYCGGGVRGAWFAF
WGQGTLVTVSEAKTTAPSVYPLAPVCGDTTGSSVTLGCLVKS SEQ ID NO: 95

FIG.9

| Hematopoietic cells | MFIR | n |
|---|---|---|
| BPDCN | 42.2 [36.5-46.6] | 3 |
| Lymphocytes | 2.2 [1-3.9] | 12 |
| Monocytes | 3.3 [1-5.8] | 12 |
| Polynuclear cells | 1.5 [1.2-2] | 5 |
| CD34 cells | 8 [5.2-11.1] | 7 |
| Normal pDC | 209.5 [63.4-361] | 7 |

FIG.13

CAR NUCLEIC ACID SEQUENCE

PEPTIDE SIGNAL TAG HA HEAVY CHAIN HINGE 1 LIGHT CHAIN HINGE 2 CD28 41BB CD3ζ

ATGAAACTGCCCGTGAGACTGCTGGTGCTGATGTTTTGGATTCCCGCTTCCTCGAGCGACCCATACGATGTTCCAGATTACGCCCCTGTCTGATGTGCAGCTTCAGGAGTCG
GGACCTGGCCTGGTGAAACCTTCTCAGTCTCTGTCCCTCACCTGCACTGTCACTGGCTACTCAATCACCAGTGATTATACCTGGAACTGGATTCGGCAGTTTCCAGGAAACAAAC
TGGAGTGGATGGGCTACATAAGCTTCAGTGGTAGCACTAGCTACAACCCATCTCTCAAAAGTCGACTCTCTATCACCCGAGACACATCCAAGAACCAGTTCTTCCTGCAGTTGA
ATTCTGTGACTACTGAGGACACAGCCACATATTACTGTGCAAGAGGGCTCGACTACTGGGGCCAAGGCACCACTCTCACAGTCTCCTCAGGAGGCGTTCAGGCGGAGGTGG
CTCTGGCGGTGGCGGATCGATAATGTCCAGAGGACAAATTGTTCTCACCCAGTCTCCAGCAATCATGTCTGCATCTCTTGGGGAACGGGTCACCATGACCTGCACTGCCAGCTC
AAGTATAAGTTCCAGTTACTTGTACTGGTACCAGCAGAAGCCAGGCTCCTCCCCCAAACTCTGGATTTATATGCACATCCAACCTGGCTTCTGGAGTCCCAGCTCGCTTCAGTGGC
AGTGGGTCTGGGACCTCTTACTCTCTCACAATCAGCAGCATGGAGGCTGAAGATGCTGCCACTTATTACTGCCACCAGTTGCATCGTTCCCCGTGGACGTTCGGTGGAGGCACC
AAGCTGGAAATCAAAGAGCCCAAATCTTGTGACAAAACTCACACATGCCCACCTGTCCCTGATCCCAAATTTTGGGTGCTGGTGGTGGTTGGTGGAGTCCTGGCTTGCTATAG
CTTGCTAGTAACAGTGGCCTTTATTATTTTCTGGGTGAGGAGTAAGAGGAGCAGGCTCCTGCACAGTGACTACATGAACATGACTCCCCGCCGCCCCGGGCCCACCCGCAAGC
ATTACCAGCCCTATGCCCCACCACGCGACTTCGCAGCCTATCGCTCCAAACGGGGCAGAAAGAAACTCCTGTATATATTCAAACAACCATTTATGAGACCAGTACAAACTACTCA
AGAGGAAGATGGCTGTAGCTGCCGATTTCCAGAAGAAGAAGAAGGAGGATGTGAACTGAGAGTGAAGTTCAGCAGGAGCGCAGACGCCCCCGCGTACCAGCAGGGCCAGA
ACCAGCTCTATAACGAGCTCAATCTAGGACGAAGAGAGGAGTACGATGTTTTGGACAAGAGGCGTGGCCGGGACCCTGAGATGGGGGGAAAGCCGAGAAGGAAGAACCCT
CAGGAAGGCCTGTACAATGAACTGCAGAAAGATAAGATGGCGGAGGCCTACAGTGAGATTGGGATGAAAGGCGAGCGCCGGAGGGGCAAGGGGCACGATGGCCTTTACCA
GGGTCTCAGTACAGCCACCAAGGACACCTACGACGCCCTTCACATGCAGGCCCTGCCCCCTCGC SEQ ID NO: 97

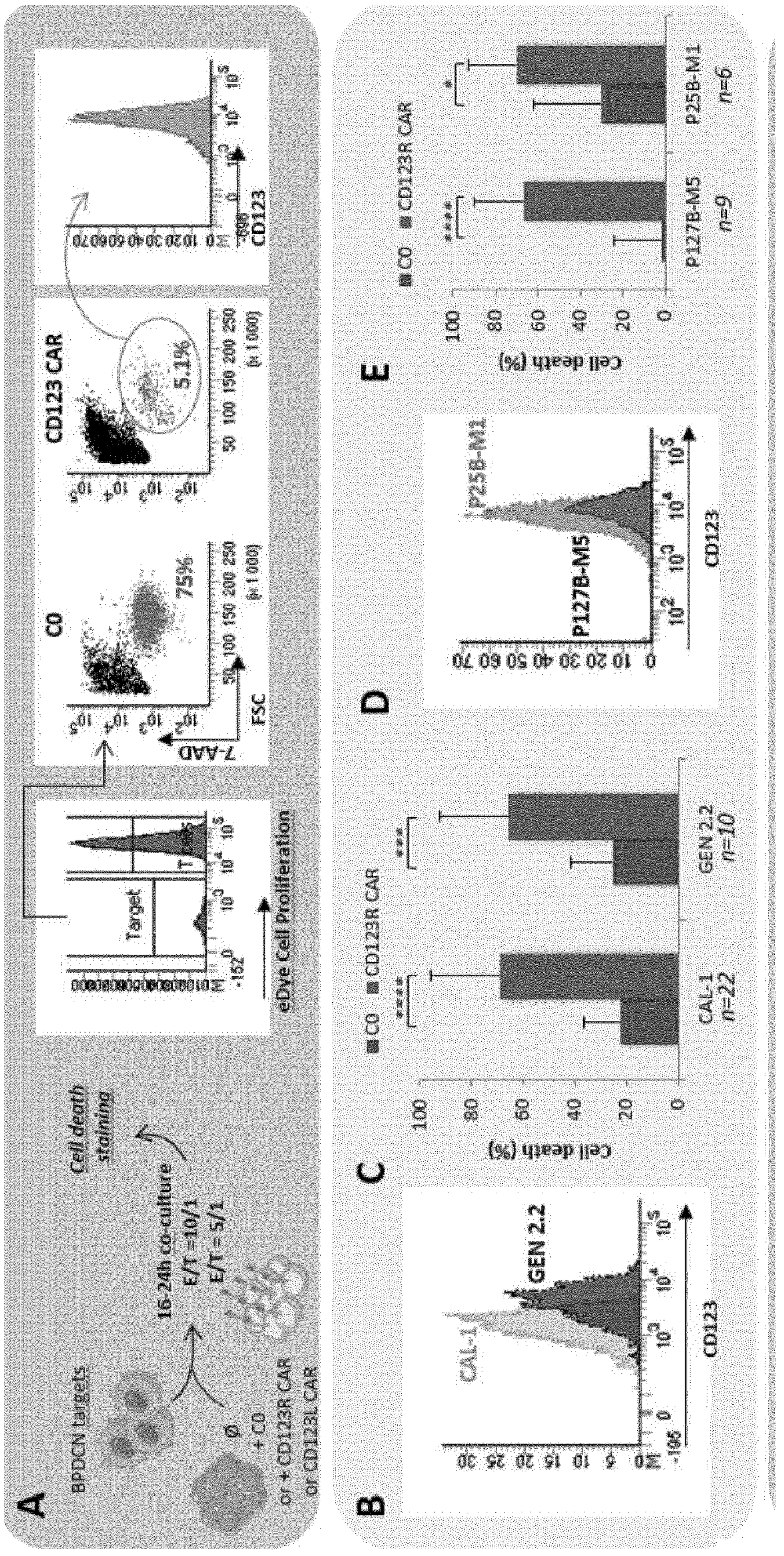
FIGURE 15 (...)

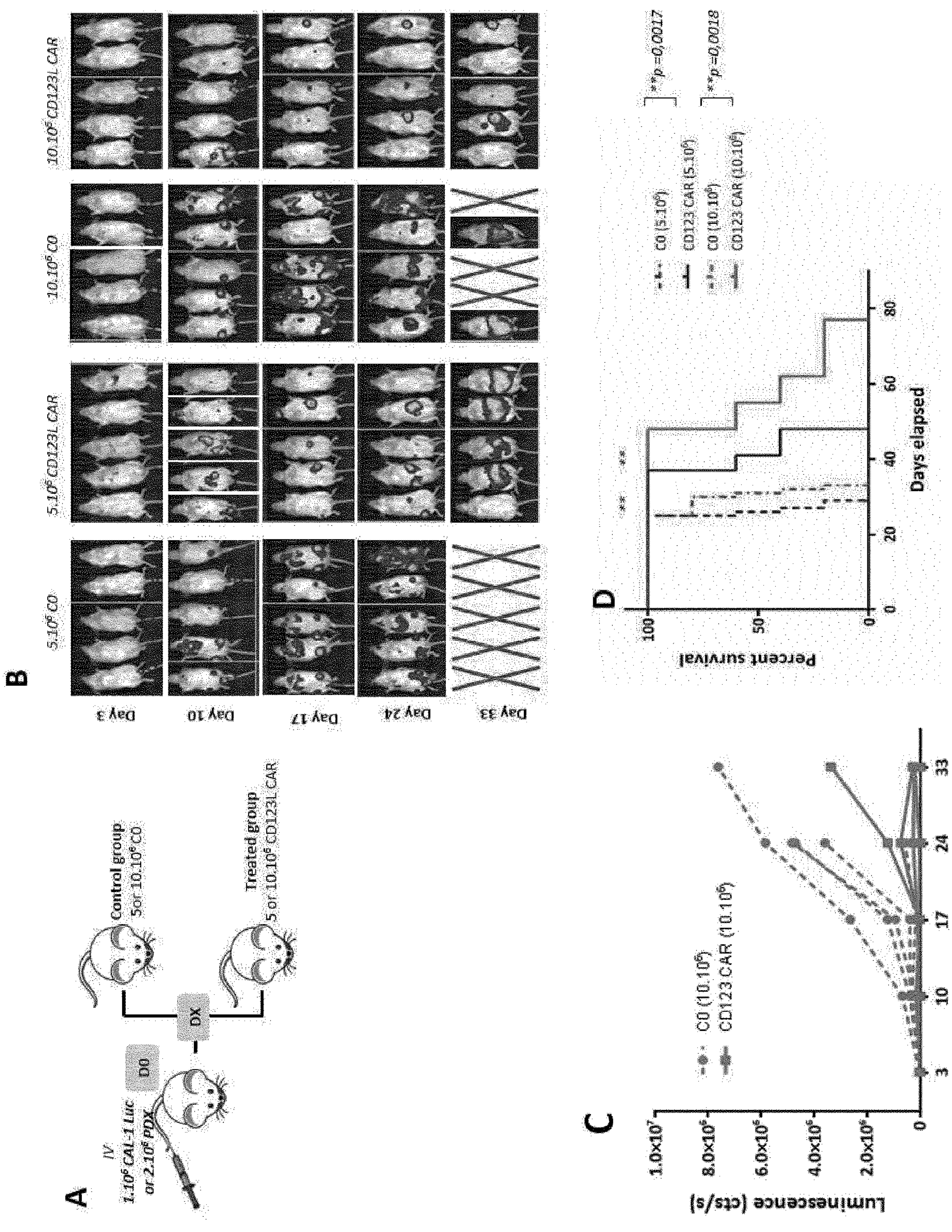
FIGURE 17 (...)

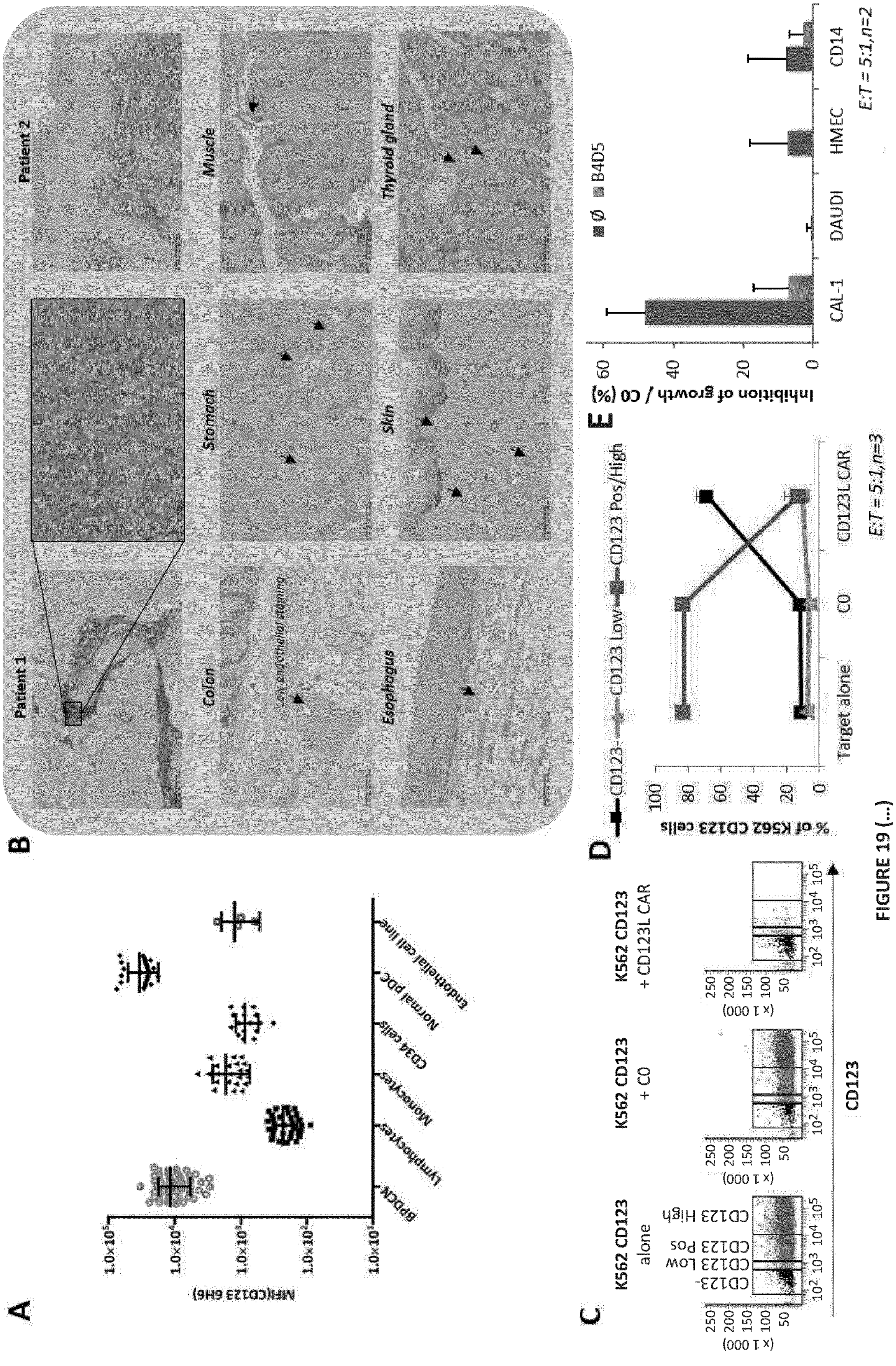
FIGURE 19 (...)

ANTI-CD123 ANTIBODIES, ANTI-CD123 CHIMERIC ANTIGEN RECEPTORS AND ANTI-CD123 CHIMERIC ANTIGEN RECEPTORS T CELLS

The present invention is relative to monoclonal antibodies and the use thereof. More particularly, the invention is relative to monoclonal anti-CD123 antibodies, or fragments thereof that specifically bind to the alpha chain of the human interleukin 3 (IL3) receptor.

The invention is further relative to an isolated nucleic acid molecule encoding a chimeric antigen receptor (CAR), wherein the CAR comprises an antibody or an antibody fragment which includes an anti-CD123 binding domain, a transmembrane domain, and an intracellular signaling domain comprising at least a stimulatory domain, polypeptides encoded by said nucleic acid molecule as well as an isolated chimeric antigen receptor (CAR) molecules comprising such an antibody or antibody fragment.

The present invention is also relative to a vector comprising a nucleic acid molecule encoding a CAR, as well as a T cell comprising said vector. The invention is also relative to the use of a T cell expressing a CAR molecule for a treatment of a proliferative disease in a mammal, such as cancer.

The fight against cancer is a worldwide challenge. Blastic Plasmacytoid Dendritic Cell Neoplasm (BPDCN) is a rare and aggressive cancer. It is a clonal disease derived from precursors of plasmacytoid dendritic cells (pDC) with prevalent skin lesions that invariably progresses to aggressive leukemic dissemination. The median overall survival (OS) of this type of cancer is ranging from 8 to 12 months.

BPDCN prognosis and treatment are both remarkably poor. Intensive chemotherapy is ineffective, since almost all patients undergoing this kind of treatment relapse after several weeks or months.

A lead for therapy is given by a fusion protein called SL-401, that consists of human interleukin 3 (IL3) fused to diphtheria toxin, cf. Angelot-Delettre F, Roggy A, Frankel A E, Lamarthee B, Seilles E, Biichle S, et al., In vivo and in vitro sensitivity of blastic plasmacytoid dendritic cell neoplasm to SL-401, an interleukin-3 receptor targeted biologic agent, Haematologica, 2015, 100(2):223-30.

The present invention improves the situation.

The Applicant has discovered that a protein called CD123—which is the alpha (a) chain of interleukin-3 (IL3) receptor—is overexpressed in cancer cells of all patients with BDPCN, cf. Garnache-Ottou F, Feuillard J, Ferrand C, Biichle S, Trimoreau F, Seilles E, et al., Extended diagnostic criteria for plasmacytoid dendritic cell leukaemia, British journal of haematology, 2009, 145(5):624-36.

As a consequence, the present invention focuses on using CD123 as therapeutic target.

In this context and with an objective to develop a biotherapy aiming CD123, the Applicant has succeeded in generating, developing, screening and selecting anti-CD123 monoclonal antibodies (MA) that specifically bind to human CD123. These antibodies may be used in therapy in general, and more specifically as a weapon against plasmacytoid dendritic cells neoplasm type leukemia and other pathologies expressing CD123.

A rapidly evolving technique in the fight of cancer uses engineered T cells (or T lymphocytes). These T cells comprise so called Chimeric Antigen Receptors, commonly referred to as CAR, that are specifically directed against a target antigen expressed by cancer cells.

With this in mind, the Applicant overcame many hurdles to use the newly developed anti-CD123 antibodies to genetically engineer T cells to express a CAR that specifically targets CD123, in order to specifically and efficiently fight cancer cells.

This new therapeutic weapon can be applied to BPDCN patients or patients who have relapsed of BPDCN, as well as to BPDCN patients that have been treated with intensive chemotherapy, with SL-401, hematopoietic stem cell allograft or other treatment methods.

To that end, in a first aspect the present invention features an antibody that binds specifically to antigen CD123, having a $K_D$ value of not more than $9.5\times10^{-9}$ M, an antibody dissociation rate $k_{off}$ of not more than $9.0\times10^{-4}$ $s^{-1}$, and an antibody association rate $k_{on}$ of at least $7\times10^{4}$ $Ms^{-1}$, and wherein said antibody is selected from the group consisting of AB1, AB2, AB3, AB4, AB5 and AB6, wherein AB1 comprises a heavy chain having and a light chain, and wherein the heavy chain comprises a complementary determining region 1 (CDR1) having at least 85% identity to amino acid sequence SEQ ID NO: 25, a complementary determining region 2 (CDR2) having at least 85% identity to amino acid sequence SEQ ID NO: 13, and a complementary determining region 3 (CDR3) having at least 85% identity to amino acid sequence SEQ ID NO: 1, and wherein the light chain comprises a complementary determining region 1 (CDR1) having at least 85% identity to amino acid sequence SEQ ID NO: 26, a complementary determining region 2 (CDR2) having at least 85% identity to amino acid sequence SEQ ID NO: 14, and a complementary determining region 3 (CDR3) having at least 85% identity to amino acid sequence SEQ ID NO: 2;

AB2 comprises a heavy chain and a light chain, and wherein the heavy chain comprises a complementary determining region 1 (CDR1) having at least 85% identity to amino acid sequence SEQ ID NO: 27, a complementary determining region 2 (CDR2) having at least 85% identity to amino acid sequence SEQ ID NO: 15, and a complementary determining region 3 (CDR3) having at least 85% identity to amino acid sequence SEQ ID NO: 3, and wherein the light chain comprises a complementary determining region 1 (CDR1) having at least 85% identity to amino acid sequence SEQ ID NO: 28, a complementary determining region 2 (CDR2) having at least 85% identity to amino acid sequence SEQ ID NO: 16, and a complementary determining region 3 (CDR3) having at least 85% identity to amino acid sequence SEQ ID NO: 4;

AB3 comprises a heavy chain having and a light, and wherein the heavy chain comprises a complementary determining region 1 (CDR1) having at least 85% identity to amino acid sequence SEQ ID NO: 29, a complementary determining region 2 (CDR2) having at least 85% identity to amino acid sequence SEQ ID NO: 17, and a complementary determining region 3 (CDR3) having at least 85% identity to amino acid sequence SEQ ID NO: 5, and wherein the light chain comprises a complementary determining region 1 (CDR1) having at least 85% identity to amino acid sequence SEQ ID NO: 30, a complementary determining region 2 (CDR2) having at least 85% identity to amino acid sequence SEQ ID NO: 18, and a complementary determining region 3 (CDR3) having at least 85% identity to amino acid sequence SEQ ID NO: 6;

AB4 comprises a heavy chain and a light chain, and wherein the heavy chain comprises a complementary determining region 1 (CDR1) having at least 85% identity to amino acid sequence SEQ ID NO: 31, a complementary determining region 2 (CDR2) having at least 85% identity to amino acid sequence SEQ ID NO: 19, and a complementary determining region 3 (CDR3) having at least 85% identity to amino acid sequence SEQ ID NO: 7, and wherein the light chain comprises a complementary determining region 1 (CDR1) having at least 85% identity to amino acid sequence SEQ ID NO: 32, a complementary determining region 2 (CDR2) having at least 85% identity to amino acid sequence SEQ ID NO: 20, and a complementary determining region 3 (CDR3) having at least 85% identity to amino acid sequence SEQ ID NO: 8;

AB5 comprises a heavy chain having and a light chain, and wherein the heavy chain comprises a complementary determining region 1 (CDR1) having at least 85% identity to amino acid sequence SEQ ID NO: 33, a complementary determining region 2 (CDR2) having at least 85% identity to amino acid sequence SEQ ID NO: 21, and a complementary determining region 3 (CDR3) having at least 85% identity to amino acid sequence SEQ ID NO: 9, and wherein the light chain comprises a complementary determining region 1 (CDR1) having at least 85% identity to amino acid sequence SEQ ID NO: 34, a complementary determining region 2 (CDR2) having at least 85% identity to amino acid sequence SEQ ID NO: 22, and a complementary determining region 3 (CDR3) having at least 85% identity to amino acid sequence SEQ ID NO: 10; and AB6 comprises a heavy chain having and a light chain, and wherein the heavy chain comprises a complementary determining region 1 (CDR1) having at least 85% identity to amino acid sequence SEQ ID NO: 35, a complementary determining region 2 (CDR2) having at least 85% identity to amino acid sequence SEQ ID NO: 23, and a complementary determining region 3 (CDR3) having at least 85% identity to amino acid sequence SEQ ID NO: 11, and wherein the light chain comprises a complementary determining region 1 (CDR1) having at least 85% identity to amino acid sequence SEQ ID NO: 36, a complementary determining region 2 (CDR2) having at least 85% identity to amino acid sequence SEQ ID NO: 24, and a complementary determining region 3 (CDR3) having at least 85% identity to amino acid sequence SEQ ID NO: 12.

According to an embodiment of the invention AB1 comprises a heavy chain having at least 85% identity to amino acid sequence SEQ ID NO: 85 and a light chain having at least 85% identity to amino acid sequence SEQ ID NO: 86, and wherein the heavy chain comprises a complementary determining region 1 (CDR1) having at least 90% identity to amino acid sequence SEQ ID NO: 25, a complementary determining region 2 (CDR2) having at least 90% identity to amino acid sequence SEQ ID NO: 13, and a complementary determining region 3 (CDR3) having at least 90% identity to amino acid sequence SEQ ID NO: 1, and wherein the light chain comprises a complementary determining region 1 (CDR1) having at least 90% identity to amino acid sequence SEQ ID NO: 26, a complementary determining region 2 (CDR2) having at least 90% identity to amino acid sequence SEQ ID NO: 14, and a complementary determining region 3 (CDR3) having at least 90% identity to amino acid sequence SEQ ID NO: 2;

AB2 comprises a heavy chain having at least 85% identity to amino acid sequence SEQ ID NO: 87 and a light chain having at least 85% identity to amino acid sequence SEQ ID NO: 88, and wherein the heavy chain comprises a complementary determining region 1 (CDR1) having at least 90% identity to amino acid sequence SEQ ID NO: 27, a complementary determining region 2 (CDR2) having at least 90% identity to amino acid sequence SEQ ID NO: 15, and a complementary determining region 3 (CDR3) having at least 90% identity to amino acid sequence SEQ ID NO: 3, and wherein the light chain comprises a complementary determining region 1 (CDR1) having at least 90% identity to amino acid sequence SEQ ID NO: 28, a complementary determining region 2 (CDR2) having at least 90% identity to amino acid sequence SEQ ID NO: 16, and a complementary determining region 3 (CDR3) having at least 90% identity to amino acid sequence SEQ ID NO: 4;

AB3 comprises a heavy chain having at least 85% identity to amino acid sequence SEQ ID NO: 89 and a light chain having at least 85% identity to amino acid sequence SEQ ID NO: 90, and wherein the heavy chain comprises a complementary determining region 1 (CDR1) having at least 90% identity to amino acid sequence SEQ ID NO: 29, a complementary determining region 2 (CDR2) having at least 90% identity to amino acid sequence SEQ ID NO: 17, and a complementary determining region 3 (CDR3) having at least 90% identity to amino acid sequence SEQ ID NO: 5, and wherein the light chain comprises a complementary determining region 1 (CDR1) having at least 90% identity to amino acid sequence SEQ ID NO: 30, a complementary determining region 2 (CDR2) having at least 90% identity to amino acid sequence SEQ ID NO: 18, and a complementary determining region 3 (CDR3) having at least 90% identity to amino acid sequence SEQ ID NO: 6;

AB4 comprises a heavy chain having at least 85% identity to amino acid sequence SEQ ID NO: 91 and a light chain having at least 85% identity to amino acid sequence SEQ ID NO: 92, and wherein the heavy chain comprises a complementary determining region 1 (CDR1) having at least 90% identity to amino acid sequence SEQ ID NO: 31, a complementary determining region 2 (CDR2) having at least 90% identity to amino acid sequence SEQ ID NO: 19, and a complementary determining region 3 (CDR3) having at least 90% identity to amino acid sequence SEQ ID NO: 7, and wherein the light chain comprises a complementary determining region 1 (CDR1) having at least 90% identity to amino acid sequence SEQ ID NO: 32, a complementary determining region 2 (CDR2) having at least 90% identity to amino acid sequence SEQ ID NO: 20, and a complementary determining region 3 (CDR3) having at least 90% identity to amino acid sequence SEQ ID NO: 8

AB5 comprises a heavy chain having at least 85% identity to amino acid sequence SEQ ID NO: 93 and a light chain having at least 85% identity to amino acid sequence SEQ ID NO: 94, and wherein the heavy chain comprises a complementary determining region 1 (CDR1) having at least 90% identity to amino acid sequence SEQ ID NO: 33, a complementary determining region 2 (CDR2) having at least 90% identity to amino acid sequence SEQ ID NO: 21, and a complementary determining region 3 (CDR3) having at least 90% identity to amino acid sequence SEQ ID NO: 9, and wherein the light chain comprises a complementary determining region 1 (CDR1) having at least 90% identity to amino acid sequence SEQ ID NO: 34, a complementary determining region 2 (CDR2) having at least 90% identity to amino acid sequence SEQ ID NO: 22, and a complementary determining region 3 (CDR3) having at least 90% identity to amino acid sequence SEQ ID NO: 10; and AB6 comprises a heavy chain having at least 85% identity to amino acid sequence SEQ ID NO: 95 and a light chain having at least 85% identity to amino acid sequence SEQ ID NO: 96, and wherein the heavy chain comprises a complementary determining region 1 (CDR1) having at least 90% identity to amino acid sequence SEQ ID NO: 35, a complementary determining region 2 (CDR2) having at least 90% identity to amino acid sequence SEQ ID NO: 23, and a complementary determining region 3 (CDR3) having at least 90% identity to amino acid sequence SEQ ID NO: 11, and wherein the light chain comprises a complementary determining region 1 (CDR1) having at least 90% identity to amino acid sequence SEQ ID NO: 36, a complementary determining region 2 (CDR2) having at least 90% identity to amino acid sequence SEQ ID NO: 24, and a complementary determining region 3 (CDR3) having at least 90% identity to amino acid sequence SEQ ID NO: 12.

According to a preferred embodiment of the invention AB1 comprises a heavy chain having at least 90% identity to amino acid sequence SEQ ID NO: 85 and a light chain having at least 90% identity to amino acid sequence SEQ ID NO: 86, and wherein the heavy chain comprises a complementary determining region 1 (CDR1) consisting of amino acid sequence SEQ ID NO: 25, a complementary determining region 2 (CDR2) consisting of amino acid sequence SEQ ID NO: 13, and a complementary determining region 3 (CDR3) consisting of amino acid sequence SEQ ID NO: 1, and wherein the light chain comprises a complementary determining region 1 (CDR1) consisting of amino acid sequence SEQ ID NO: 26, a complementary determining region 2 (CDR2) consisting of amino acid sequence SEQ ID NO: 14, and a complementary determining region 3 (CDR3) consisting of amino acid sequence SEQ ID NO: 2

AB2 comprises a heavy chain having at least 90% identity to amino acid sequence SEQ ID NO: 87 and a light chain having at least 90% identity to amino acid sequence SEQ ID NO: 88, and wherein the heavy chain comprises a complementary determining region 1 (CDR1) consisting of amino acid sequence SEQ ID NO: 27, a complementary determining region 2 (CDR2) consisting of amino acid sequence SEQ ID NO: 15, and a complementary determining region 3 (CDR3) consisting of amino acid sequence SEQ ID NO: 3, and wherein the light chain comprises a complementary determining region 1 (CDR1) consisting of amino acid sequence SEQ ID NO: 28, a complementary determining region 2 (CDR2) consisting of amino acid sequence SEQ ID NO: 16, and a complementary determining region 3 (CDR3) consisting of amino acid sequence SEQ ID NO: 4

AB3 comprises a heavy chain having at least 90% identity to amino acid sequence SEQ ID NO: 89 and a light chain having at least 90% identity to amino acid sequence SEQ ID NO: 90, and wherein the heavy chain comprises a complementary determining region 1 (CDR1) consisting of amino acid sequence SEQ ID NO: 29, a complementary determining region 2 (CDR2) consisting of amino acid sequence SEQ ID NO: 17, and a complementary determining region 3 (CDR3) consisting of amino acid sequence SEQ ID NO: 5, and wherein the light chain comprises a complementary determining region 1 (CDR1) consisting of amino acid sequence SEQ ID NO: 30, a complementary determining region 2 (CDR2) consisting of amino acid sequence SEQ ID NO: 18, and a complementary determining region 3 (CDR3) consisting of amino acid sequence SEQ ID NO: 6

AB4 comprises a heavy chain having at least 90% identity to amino acid sequence SEQ ID NO: 91 and a light chain having at least 90% identity to amino acid sequence SEQ ID NO: 92, and wherein the heavy chain comprises a complementary determining region 1 (CDR1) consisting of amino acid sequence SEQ ID NO: 31, a complementary determining region 2 (CDR2) consisting of amino acid sequence SEQ ID NO: 19, and a complementary determining region 3 (CDR3) consisting of amino acid sequence SEQ ID NO: 7, and wherein the light chain comprises a complementary determining region 1 (CDR1) consisting of amino acid sequence SEQ ID NO: 32, a complementary determining region 2 (CDR2) consisting of amino acid sequence SEQ ID NO: 20, and a complementary determining region 3 (CDR3) consisting of amino acid sequence SEQ ID NO: 8

AB5 comprises a heavy chain having at least 90% identity to amino acid sequence SEQ ID NO: 93 and a light chain having at least 90% identity to amino acid sequence SEQ ID NO: 94, and wherein the heavy chain comprises a complementary determining region 1 (CDR1) consisting of amino acid sequence SEQ ID NO: 33, a complementary determining region 2 (CDR2) consisting of amino acid sequence SEQ ID NO: 21, and a complementary determining region 3 (CDR3) consisting of amino acid sequence SEQ ID NO: 9, and wherein the light chain comprises a complementary determining region 1 (CDR1) consisting of amino acid sequence SEQ ID NO: 34, a complementary determining region 2 (CDR2) consisting of amino acid sequence SEQ ID NO: 22, and a complementary determining region 3 (CDR3) consisting of amino acid sequence SEQ ID NO: 10; and AB6 comprises a heavy chain having at least 90% identity to amino acid sequence SEQ ID NO: 95 and a light chain having at least 90% identity to amino acid sequence SEQ ID NO: 96, and wherein the heavy chain comprises a complementary determining region 1 (CDR1) consisting of amino acid sequence SEQ ID NO: 35, a complementary determining region 2 (CDR2) consisting of amino acid sequence SEQ ID NO: 23, and a complementary determining region 3 (CDR3) consisting of amino acid sequence SEQ ID NO: 11, and wherein the light chain comprises a complementary determining region 1 (CDR1) consisting of amino acid sequence SEQ ID NO: 36, a complementary determining region 2 (CDR2) consisting of amino acid sequence SEQ ID NO: 24, and a complementary determining region 3 (CDR3) consisting of amino acid sequence SEQ ID NO: 12.

According to another embodiment of the invention the heavy chain of AB1 has a variable region comprising a first framework region (FR1) consisting of amino acid sequence SEQ ID NO: 37, a second framework region (FR2) consisting of amino acid sequence SEQ ID NO: 38, a third framework region (FR3) consisting of amino acid sequence SEQ ID NO: 39, and a fourth framework region (FR4) consisting of amino acid sequence SEQ ID NO: 40, and wherein the light chain of AB1 has a variable region comprising a first framework region (FR1) consisting of amino acid sequence SEQ ID NO: 61, a second framework region (FR2) consisting of amino acid sequence SEQ ID NO: 62, a third framework region (FR3) consisting of amino acid sequence SEQ ID NO: 63, and a fourth framework region (FR4) consisting of amino acid sequence SEQ ID NO: 64;

the heavy chain of AB2 has a variable region comprising a first framework region (FR1) consisting of amino acid sequence SEQ ID NO: 41, a second framework region (FR2) consisting of amino acid sequence SEQ ID NO: 42, a third framework region (FR3) consisting of amino acid sequence SEQ ID NO: 43, and a fourth framework region (FR4) consisting of amino acid sequence SEQ ID NO: 44, and wherein the light chain of AB2 has a variable region comprising a first framework region (FR1) consisting of amino acid sequence SEQ ID NO: 65, a second framework region (FR2) consisting of amino acid sequence SEQ ID NO: 66, a third framework region (FR3) consisting of amino acid sequence SEQ ID NO: 67, and a fourth framework region (FR4) consisting of amino acid sequence SEQ ID NO: 68;

the heavy chain of AB3 has a variable region comprising a first framework region (FR1) consisting of amino acid sequence SEQ ID NO: 45, a second framework region (FR2) consisting of amino acid sequence SEQ ID NO: 46, a third framework region (FR3) consisting of amino acid sequence SEQ ID NO: 47, and a fourth framework region (FR4) consisting of amino acid sequence SEQ ID NO: 48, and wherein the light chain of AB3 has a variable region comprising a first framework region (FR1) consisting of amino acid sequence SEQ ID NO: 69, a second framework region (FR2) consisting of amino acid sequence SEQ ID NO: 70, a third framework region (FR3) consisting of amino acid sequence SEQ ID NO: 71, and a fourth framework region (FR4) consisting of amino acid sequence SEQ ID NO: 72 the heavy chain of AB4 has a variable region comprising a first framework region (FR1) consisting of amino acid sequence SEQ ID NO: 49, a second framework region (FR2) consisting of amino acid sequence SEQ ID NO: 50, a third framework region (FR3) consisting of amino acid sequence SEQ ID NO: 51, and a fourth framework region (FR4) consisting of amino acid sequence SEQ ID NO: 52, and wherein the light chain of AB4 has a variable region comprising a first framework region (FR1) consisting of amino acid sequence SEQ ID NO: 73, a second framework region (FR2) consisting of amino acid sequence SEQ ID NO: 74, a third framework region (FR3) consisting of amino acid sequence SEQ ID NO: 75, and a fourth framework region (FR4) consisting of amino acid sequence SEQ ID NO: 76;

the heavy chain of AB5 has a variable region comprising a first framework region (FR1) consisting of amino acid sequence SEQ ID NO: 53, a second framework region (FR2) consisting of amino acid sequence SEQ ID NO: 54, a third framework region (FR3) consisting of amino acid sequence SEQ ID NO: 55, and a fourth framework region (FR4) consisting of amino acid sequence SEQ ID NO: 56, and wherein the light chain of AB5 has a variable region comprising a first framework region (FR1) consisting of amino acid sequence SEQ ID NO: 77, a second framework region (FR2) consisting of amino acid sequence SEQ ID NO: 78, a third framework region (FR3) consisting of amino acid sequence SEQ ID NO: 79, and a fourth framework region (FR4) consisting of amino acid sequence SEQ ID NO: 80;

the heavy chain of AB6 has a variable region comprising a first framework region (FR1) consisting of amino acid sequence SEQ ID NO: 57, a second framework region (FR2) consisting of amino acid sequence SEQ ID NO: 58, a third framework region (FR3) consisting of amino acid sequence SEQ ID NO: 59, and a fourth framework region (FR4) consisting of amino acid sequence SEQ ID NO: 60, and wherein the light chain of AB6 has a variable region comprising a first framework region (FR1) consisting of amino acid sequence SEQ ID NO: 81, a second framework region (FR2) consisting of amino acid sequence SEQ ID NO: 82, a third framework region (FR3) consisting of amino acid sequence SEQ ID NO: 83, and a fourth framework region (FR4) consisting of amino acid sequence SEQ ID NO: 84.

In another aspect the present invention features an isolated nucleic acid molecule encoding a chimeric antigen receptor (CAR), wherein the CAR comprises an antibody or antibody fragment which includes an anti-CD123 binding domain, a transmembrane domain, and an intracellular signaling domain comprising at least a stimulatory domain, and wherein said anti-CD123 binding domain comprises:

(i) a heavy chain comprising a complementary determining region 1 (CDR1) having at least 90% identity to amino acid sequence SEQ ID NO: 25, a complementary determining region 2 (CDR2) having at least 90% identity to amino acid sequence SEQ ID NO: 13, and a complementary determining region 3 (CDR3) having at least 90% identity to amino acid sequence SEQ ID NO: 1, and a light chain comprising a complementary determining region 1 (CDR1) having at least 90% identity to amino acid sequence SEQ ID NO: 26, a complementary determining region 2 (CDR2) having at least 90% identity to amino acid sequence SEQ ID NO: 14, and a complementary determining region 3 (CDR3) having at least 90% identity to amino acid sequence SEQ ID NO: 2;

(ii) a heavy chain comprising a complementary determining region 1 (CDR1) having at least 90% identity to amino acid sequence SEQ ID NO: 27, a complementary determining region 2 (CDR2) having at least 90% identity to amino acid sequence SEQ ID NO: 15, and a complementary determining region 3 (CDR3) having at least 90% identity to amino acid sequence SEQ ID NO: 3, and a light chain comprising a complementary determining region 1 (CDR1) having at least 90% identity to amino acid sequence SEQ ID NO: 28, a complementary determining region 2 (CDR2) having at least 90% identity to amino acid sequence SEQ ID NO: 16, and a complementary determining region 3 (CDR3) having at least 90% identity to amino acid sequence SEQ ID NO: 4;

(iii) a heavy chain comprising a complementary determining region 1 (CDR1) having at least 90% identity to amino acid sequence SEQ ID NO: 29, a complementary determining region 2 (CDR2) having at least 90% identity to amino acid sequence SEQ ID NO: 17, and a complementary determining region 3 (CDR3) having at least 90% identity to amino acid sequence SEQ ID NO: 5, and a light chain comprising a complementary determining region 1 (CDR1) having at least 90% identity to amino acid sequence SEQ ID NO: 30, a complementary determining region 2 (CDR2) having at least 90% identity to amino acid sequence SEQ ID NO: 18, and a complementary determining region 3 (CDR3) having at least 90% identity to amino acid sequence SEQ ID NO: 6;

(iv) a heavy chain comprising a complementary determining region 1 (CDR1) having at least 90% identity to amino acid sequence SEQ ID NO: 31, a complementary determining region 2 (CDR2) having at least 90% identity to amino acid sequence SEQ ID NO: 19, and a complementary determining region 3 (CDR3) having at least 90% identity to amino acid sequence SEQ ID NO: 7, and a light chain comprising a complementary determining region 1 (CDR1) having at least 90% identity to amino acid sequence SEQ ID NO: 32, a complementary determining region 2 (CDR2) having at least 90% identity to amino acid sequence SEQ ID NO: 20, and a complementary determining region 3 (CDR3) having at least 90% identity to amino acid sequence SEQ ID NO: 8;

(v) a heavy chain comprising a complementary determining region 1 (CDR1) having at least 90% identity to amino acid sequence SEQ ID NO: 33, a complementary determining region 2 (CDR2) having at least 90% identity to amino acid sequence SEQ ID NO: 21, and a complementary determining region 3 (CDR3) having at least 90% identity to amino acid sequence SEQ ID NO: 9, and a light chain comprising a complementary determining region 1 (CDR1) having at least 90% identity to amino acid sequence SEQ ID NO: 34, a complementary determining region 2 (CDR2) having at least 90% identity to amino acid sequence SEQ ID NO: 22, and a complementary determining region 3 (CDR3) having at least 90% identity to amino acid sequence SEQ ID NO: 10 or (vi) a heavy chain comprising a complementary determining region 1 (CDR1) having at least 90% identity to amino acid sequence SEQ ID NO: 35, a complementary determining region 2 (CDR2) having at least 90% identity to amino acid sequence SEQ ID NO: 23, and a complementary determining region 3 (CDR3) having at least 90% identity to amino acid sequence SEQ ID NO: 11, and a light chain comprising a complementary determining region 1 (CDR1) having at least 90% identity to amino acid sequence SEQ ID NO: 36, a complementary determining region 2 (CDR2) having at least 90% identity to amino acid sequence SEQ ID NO: 24, and a complementary determining region 3 (CDR3) having at least 90% identity to amino acid sequence SEQ ID NO: 12.

According to an embodiment, the anti-CD123 binding domain of the isolated nucleic acid molecule of the invention is selected from the group consisting of an antibody, a Fv, a scFv, a Fab, or another antibody fragment, preferably a scFv. In another embodiment, the intracellular signaling domain is CD3-zeta (CD3ζ), optionally comprising a costimulatory domain selected from the group consisting of CD28, 4.1BB, Inducible T-cell COStimulator (ICOS), OX-40 or a combination thereof.

Another aspect of the present invention features an isolated polypeptide molecule encoded by the nucleic acid molecule described above.

A further aspect of the invention features an isolated chimeric antigen receptor (CAR) molecule comprising an antibody or antibody fragment which includes an anti-CD123 binding domain, a transmembrane domain, and an intracellular signaling domain comprising at least a stimulatory domain, and wherein said anti-CD123 binding domain comprises:

(i) a heavy chain comprising a complementary determining region 1 (CDR1) having at least 90% identity to amino acid sequence SEQ ID NO: 25, a complementary determining region 2 (CDR2) having at least 90% identity to amino acid sequence SEQ ID NO: 13, and a complementary determining region 3 (CDR3) having at least 90% identity to amino acid sequence SEQ ID NO: 1, and a light chain comprising a complementary determining region 1 (CDR1) having at least 90% identity to amino acid sequence SEQ ID NO: 26, a complementary determining region 2 (CDR2) having at least 90% identity to amino acid sequence SEQ ID NO: 14, and a complementary determining region 3 (CDR3) having at least 90% identity to amino acid sequence SEQ ID NO: 2;

(ii) a heavy chain comprising a complementary determining region 1 (CDR1) having at least 90% identity to amino acid sequence SEQ ID NO: 27, a complementary determining region 2 (CDR2) having at least 90% identity to amino acid sequence SEQ ID NO: 15, and a complementary determining region 3 (CDR3) having at least 90% identity to amino acid sequence SEQ ID NO: 3, and a light chain comprising a complementary determining region 1 (CDR1) having at least 90% identity to amino acid sequence SEQ ID NO: 28, a complementary determining region 2 (CDR2) having at least 90% identity to amino acid sequence SEQ ID NO: 16, and a complementary determining region 3 (CDR3) having at least 90% identity to amino acid sequence SEQ ID NO: 4;

(iii) a heavy chain comprising a complementary determining region 1 (CDR1) having at least 90% identity to amino acid sequence SEQ ID NO: 29, a complementary determining region 2 (CDR2) having at least 90% identity to amino acid sequence SEQ ID NO: 17, and a complementary determining region 3 (CDR3) having at least 90% identity to amino acid sequence SEQ ID NO: 5, and a light chain comprising a complementary determining region 1 (CDR1) having at least 90% identity to amino acid sequence SEQ ID NO: 30, a complementary determining region 2 (CDR2) having at least 90% identity to amino acid sequence SEQ ID NO: 18, and a complementary determining region 3 (CDR3) having at least 90% identity to amino acid sequence SEQ ID NO: 6;

(iv) a heavy chain comprising a complementary determining region 1 (CDR1) having at least 90% identity to amino acid sequence SEQ ID NO: 31, a complementary determining region 2 (CDR2) having at least 90% identity to amino acid sequence SEQ ID NO: 19, and a complementary determining region 3 (CDR3) having at least 90% identity to amino acid sequence SEQ ID NO: 7, and a light chain comprising a complementary determining region 1 (CDR1) having at least 90% identity to amino acid sequence SEQ ID NO: 32, a complementary determining region 2 (CDR2) having at least 90% identity to amino acid sequence SEQ ID NO: 20, and a complementary determining region 3 (CDR3) having at least 90% identity to amino acid sequence SEQ ID NO: 8;

(v) a heavy chain comprising a complementary determining region 1 (CDR1) having at least 90% identity to amino acid sequence SEQ ID NO: 33, a complementary determining region 2 (CDR2) having at least 90% identity to amino acid sequence SEQ ID NO: 21, and a complementary determining region 3 (CDR3) having at least 90% identity to amino acid sequence SEQ ID NO: 9, and a light chain comprising a complementary determining region 1 (CDR1) having at least 90% identity to amino acid sequence SEQ ID NO: 34, a complementary determining region 2 (CDR2) having at least 90% identity to amino acid sequence SEQ ID NO: 22, and a complementary determining region 3 (CDR3) having at least 90% identity to amino acid sequence SEQ ID NO: 10;

or (vi) a heavy chain comprising a complementary determining region 1 (CDR1) having at least 90% identity to amino acid sequence SEQ ID NO: 35, a complementary determining region 2 (CDR2) having at least 90% identity to amino acid sequence SEQ ID NO: 23, and a complementary determining region 3 (CDR3) having at least 90% identity to amino acid sequence SEQ ID NO: 11, and a light chain comprising a complementary determining region 1 (CDR1) having at least 90% identity to amino acid sequence SEQ ID NO: 36, a complementary determining region 2 (CDR2) having at least 90% identity to amino acid sequence SEQ ID NO: 24, and a complementary determining region 3 (CDR3) having at least 90% identity to amino acid sequence SEQ ID NO: 12.

Another aspect of the invention features an isolated chimeric antigen receptor (CAR) molecule, wherein the said CAR is as described above.

Another aspect of the invention features an expression vector comprising a nucleic acid molecule of the invention, wherein the vector is selected from the group consisting of a DNA, a RNA, a plasmid, a lentivirus vector, an adenoviral vector, or a retrovirus vector.

Another aspect of the invention features an engineered immune cell comprising the nucleic acid molecule of the invention or the vector of an invention. In an embodiment of the invention the cell expresses a CAR as described above at its membrane. According to an embodiment, the cell is for use as a medicament, preferentially for use in the treatment of a proliferative disease in a mammal, preferably a human, wherein the proliferative disease is a disease associated with CD123 overexpression, preferably Blastic Plasmacytoid Dendritic Cell Neoplasm (BPDCN).

A further aspect of the invention features a pharmaceutical composition comprising the engineered immune cell as described above and a pharmaceutical excipient.

Yet another aspect of the invention features a method of engineering an immune cell comprising a transduction of a cell with an expression vector as described above.

A further aspect of the present invention features an isolated nucleic acid molecule encoding a chimeric antigen receptor (CAR), wherein the nucleic acid molecule consists of a sequence having an identity of at least 85%, preferentially 90%, more preferentially 95%, and most preferentially of a 100% to SEQ ID NO: 97.

Other features and advantages of the invention will stand out and/or become clear upon reading the following description, which comprises specific examples given in an illustrative and non-limiting manner, as well as from the drawings in which:

FIG. 1 shows the nucleotide sequence and the amino acid sequence of complementary determining region 1 (CDR1), complementary determining region 2 (CDR2) and complementary determining region 3 (CDR3) of both the heavy chain and the light chain of the antibodies of the invention;

FIG. 2 shows the nucleotide sequence and the amino acid sequence of framework region 1 (FR1), framework region 2 (FR2), framework region 3 (FR3) and framework region 4 (FR4) of the heavy chain of the antibodies of the invention;

FIG. 3 shows the nucleotide sequence and the amino acid sequence of framework region 1 (FR1), framework region 2 (FR2), framework region 3 (FR3) and framework region 4 (FR4) of the light chain of the antibodies of the invention;

FIG. 4 shows the consensus amino acid sequence of the light chain and the consensus amino acid sequence of the heavy chain of a first antibody of the invention;

FIG. 5 shows the consensus amino acid sequence of the light chain and the consensus amino acid sequence of the heavy chain of a second antibody of the invention;

FIG. 6 shows the consensus amino acid sequence of the light chain and the consensus amino acid sequence of the heavy chain of a third antibody of the invention;

FIG. 7 shows the consensus amino acid sequence of the light chain and the consensus amino acid sequence of the heavy chain of a fourth antibody of the invention;

FIG. 8 shows the consensus amino acid sequence of the light chain and the consensus amino acid sequence of the heavy chain of a fifth antibody of the invention;

FIG. 9 shows the consensus amino acid sequence of the light chain and the consensus amino acid sequence of the heavy chain of a sixth antibody of the invention named;

FIG. 13 shows a nucleic acid sequence of a chimeric antigen receptor according to the invention;

Figure 19:
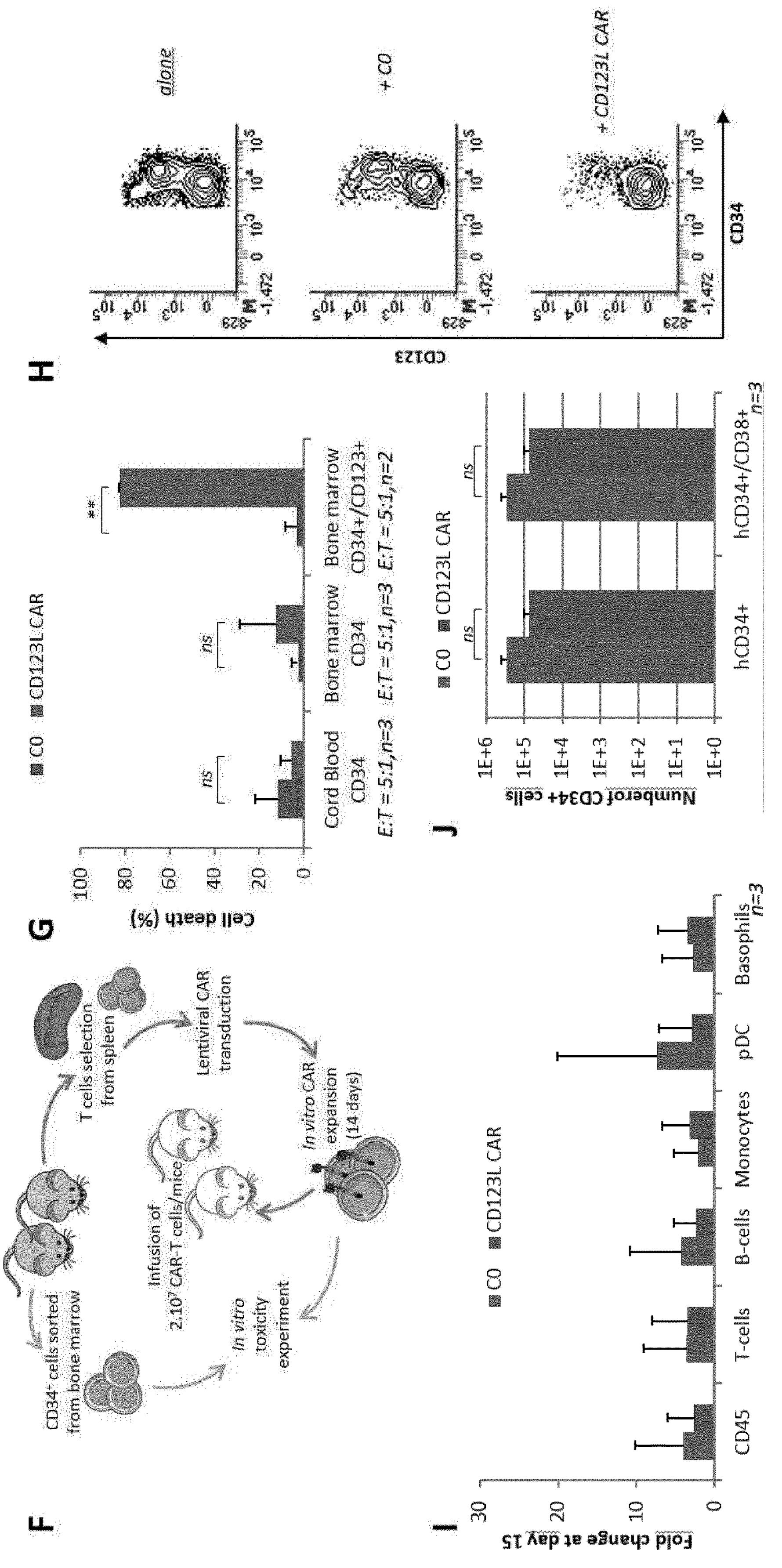
Figure 20:
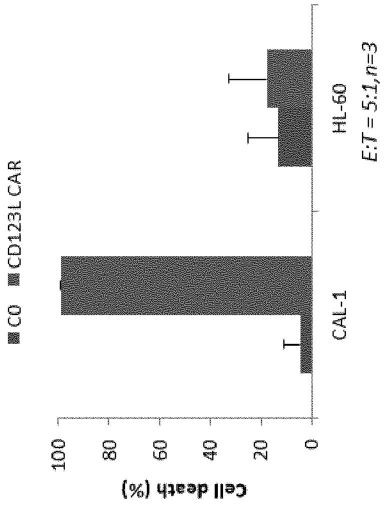
Figure 21:
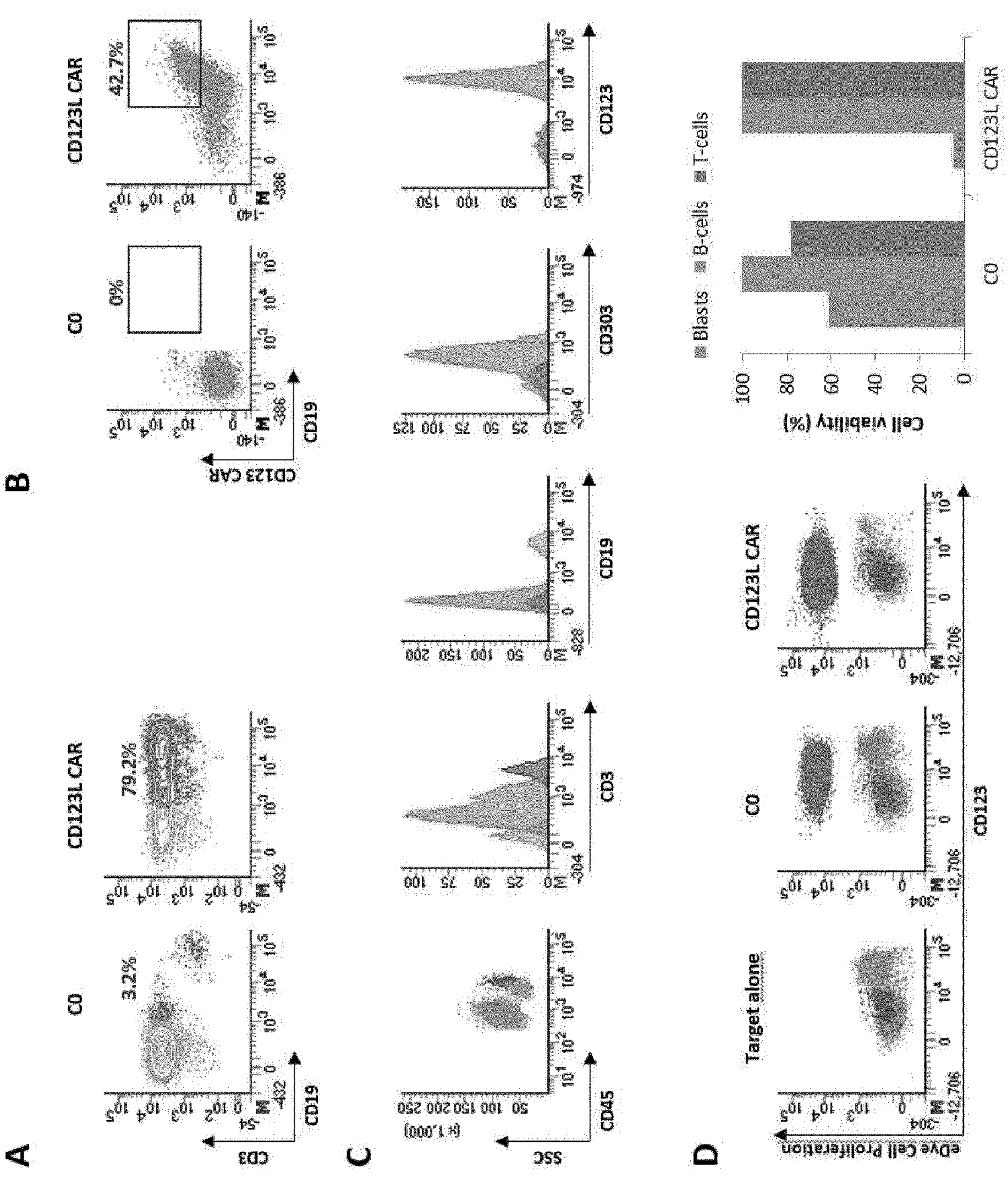

FIG. 19 shows a fluorescence graph relative to CD123 expression in different cell types, an immunohistochemistry picture of CD123 expression in tumor and normal tissues, flow cytometry graphs relative to CD123 expression, a diagram of the production of autologous T cells of the invention, and flow cytometry graphs relative toxicity of T cells of the invention to CD123 against cells expressing CD123 at a low level;

FIG. 20 shows graphs based on flow cytometry relative to evaluation of toxicity of T cells of autologous T cells against cell lines (CAL-1 and DAUDI); and FIG. 21 shows flow cytometry graphs relative to CD123 T cells of the invention from BPDCN patient induced specific cytotoxicity against autologous BPDCN blasts.

The drawings and the description herein contain, for the most part, elements of definite nature. Therefore, description and drawings not only are being used to better understand the present invention, but also to contribute to the definition therefor, when appropriate.

In the present description, the term "and/or" should be interpreted as encompassing that one or more of the cases it connects may occur. For example, the wording "proteins or protein sequences can be prepared using standard recombinant and/or synthetic methods" indicates that proteins or protein sequences can be prepared using both standard recombinant and synthetic methods, or that proteins or protein sequences can be prepared using standard recombinant methods or indicates that proteins, or that proteins or protein sequences can be prepared using synthetic methods. More generally, the term "and/or" as used in a phrase such as "A and/or B" is intended to include "A and B", "A or B", "A" and "B". Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "comprising" is to be interpreted as encompassing all specifically mentioned features as well optional, additional, unspecified ones. More generally, the terms "comprise", "comprises" and "comprising" will be understood to imply the inclusion of a stated step or element or group of steps or elements but not the exclusion of any other step or element or group of steps or elements. The term "consisting of" is to be interpreted as no features other than the specifically mentioned features are present. Further, the indefinite article "a" or "an" does not exclude a plurality.

When reference is made throughout the present description to "one embodiment", "an embodiment", "a particular embodiment", "a certain embodiment", "an additional embodiment", "another embodiment" or "a further embodiment" or "one aspect", "an aspect", "a particular aspect", "a certain aspect", "an additional aspect", "another aspect" or "a further aspect" combinations thereof means that a particular feature, structure or characteristic described in connection with the embodiment is included in at least one embodiment of the present invention. The articles "a", "an" and "the" are used herein to refer to one or to more than one (i.e. to at least one) of the grammatical object of the article.

The term "gene" means a DNA sequence (nucleic acid sequence or nucleotide sequences) that codes for a particular sequence of amino acids. A gene comprises all or part of one or more proteins or enzymes, and may include regulatory DNA sequences (such as promoter sequences) which determine at least partially the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

The terms "identical" or percent (%) "identity" in the context of two or more nucleic acids sequences or amino acid sequences, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al., Proc. Natl. Acad. Sci. 87:2264-2268, 1990, as modified in Karlin et al., Proc. Natl. Acad. Sci. 90:5873-5877, 1993, and incorporated into the NBLAST and XBLAST programs (Altschul et al., Nucleic Acids Res. 25:3389-3402, 1991). Gapped BLAST can also be used as described in Altschul et al., Nucleic Acids Res. 25:3389-3402, 1997; BLAST-2, WU-BLAST-2 (Altschul et al., Methods in Enzymology 266:460-480, 1996), ALIGN, ALIGN-2 (Genentech, South San Francisco, California) or Megalign (DNASTAR) are additional publicly available software programs that can be used to align sequences. Further, the algorithm of Needleman and Wunsch (J. Mol. Biol. (48):444-453, 1970) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, the percent identity between nucleotide or amino acid sequences can be determined using the algorithm of Myers and Miller (CABIOS, 4: 11-17, 1989). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. Usually, the default parameters of the alignment software are used.

A sequence "at least 85% identical to a reference sequence", or "something having at least 85% identity to a reference sequence" is a sequence having, on its entire length, 85%, or more, in particular 90%, 91%, 92%, 93%, 94%, 95%, 96%, 97%, 98%, 99% or 100% sequence identity with the entire length of the reference sequence. In the context, the present description, the "percentage of identity" is calculated using a pairwise alignment (i.e. the two sequences are compared over their entire length). As mentioned above, methods for comparing the identity of two or more sequences are well known in the art. For instance, bioinformatics tools or programs, such as EMBOSS Needle available on the ebi.ac.uk Website, may be used to generate pairwise sequence alignments of the present invention. Commonly, many bioinformatics tools and programs use the Needleman-Wunsch algorithm (Needleman and Wunsch, 1970 J. Mol. Biol. 48:443-453) to find the optimum alignment (including gaps) of two sequences when considering their entire length. However, other algorithms may be implemented in a variety of bioinformatics tools or programs.

More generally, for the purposes of the present invention, the "sequence identity" or "sequence homology" is calculated by comparing two aligned sequences in a comparison window. The sequence alignment enables to determine the number of positions (nucleotides or amino acids) common to both of the two sequences in the comparison window. The number of common positions is then divided by the total number of positions in the comparison window and multiplied by hundred to obtain the percentage of homology. The determination of the percentage of sequence identity can be done manually or by using well-known bioinformatics computer programs.

The percentage of identity between two polypeptides, in accordance with the invention, can be calculated using the EMBOSS: needle (global) program with a "Gap Open" parameter equal to 10.0, a "Gap Extend" parameter equal to 0.5, and a Blosum62 matrix.

Proteins, or a part thereof, having (or consisting of) an amino acid sequence "at least 80%, 85%, 90%, 95%, 96%, 97%, 98% or 99% identical" to a reference sequence may comprise mutations such as deletions, insertions and/or substitutions compared to the reference sequence.

In case of substitutions, the protein consisting of an amino acid sequence at least 80%, 85%, 90%, 95%, 96%, 97%, 98% or 99% identical to a reference sequence may correspond to a homologous sequence derived from another species than the reference sequence (i.e. "homology"). Substitutions of amino acids may be conservative or non-conservative. Conservative substitutions are substitutions wherein one amino acid is substituted for another amino acid with a similar side chain, i.e. similar structural and/or similar chemical properties. In this regard, conservative substitutions may occur between:

- amino acids with non-polar side chains: glycine (Gly), alanine (Ala), valine (Val), leucine (Leu), isoleucine (Ile), proline (Pro), phenylalanine (Phe), methionine (Met), tryptophan (Trp);
- amino acids with uncharged polar side chains: asparagine (Asn), glutamine (Gln), serine (Ser), threonine (Thr), tyrosine (Tyr), cysteine (Cys);
- amino acids with acidic side chains: aspartic acid (Asp), glutamic acid (Glu);
- amino acids with basic side chains: lysine (Lys), arginine (Arg), histidine (His);
- amino acids with beta-branched side chains: threonine (Thr), valine (Val), isoleucine (Ile);
- amino acids with aromatic side chains: tyrosine (Tyr), phenylalanine (Phe), tryptophan (Trp) histidine (His).

Non-conservative substitutions may occur randomly between the above. Other definitions may be given to conservative or non-conservative substitutions depending on the positions of individual amino acids within the tridimensional shape of the protein.

The techniques of the invention uses, unless indicated otherwise, are methods of chemistry, biochemistry, organic chemistry, molecular biology, microbiology, recombinant DNA techniques, genetics, genetic and/or biotechnological cell engineering, immunology, and cell biology that are known by the skilled person. When needed, such methods are described for the purpose of illustration. Most of those methods and other techniques are described in literature. See, e.g., Sambrook, et at., Molecular Cloning: A Laboratory Manual (3rd Edition, 2001); Sambrook, et at., Molecular Cloning: A Laboratory Manual (2nd Edition, 1989); Maniatis et al., Molecular Cloning: A Laboratory Manual (1982); Ausubel et al., Current Protocols in Molecular Biology (John Wiley and Sons, updated July 2008); Short Protocols in Molecular Biology: A Compendium of Methods from Current Protocols in Molecular Biology, John Wiley and Sons, 4$^{th}$ Ed. 1999; DNA Cloning: A Practical Approach, vol. I & II (IRL Press, Oxford, 1985); Techniques for the Analysis of Complex Genomes, Anand, Academic Press, 1992; Transcription and Translation, B. Names & S. Higgins, 1984; A Practical Guide to Molecular Cloning, Perbal, 1984; Antibodies, Harlow and Lane, Cold Spring Harbor Laboratory Press, Cold Spring Harbor, 1998; Current Protocols in Immunology, Q. E. Coligan, A. M. Kruisbeek, D. H. Margulies, E. M. Shevach and W. Strober, 1991; Annual Review of Immunology. Unless defined otherwise, all technical and scientific terms used herein have the same meaning as commonly understood by those of ordinary skill in the art in the field of the invention. Although any methods and materials similar or equivalent to those described herein can be used in the practice or testing of the present invention, preferred embodiments of compositions, methods and materials are described herein.

As understood by the skilled person and as described herein, an "antibody", also called "immunoglobulin" comprises two heavy chains and two light chains. Each heavy chain consists of a variable region and a first, second, and third constant regions, while each light chain consists of a variable region and a constant region. two heavy chains are linked to each other by disulfide bonds wherein each heavy chain is linked to a light chain by a disulfide bond.

In mammals, there are two types of light chain, lambda (I) and kappa (k). Further, there are five main heavy chain classes (or isotypes) classified as a, d, e, y, and m which determine the functional activity of an antibody molecule: IgA, IgD, IgE, IgG, and IgM.

Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). More precisely the complete antibody forms a "Y" shape. The base or stem of the Y consists of the second and third constant regions (and for IgE and IgM, the fourth constant region) of two heavy chains bound together by disulfide bonds, sometimes called inter-chain disulfide bonds forming the hinge. Heavy chains y, and d have a constant region composed of three tandem (inline) Ig domains, and a hinge region for added flexibility; heavy chains m and e have a constant region composed of four immunoglobulin domains. The second and third constant regions are referred to as "CH2 domain" and "CH3 domain", respectively. Each arm or branch of the Y includes the variable region and first constant region of a single heavy chain bound to the variable and constant regions of a single light chain. The variable regions of the light and heavy chains are responsible for antigen binding. More generally, the variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant.

Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences that together define the binding affinity and specificity of the natural Fv region of a native immunoglobulin binding site. The light and heavy chains of an immunoglobulin each have three CDRs, commonly designated CDR1, CDR2 and CDR3, or more precisely designated CDR1-L, CDR2-L, CDR3-L and CDR1-H, CDR2-H, CDR3-H, respectively. Other nomenclatures can be found in literature Thus, the CDRs located in the variable domain of the heavy chain of the antibody can be referred to as CDRH 1, CDRH2, and CDRH3, whereas the CDRs located in the variable domain of the light chain of the antibody can be referred to as CDRL1, CDRL2, and CDRL3. Antibodies with different specificities (i.e., different combining sites for different antigens) have different CDRs. A conventional antibody antigen-binding site, therefore, includes six CDRs, comprising the CDR set from each of a heavy and a light chain V region.

As mentioned above, light and heavy chain variable regions contain so called "framework" region that interrupted by the hypervariable CDR regions. The CDRs can be defined or identified by methods, such as by sequence according to Kabat et al., Wu, TT and Kabat, E. A., J Exp Med, 132(2):211-50, 1970; Borden, P. and Kabat E. A., PNAS, 84: 2440-2443, 1987; Kabat et al., Sequences of Proteins of Immunological Interest, U.S. Department of Health and Human Services, 1991—or by structure according to Chothia et al.—Choithia, C. and Lesk, A.M., J Mol. Biol., 196(4): 901-917, 1987; Choithia, C. et al., Nature, 342: 877-883, 1989.

The sequences of the framework regions of different light or heavy chains are relatively conserved within a species, such as humans. More generally, "Framework Regions" (FRs) are relatively conserved among different immunoglobulins in a single species. The framework region of an antibody, which is somewhat the combination of all framework regions of the constituent light and heavy chains, serves to position and align the CDRs in three-dimensional space, i.e. when the antibody is folded and active. The CDRs are primarily responsible for binding to an epitope of an antigen. As mentioned above, the CDRs of each chain are referred to as CDR1, CDR2, and CDR3. In fact, the CDRs are numbered sequentially starting from the N-terminus. The light and heavy chains of an immunoglobulin each have four FRs, designated FR1, FR2, FR3 and FR4, or more precisely for the light chain FR1-L, FR2-L, FR3-L, FR4-L, and for the light chain FR1-H, FR2-H, FR3-H, FR4-H, respectively. Accordingly, the light chain variable domain may thus be designated as (FR1-L)-(CDR1-L)-(FR2-L)-(CDR2-L)-(FR3-L)-(CDR3-L)-(FR4-L) and the heavy chain variable domain may thus be designated as (FR1-H)-(CDR1-H)-(FR2-H)-(CDR2-H)-(FR3-H)-(CDR3-H)-(FR4-H). Knowing the amino acid sequence of the CDRs one skilled in the art can easily determine the framework regions FR1-L, FR2-L, FR3-L, FR4-L and/or FR1-H, FR2-H, FR3-H, FR4-H.

References in the present description to "VH" or "VH" refer to the variable region of an immunoglobulin heavy chain, including that of an antibody, Fv, scFv, Fab, or other antibody fragment as disclosed herein. References to "VL" or "VL" refer to the variable region of an immunoglobulin light chain, including that of an antibody, Fv, scFv, dsFv, Fab, or other antibody fragment as disclosed herein.

As used herein, the term "antibody" or "immunoglobulin" mainly denotes conventional antibodies, particularly monoclonal antibodies, and fragments thereof, as well as single domain antibodies and fragments thereof, in particular variable heavy chain of single domain antibodies, and further denotes chimeric antibodies, humanized, bispecific or multispecific antibodies. The antibody is preferably a human antibody, a murine antibody, or a humanized antibody.

A "monoclonal antibody" or "mAb" is an antibody produced by a single clone of B lymphocytes or by a cell into which the heavy and the light chain genes of a single antibody have been transfected. Monoclonal antibodies are produced by methods well known in the art, for instance by making hybrid antibody-forming cells from a fusion of myeloma cells with immune spleen cells or by recombination techniques, i.e. production by protein engineering. Monoclonal antibodies include humanized monoclonal antibodies. More generally, a monoclonal antibody is a molecule of a single amino acid composition that is directed against a specific antigen, and is not to be construed as requiring production of the antibody by any particular method other than those known in the art.

The term "chimeric antibody" refers to an engineered antibody which in its broadest sense contains one or more regions from one antibody and one or more regions from one or more other antibodies. In particular a chimeric antibody comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens.

The term "antibody" or "immunoglobulin" also includes the meaning of "single domain antibodies" which have been more recently described and developed. Single domain antibodies are antibodies whose complementary determining regions (CDRs) are part of a single domain polypeptide. Examples of single domain antibodies include heavy chain antibodies, antibodies naturally devoid of light chains, single domain antibodies derived from conventional four-chain antibodies, as well as engineered single domain antibodies. Single domain antibodies may be derived from any species, especially from mouse, human or rabbit. Single domain antibodies may be naturally occurring single domain antibodies known as heavy chain antibody devoid of light chains. In particular, Camelidae species (e.g. camel, dromedary, llama, alpaca and guanaco) produce heavy chain antibodies naturally devoid of light chain.

The variable heavy chain of these single domain antibodies devoid of light chains are known in the art as "VHH" or NANOBODY®. Similar to conventional VH domains, VHHs contain four framework regions (FRs) and three complementary determining regions (CDRs). One particular advantage of Nanobodies over conventional antibodies is that they are about ten times smaller than IgG molecules. Consequently, properly folded functional nanobodies can be produced by in vitro expression with a high yield. Furthermore, the art describes nanobodies as being very stable, and resistant to the action of proteases. The properties and production of nanobodies have been reviewed for instance in Harmsen and De Haard H J, Appl. Microbiol. Biotechnol., 2007, November, 77(1):13-22.

In certain preferred embodiments, the antibody is a humanized antibody (such as a humanized monoclonal antibody) that specifically binds to a surface protein on a tumor cell. A "humanized" antibody is an immunoglobulin including a human framework region and one or more CDRs from a non-human (for example a mouse, rat, or synthetic) immunoglobulin. Hence, all parts of a humanized immunoglobulin, except possibly the CDRs, are substantially identical to corresponding parts of natural human immunoglobulin sequences. Humanized or other monoclonal antibodies can have additional conservative amino acid substitutions, which have substantially no effect on antigen binding or other immunoglobulin functions. Humanized antibodies can be constructed by means of genetic engineering (see for example, U.S. Pat. No. 5,585,089).

More generally, the term "humanized antibody" refers to an antibody which is wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains. Numerous methods for humanization of an antibody sequence are known in the art; see e.g. the review by Almagro & Fransson, 2008, Front Biosci. 13: 1619-1633. One commonly used method is the so called CDR grafting or antibody reshaping. This technique involves grafting of the CDR sequences of a donor antibody, commonly a mouse antibody, into the framework scaffold of a human antibody of different specificity. Since CDR grafting may reduce the binding specificity and affinity, and thus the biological activity, of a CDR grafted non-human antibody, back mutations may be introduced at selected positions of the CDR grafted antibody in order to retain the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues. Another alternative technique is known as the so called guided selection, cf. Jespers et al., Biotechnology 12, 899, 1994, and can be used to derive from for example a murine or rat antibody a fully human antibody conserving the epitope and binding characteristics of the parental antibody. A further method of humanization is the so called 4D-humanization. The 4D-humanization protocol is described in the patent application WO2009032661A1 (or US20110027266) and is exemplified in the following applying the 4D-humanization to humanize the rat antibody variable light (VL) and heavy (VH) domains. In one example, a rat antibody homology model was done with typically MOE software (v. 201 1.10—Chemical Computing Group, Quebec, Canada) using PDB structures, cf. Berman et al., Nucleic Acids Research, 28:235-242, 2000 as templates and was subsequently energy minimized using the standard procedures implemented in MOE. A molecular dynamics (MD) simulation was then performed on the minimized 3D homology model (done with MOE software) of rat antibody and compared to the, for example, 49 human models derived from the seven representative light chains (vk1, vk2, vk3, vk4, vlambda1, vlambda2, vlambda3) and the seven representative heavy chains (vh1 a, vh1 b, vh2, vh3, vh4, vh5, vh6) designed by LGCR/SDI and available within MOE. For instance, one model of chains couple (Vkx-Vhx) with the best both hydrophobic, electrostatic components and sequence identity outside CDR has been selected for the 4D-humanization. For the pairwise association between the rat antibody variable domain and the selected model, the sequences were aligned based typically on the optimal 3D superposition of the alpha carbons of the corresponding homology models. The unwanted motifs were then considered and mutated. Finally, the resulting humanized sequences were blasted for sequence similarity against, for instance, the IEDB database to ensure that none of the sequences contain any known B- or T-cell epitope listed in.

For chimeric antibodies, humanization typically involves modification of the framework regions of the variable region sequences.

Amino acid residues that are part of a CDR will typically not be altered in connection with humanization, although in certain cases it may be desirable to alter individual CDR amino acid residues, for example to remove a glycosylation site, a deamidation site or an undesired cysteine residue. N-linked glycosylation occurs by attachment of an oligosaccharide chain to an asparagine residue in the tripeptide sequence Asn-x-Ser or Asn-X-Thr, where X may be any amino acid except Pro. Removal of an N-glycosylation site may be achieved by mutating either the Asn or the Ser/Thr residue to a different residue, in particular by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues. Substitution in a CDR sequence to remove one of the implicated residues is also intended to be encompassed by the present invention.

The term antibodies also include antigen binding fragments thereof. Such "fragments" comprise a portion of an intact antibody, in particular the antigen binding region or variable region of the intact antibody. Examples of antibody fragments include Fab' fragments, F(ab)'2 fragments, Fv, single chain Fv proteins ("scFv") and portions of full length antibodies responsible for antigen binding, diabodies, bispecific and multispecific antibodies formed from antibody fragments. A fragment of a conventional antibody may also be a single domain antibody, such as a heavy chain antibody or VHH. The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond. The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin. "Single-chain Fv" or "scFv" antibody fragments comprise the VH and VL domains of antibody, wherein these domains are present in a single polypeptide chain and in either orientation (e.g. VL-VH or VH-VL). Single chain may be cloned form the V region genes of a hybridoma specific for a desired target. The production of such hybridomas has become routine. A technique which can be used for cloning the variable region heavy chain (VH) and variable region light chain (VL) has been described, for example, in Orlandi et al., PNAS, 1989, 86: 3833-3837. Usually, the scFv polypeptide further comprises a polypeptide linker between the VH and VL domains which enables the scFv to form the desired structure for antigen binding. More specifically, a single chain Fv ("scFv") polypeptide is a covalently linked VH::VL heterodimer which is usually expressed from a gene fusion including VH and VL encoding genes linked by a peptide-encoding linker. In some embodiments, human scFv fragment of include CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent sc(Fv)2. "dsFv" is a VH::VL heterodimer stabilized by a disulphide bond. "(dsFv)2" denotes two dsFv coupled by a peptide linker. The term "bispecific antibody" or "BsAb" typically denotes an antibody, which combines the antigen-binding sites of two antibodies within a single molecule. Thus, BsAbs are able to bind two different antigens simultaneously. Genetic engineering has been used with increasing frequency to design, modify, and produce antibodies or antibody derivatives with a desired set of binding properties and effector functions as described for instance in EP2050764A1. The term "multispecific antibody" denotes an antibody that combines the antigen-binding sites of two or more antibodies within a single molecule. The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

The present invention provides immune effector cells genetically engineered with vectors designed to express Chimeric Antigen Receptors (CARs) that redirect cytotoxicity toward tumor cells. CARs are molecules that combine antibody-based specificity for a target antigen (e.g. tumor antigen) with a T cell receptor-activating intracellular domain to generate a chimeric protein that exhibits a specific anti-tumor cellular immune activity. As used herein, the term, "chimeric" describes being composed of parts of different proteins or DNAs from different origins. The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors.

As used herein, the terms "binding domain", "extracellular binding domain", "antigen-specific binding domain", and "extracellular antigen specific binding domain", are used interchangeably and provide a CAR with the ability to specifically bind to the target antigen of interest. A binding domain may comprise any protein, polypeptide, oligopeptide, or peptide that possesses the ability to specifically recognize and bind to a biological molecule {e.g. a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest. The terms "specific binding affinity" or "specifically binds" or "specifically bound" or "specific binding" or "specifically targets" as used herein, describe binding of one molecule to another at greater binding affinity than background binding. A binding domain (or a CAR comprising a binding domain or a fusion protein containing a binding domain) "specifically binds" to a target molecule if it binds to or associates with a target molecule with an affinity or Ka (i.e. an equilibrium association constant of a particular binding interaction with units of 1/M) of, for example, greater than or equal to about $10^5$ $M^{-1}$. Affinities of binding domain polypeptides and CAR proteins according to the present disclosure can be readily determined using conventional techniques like competitive ELISA (enzyme-linked immunosorbent assay). Further the binding quality related to the affinity may be determined, quantified and qualified the so called $K_D$ Value. The $K_D$ and correlates to antibody affinity and sensitivity. $K_D$ is the equilibrium dissociation constant, a ratio of $k_{off}/k_{on}$, between the antibody and its antigen. $K_D$ and affinity are inversely related. The $K_D$ value relates to the concentration of antibody (the amount of antibody needed for a particular experiment) and so the lower the $K_D$ value (lower concentration) and thus the higher the affinity of the antibody. $K_D$ is the ratio of the antibody dissociation rate ($k_{off}$), how quickly it dissociates from its antigen, to the antibody association rate ($k_{on}$) of the antibody, how quickly it binds to its antigen. The $K_D$ values of the present description were determined by measuring the $k_{on}$ and $k_{off}$ rates of a specific antibody/antigen interaction and then using a ratio of these values to calculate the $K_D$ value. More generally, the affinity of an antibody is the strength of binding of a single molecule to its ligand. It is typically measured and reported by the equilibrium dissociation constant ($K_D$), which is used to evaluate and rank order strengths of bimolecular interactions. The binding of an antibody to its antigen is a reversible process, and the rate of the binding reaction is proportional to the concentrations of the reactants. At equilibrium, the rate of [antibody]|[antigen]complex formation is equal to the rate of dissociation into its components [antibody]+[antigen]. The measurement of the reaction rate constants can be used to define an equilibrium or affinity constant ($1/K_D$). In short, the smaller the $K_D$ value the greater the affinity of the antibody for its target.

The binding domain of the CAR is commonly followed by one or more "hinge regions". Hinge regions play a role in positioning the antigen binding domain away from the effector cell surface to enable proper cell-to-cell contact, antigen binding and activation. A CAR can have one or more hinge regions between the binding domain and the transmembrane domain. As described in the art hinge regions may be derived from a natural, synthetic, semi-synthetic, or recombinant source.

The "transmembrane domain" is a CAR portion that fuses the extracellular binding portion and intracellular signaling domain. The transmembrane domain anchors the CAR to the plasma membrane of the immune effector cell. As described in the art transmembrane regions may be derived from a natural, synthetic, semi-synthetic, or recombinant source.

In preferred embodiments, CARs of the invention comprise an intracellular signaling domain. An "intracellular signaling domain" refers to the part of a CAR that participates in transducing the message of effective CAR binding to the target antigen into the interior of the immune effector cell to elicit effector cell function, e.g. activation, cytokine production, proliferation and cytotoxic activity, including the release of cytotoxic factors to the CAR-bound target cell, or other cellular responses elicited with antigen binding to the extracellular CAR domain. The "effector function" refers to a specialized function of the cell. Effector function of a T cell may be cytolytic activity or activity including the secretion of cytokine. Consequently, in the present description an "intracellular signaling domain" refers to the portion of a protein which transduces the signal of the "effector function" which induces the cell to perform a specialized function. As described in the art, a complete intracellular signaling domain or a truncated portion of an intracellular signaling domain can be used. As will be understood by the skilled person, an effective truncated portion must transduces the effector function signal in substantially the same manner as the complete domain. Herein, the term "intracellular signaling domain" is meant to include any truncated portion of the intracellular signaling domain sufficient to transducing effector function signal.

In preferred embodiments of the invention, the CAR has a hinge region IgG1-CH2-CH3 (a first part of IgG1 is localized in the membrane and a second part of IgG1 is localized extracellularly outside the cell) and CD28 as transmembrane domain (a first part of CD28 is localized in the membrane and a second part of CD28 is localized intracellularly in the cytoplasm). CD8a may also be used as transmembrane domain and hinge region. Sequences derived from IgG4 may also be used.

As known from the art, signals generated through the T-Cell receptor (TCR) alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g. a TCR/CD3 complex) and co-stimulatory signaling domains that act in an antigen-independent manner to provide a secondary or any co-stimulatory signal. In preferred embodiments, the CAR of the invention comprises an intracellular signaling domain that comprises one or more "co-stimulatory signaling domain". Consequently, in other preferred embodiments, isolated nucleic acid molecules of the invention encode an intracellular signaling domain comprising at least one costimulatory domain, so that the resulting intracellular signaling domain therefore comprises at least one costimulatory domain.

As used herein, the term "co-stimulatory signaling domain" or "co-stimulatory domain", refers to an intracellular signaling domain of a co-stimulatory molecule. Co-stimulatory molecules are cell surface molecules other than antigen receptors or Fc receptors that provide a second signal required for efficient T cells activation/function when binding to the antigen.

In the present description, the terms "polypeptide", "polypeptide fragment", "peptide" and "protein" are used interchangeably and have, unless specified to the contrary, the conventional meaning, i.e. a sequence of amino acids. Polypeptides are not limited to a specific length and may comprise a full length protein sequence or a fragment thereof. The polymer can be linear or branched, it can comprise modified amino acids, and it can be interrupted by non-amino acids. Further, polypeptides may have post-translational modifications, e.g. disulfide bond formation, glycosylation, lipidation, acetylation, phosphorylation, or any other manipulation or modification, such as conjugation with a labeling component, and more generally any modification occurring naturally occurring and/or non-naturally. Given the fact that the polypeptides of this invention are based on antibodies, in some embodiments, the polypeptides can occur as single chains or associated chains. Polypeptides can be prepared using any technique known in the art, i.e. recombinant and/or synthetic techniques. More particularly, polypeptides described herein encompass the CARs of the present disclosure, or sequences that have deletions from, additions to, and/or substitutions of one or more amino acid of a CAR as disclosed herein.

An "isolated peptide" or an "isolated polypeptide" and the like, as used herein, refer to in vitro isolation and/or purification of a peptide or polypeptide molecule from a cellular environment, and from association with other components of the cell. Similarly, an "isolated cell" refers to a cell that has been obtained from an in vivo tissue or organ and is substantially free of extracellular matrix.

The term "vector" is used herein to refer to a nucleic acid molecule capable transferring or transporting another nucleic acid molecule. More generally, a "vector" means a construct, which is capable of delivering, and expressing, one or more gene(s) or sequence(s) of interest in a host cell. The nucleic acid that is to be transported or transferred is linked to the vector nucleic acid molecule in any way known in the art, e.g. by insertion. A vector may include sequences that direct autonomous replication in a cell, or may include sequences sufficient to allow integration into host cell DNA. The present invention also provides a vector comprising a nucleic acid molecule encoding the CAR of the invention. The vector may be selected from a DNA, a RNA, phage vector, a plasmid, a lentivirus vector, an adenoviral vector, or a retrovirus vector. The vector of the invention preferably comprises a promoter, such as an EF-1 alpha promoter. The term "promoter" as used herein refers to a recognition site of a polynucleotide (DNA or RNA) to which an RNA polymerase binds. As known by the skilled person, RNA polymerase initiates the transcription of the polynucleotides operably linked to the promoter. In a particular embodiment, it may be desirable to express a polynucleotide comprising a CAR from a promoter that provides stable and long-term CAR expression in T cells. A CAR expression under the control of a promoter further ensures sufficient expression levels to direct the T cells against cells expressing the target antigen.

Retroviruses are a common tool for gene delivery. In some embodiments, a retrovirus is used to deliver a polynucleotide encoding a chimeric antigen receptor (CAR) to a cell, preferentially an immune cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus". The provirus serves as a template for RNA polymerase and directs the expression of RNA molecules which encode the structural proteins and enzymes needed to produce new viral particles. As a consequence, T cells transduced with a vector of the invention can generate a stable, long-term, and persistent CAR-mediated T-cell response. In particular embodiments, the T cell is transduced with a lentiviral vector, i.e. lentivirus, encoding a CAR according to the present invention. The term "lentiviral vector" refers to a viral vector or plasmid containing structural and functional genetic elements, or portions thereof, including long terminal repeats (LTRs) that are primarily derived from a lentivirus. The term "lentivirus" refers to a group (or genus) of complex retroviruses. Well known lentiviruses include human immunodeficiency virus (HIV, e.g. type 1 or type 2); visna-maedi virus (VMV); the caprine arthritis-encephalitis virus (CAEV); equine infectious anemia virus (EIAV); feline immunodeficiency virus (FIV); bovine immune deficiency virus (BIV); and simian immunodeficiency virus (SIV). The term "self-inactivating"

(SIN) vectors refers to replication-defective vectors, e.g. retroviral or lentiviral vectors, in which the 3' LTR enhancer-promoter region, known as the U3 region, has been modified (for instance by deletion or substitution) to prevent viral transcription beyond the first round of viral replication.

The term "purified" and "isolated" it is meant, when referring to a molecule, such as a polypeptide or an antibody or a nucleotide sequence of the invention, that the indicated molecule is present in the absence of other biological macromolecules of the same type. More specifically the term "purified" as used herein in particular means at least 85%, 90%, 95% or 98% by weight, of biological macromolecules of the same type are present. More specifically the term "isolated" nucleic acid molecule that encodes a particular polypeptide refers to a nucleic acid molecule that is substantially free of other nucleic acid molecules that do not encode the subject polypeptide; however, the molecule may include some additional bases or moieties, which do not deleteriously affect the basic characteristics of the composition.

The term "antigen", "target" or "target antigen" refers to a molecule or a portion of a molecule that is capable of being bound by an antibody or an antibody-like binding protein. The term further refers to a molecule or a portion of a molecule that is capable of being used in an animal to produce antibodies that are capable of binding to an epitope of that antigen. A target antigen may have one or more epitopes. With respect to each target antigen recognized by an antibody or by an antibody-like binding protein, the antibody-like binding protein is capable of competing with an intact antibody that recognizes the target antigen.

The terms "CD123", "IL-3Ra" or "IL-3Ra", "Interleukine-3 Receptor alpha" or "Interleukine-3 Receptor a", are used interchangeably herein and refer to any native (human) IL-3Ra or CD123, unless otherwise indicated. The CD123 protein is an interleukin 3-specific subunit of a heterodimeric cytokine receptor (i.e. IL-3 Receptor or IL-3R). The IL-3R is comprised of a ligand specific alpha subunit, and a signal transducing common beta subunit (also known as CD131) shared by the receptors for interleukin 3 (IL3), colony stimulating factor 2 (CSF2/GM-CSF), and interleukin 5 (IL5). The binding of CD123/IL-3Ra to IL3 depends on the beta subunit. The beta subunit is activated by the ligand binding, and is required for the biological activities of IL3. All of these foregoing terms for CD123 can refer to either a protein or nucleic acid sequence as indicated herein. The term "CD123/IL-3Ra" encompasses "full-length" unprocessed CD123/IL-3Ra, as well as any form of CD123/IL-3Ra that results from processing within the cell. The term also encompasses naturally occurring variants of CD123/IL-3Ra protein or nucleic acid, e.g. splice variants, allelic variants and isoforms. The CD123/IL-3Ra polypeptides and polynucleotides described herein can be isolated from a variety of sources, such as from human tissue types or from another source, or prepared by recombinant or synthetic methods. Examples of CD123/IL-3Ra sequences include, but are not limited to protein and nucleic acid sequences for human CD123 variant 1,protein and nucleic acid sequences for human CD 123 variant 2.

The term "anti-CD123 antibody", "anti-IL-3Ra antibody" or "anti-IL-3Rα antibody", "an antibody that specifically binds to CD123" or "an antibody that specifically binds to IL-3Ra/IL-3Rα refers to an antibody that is capable of binding CD123 with sufficient affinity such that the antibody is useful as a diagnostic and/or therapeutic agent in targeting CD123. Unless otherwise specified, the extent of binding of an anti-CD 123 antibody to an unrelated, non-CD123 protein is less than about 10% of the binding of the antibody to CD123 measured. More generally, the term "specifically binds" designates that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B" or antibody "A" may be said to bind to epitope "C" with a higher specificity than it has for related epitope "D." Accordingly, an antibody or antigen-binding fragment of the invention specifically binds to a CD123 antigen, in that it has a higher binding specificity to the CD123 antigen (from any species) than that to a non-CD123 antigen. More particularly, an antibody or antigen-binding fragment of the invention specifically binds to a human CD 123 antigen, in that it has a higher binding specificity to the human CD123 antigen than that to a non-human CD123 antigen (e.g. a mouse or a rat CD123). Occasionally, the term "preferentially binds" designates that an antibody specifically binds to an epitope more readily than it would bind to a related, similar, homologous, or analogous epitope. Hence, an antibody which preferentially binds to a given epitope would more likely bind to that epitope than to a related epitope, even though such an antibody may cross-react with the related epitope. For example, an antibody or antigen-binding fragment of the invention may preferentially bind to a human CD123 antigen over a mouse CD123.

According to the above, terms related to an antibody, a CAR, a vector or a cell of the invention are easily derived. Indeed, the general context of the description does not always require to stick exact same wording as labeled above. Some deviation may occur. For example, when referring to a CAR of a T cell it is not always required to specify that the CAR comprises a part directed to a specific antigen. i.e. "anti-something". Accordingly, and on a more general note, a CAR of the present invention that comprises a part that specifically binds to CD123 may be referred to not only as anti-CD123 CAR but also as CD123 CAR. In the same manner, a T cell that is transduced with a CAR that specifically binds to CD123 according to the invention, may be referred to as CD123 CAR T cell.

A "treatment" as used herein includes any beneficial or desirable effect on the symptoms or pathology of a disease or pathological condition, and may include any reductions in one or more measurable markers of the disease or condition being treated, e.g. cancer. Treatment may comprise either the reduction of symptoms or any improvement regarding the symptoms a disease or condition. A treatment further may delay the progression of the disease or condition. Hence the term "treatment" does not necessarily means a complete eradication or cure of the disease or condition, or the associated symptoms thereof. With this in mind, the present invention disclosure provides for the treatment or prevention of BPDCN comprising administering to a subject in need thereof, a therapeutically effective amount of the T cells of the invention.

In this context, The T cells described herein may be administered either alone, or as a pharmaceutical composition (also called pharmaceutical formulation). The term "pharmaceutical composition" or "pharmaceutical formulation" refers to a preparation which is in such form as to permit the biological activity of the active ingredient to be effective, and which contains no additional components which are unacceptably toxic to a subject to which the composition/formulation would be administered. Such formulation can be sterile. Pharmaceutical compositions may comprise T cells according to the invention alone, or in combination with one or more pharmaceutically or physiologically acceptable carriers, diluents or excipients.

Such compositions may comprise buffers such as neutral buffered saline, phosphate buffered saline and the like; carbohydrates such as glucose, mannose, sucrose or dextran, mannitol; proteins; polypeptides or amino acids such as glycine; antioxidants; chelating agents such as EDTA or glutathione; adjuvants, and stabilizers. The terms "pharmaceutically acceptable" or "physiologically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Compositions of the present invention are preferably formulated for parenteral administration. A "parenteral administration" may refer to administration modes other than enteral and topical administration. Usually parenteral administration is done by injection, such as intravascular, intravenous, intramuscular, intra-arterial, intrathecal, intra-capsular, intra-orbital, intra-tumoral, intra-cardiac, intradermal, intraperitoneal, transtracheal, subcutaneous, subcuticular, intraarticular, subcapsular, subarachnoid, intraspinal and intrasternal injection and/or infusion. Preferentially, the CAR-modified T cells or the compositions of the invention are administered to a subject by direct injection into a tumor, lymph node, systemic circulation, or site of infection. Generally, the invention is useful to treat a subject diagnosed with a disease overexpressing CD123, particularly patients having BPDCN. The treatment comprises removing immune effector cells from the subject, genetically modifying said immune effector cells with a vector comprising a nucleic acid encoding a CAR as contemplated herein, thereby producing a population of modified immune effector cells, and administering the population of modified immune effector cells to the same subject. In a preferred embodiment, the immune effector cells are T cells. The quantity, frequency of the administration are determined with regard to the patient physical state (condition of the patient, the type and severity of the patient's disease). Appropriate dosages may also be determined with the help of animal models followed by clinical trials. When referring to dosages, the term "effective amount" is an amount sufficient to carry out a specifically stated purpose. The so called "therapeutically effective amount" of an active ingredient, such as a genetically modified T cell, may depend on factors such as the disease and its state, the age, sex, and weight of the patient, and further depend on the ability of the cells to induce the desired response in the patient. A therapeutically effective amount is also one in which any toxic or detrimental effects of the virus or transduced therapeutic cells are outweighed by the therapeutically beneficial effects. It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. More generally, the term "therapeutically effective amount" refers to an amount of an antibody, active ingredient or other drug effective for treating a disease or disorder in a subject. In the case of cancer, the therapeutically effective amount of the drug can reduce the number of cancer cells; reduce the tumor size; inhibit (i.e. slow down to some extent or stop the cancer) cancer cell infiltration into peripheral organs; inhibit (i.e. slow down to some extent or stop the cancer) tumor metastasis; inhibit to some extent or stop the tumor growth; relieve to some extent one or more of the symptoms associated with the cancer; and/or result in a favorable response such as increased progression-free survival (PFS), disease-free survival (DFS), or overall survival (OS), complete response (CR), partial response (PR), or, in some cases, stable disease (SD), a decrease in progressive disease (PD), a reduced time to progression (TTP), or any combination thereof. A "prophylactically effective amount" refers to an amount effective, at dosages and for periods of time necessary, to achieve the desired prophylactic result. Usually, the prophylactically effective amount is less than the therapeutically effective amount since a prophylactic dose is used in subjects prior to or at an earlier stage of disease.

In particular embodiments, prior to in vitro manipulation or genetic modification of the immune effector cells described herein, the source of cells is obtained from a subject. In particular embodiments, the immune effector cells expressing the CAR of the invention at its membrane comprise T cells. T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as FICOLL™ separation. In another embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. In other embodiments, T cells are isolated from peripheral blood mononuclear cells by lysing the red blood cells and depleting the monocytes, for example, by centrifugation through a PERCOLL™ gradient. A specific subpopulation of T cells, expressing one or several markers like CD3, CD4 or CD8 can be further isolated by positive or negative selection techniques. For example, enrichment of a T cell population by negative selection can be accomplished with a combination of antibodies directed to surface markers not expressed on the negatively selected cells.

In a more general context, the present description highlights a cellular therapy where T cells are genetically engineered (or genetically modified) ex-vivo to express a CAR and the CAR T cell is infused to a patient, preferably a human, in need thereof. The infused cell is able to kill tumor cells in the patient. As explained above, and unlike antibody therapies, T cells comprising a CAR are able to replicate in vivo resulting in long-term persistence that can lead to sustained tumor control. Moreover, CARs allow for the redirection and activation of effector T cells towards any cell surface molecule upon binding by the antibody derived receptor, and are independent of MHC restriction (MHC-restricted antigen recognition; MHC stands for Major Histocompatibility Complex). As mentioned above, genetically engineered T cells of the invention are constructed starting from T cells collected from the patient himself/herself (autologous), but they can also originate from other allogenic donors to provide allogenic genetically-engineered T cells in bone marrow or peripheral hematopoietic stem cell allograft context (Donor lymphocytes infusion). These T cells expressing a CAR molecule according to the invention are useful to treat a proliferative disease in a mammal, preferably a human.

In some embodiments of the invention, a polynucleotide or cell harboring the polynucleotide of the present invention uses a suicide gene, including an inducible suicide gene to reduce the risk of direct toxicity (i.e. Graft Versus Host Diseases in allogeneic administration, GvHD) and/or uncontrolled proliferation of gene modified cells. In specific aspects, the suicide gene is not immunogenic to the host harboring the polynucleotide or cell. A certain example of a suicide gene that may be used is inducible caspase-9 (iCASP9), thymidine kinase d'Herpes simplex (HSV-tk), CD20, truncated EGFR, caspase-8 or cytosine deaminase. Caspase-9 can be activated using a specific chemical inducer of dimerization (CID). Others systems may be activated by metabolizing prodrugs (Ganciclovir), or by binding antibodies (Rituximab, Cetuximab).

The invention is further described in detail with reference to experimental data and specific examples. The examples are provided for purposes of illustration only, and are not intended to be limiting unless otherwise specified. While the following detailed description concentrates on BPDCN, the invention yet can generally provide improvement and/or solutions for any disease wherein a CD123 overexpression occurs.

A major focus of the present invention is to provide a treatment for Blastic Plasmacytoid Dendritic Cell Neoplasm (BPDCN).

BPDCN is a clonal disease derived from precursors of plasmacytoid dendritic cells (pDC) with skin lesions that progress to aggressive leukemic dissemination, cf. Blastic Plasmacytoid Dendritic Cell Neoplasm: State of the Art and Prospects, Maria Rosaria Sapienza, Alessandro Pileri, Enrico Derenzini, Federica Melle et al., Cancer, 2019. Prognosis for BPDCN is poor and effective treatment or report thereon is non-existent in the art. Most patients first respond to intensive chemotherapy, but then relapse. The median overall survival (OS) in the largest patient series ranging from 8 to 12 months. The only exceptions to that data are relative to patients who underwent allogenic hematopoietic stem cell transplantation (allo-HSCT); cf. Roos-Weil D, Dietrich S, Boumendil A, Polge E, Bron D, Carreras E, et al., Stem cell transplantation can provide durable disease control in blastic plasmacytoid dendritic cell neoplasm: a retrospective study from the European Group for Blood and Marrow Transplantation, Blood, 2013, 121(3): 440-6; Pagano L, Valentini C G, Grammatico S, Pulsoni A, Blastic plasmacytoid dendritic cell neoplasm: diagnostic criteria and therapeutical approaches, British journal of haematology, 2016, 174(2):188-202; Kharfan-Dabaja M A, Lazarus H M, Nishihori T, Mahfouz R A, Hamadani M. Diagnostic and therapeutic advances in blastic plasmacytoid dendritic cell neoplasm: a focus on hematopoietic cell transplantation, Biology of blood and marrow transplantation journal of the American Society for Blood and Marrow Transplantation, 2013; 19(7):1006-12; and even in patients treated by targeted therapies (Pemmaraju N, Lane A A, Sweet K L, Stein A S, Vasu S, Blum W, et al., Tagraxofusp in Blastic Plasmacytoid Dendritic-Cell Neoplasm, The New England journal of medicine, 2019; 380(17):1628-37). However, most elderly patients are not eligible for this approach. Improved treatments are needed for this leukemia that one can qualify as chemotherapy-refractory leukemia.

The Applicant of the present invention has identified new therapeutic targets. The Interleukin (IL) 3 receptor alpha chain (CD123) has proven to be a valuable target since it is highly expressed in the organism only by basophils and pDC. The art further discloses that CD123 is also expressed at a low level in normal hematopoietic CD34+ CD38+ progenitors, monocytes and endothelial cells but not on hematopoietic stem cells; cf.

Taussig D C, Pearce D J, Simpson C, Rohatiner A Z, Lister T A, Kelly G, et al. Hematopoietic stem cells express multiple myeloid markers: implications for the origin and targeted therapy of acute myeloid leukemia, Blood. 2005; 106(13):4086-92; cf. Adhra A1-Mawalil, David Gillis and Ian Lewis, Immunoprofiling of leukemic stem cells CD34+/CD38−/CD123+ delineate FLT3/ITD-positive clones, Journal of Hematology & Oncology, 2016, 9:61.

To fight BPDCN, the inventors have generally considered that the antigen CD123 is homogeneously and highly expressed in BPDCN at both diagnosis and in cases of relapse after chemotherapy; cf. Garnache-Ottou F, Feuillard J, Ferrand C, Biichle S, Trimoreau F, Seilles E, et al., Extended diagnostic criteria for plasmacytoid dendritic cell leukaemia, British journal of haematology, 2009; 145(5): 624-36. Further, the inventors considered that CD123 is a component of the IL-3 receptor and that the IL-3 receptor is a key driver of pDC lineage that is need by pDC cells survival Broughton S E, Dhagat U, Hercus T R, Nero T L, Grimbaldeston M A, Bonder C S, et al., The GM-CSF/IL-3/IL-5 cytokine receptor family: from ligand recognition to initiation of signaling. Immunological reviews. 2012; 250 (1):277-302; Hara T, Miyajima A., Function and signal transduction mediated by the interleukin 3 receptor system in hematopoiesis, Stem Cells, 1996, 14(6):605-18; and Testa U, Pelosi E, Frankel A., CD 123 is a membrane biomarker and a therapeutic target in hematologic malignancies, Biomarker research, 2014, 2(1):4. The inventors postulated that targeting this IL-3 receptor may induce deleterious signaling pathways for BPDCN cells.

It has been reported that CD123 participates in blast priming in acute myeloid leukemia (AM and acute lymphoid leukemia (ALL); cf. Ehninger A, Kramer M, Rollig C, Thiede C, Bornhauser M, von Bonin M, et al., Distribution and levels of cell surface expression of CD33 and CD123 in acute myeloid leukemia, Blood cancer journal, 2014, 4:e218. Further, it has been reported that CD123 is expressed on the CD34+ "leukemia initiating cells (LICs)" component and is associated with adverse clinical impact; cf. Vergez F, Green A S, Tamburini J, Sarry J E, Gaillard B, Cornillet-Lefebvre P, et al., High levels of CD34+ CD38low/-CD123+ blasts are predictive of an adverse outcome in acute myeloid leukemia: a Groupe Ouest-Est des Leucemies Aigues et Maladies du Sang (GOELAMS) study, Haematologica, 2011, 96(12):1792-8; and Reya T, Morrison S J, Clarke M F, Weissman I L, Stem cells, cancer, and cancer stem cells, Nature, 2001, 414(6859):105-11. However, in BPDCN, it is unknown if an increased number of immature LICs are present in patients. The Applicant yet surprisingly observed that, in specific BPDCN cases that were collected by the inventors, a low component of blastic cells express a higher level of CD123 than the leukemic bulk cells do. The applicant then further postulated that in the event that if they are LIC, targeting CD123 might eliminate these cells and reduce relapse in BPDCN patients. The Applicant then actively selected CD123 as a target immunotherapy for BPDCN.

The Applicant further demonstrated sensitivity of BPDCN cells to SL-401 which is a fusion protein comprising diphtheria toxin coupled to IL-3 that targets cells expressing CD123 in vitro and in vivo; cf. Angelot-Delettre F, Roggy A, Frankel A E, Lamarthee B, Seilles E, Biichle S, et al., In vivo and in vitro sensitivity of blastic plasmacytoid dendritic cell neoplasm to SL-401, an interleukin-3 receptor targeted biologic agent, Haematologica, 2015; 100(2):223-30. Also, clinical responses have been reported in BPDCN patients; cf. Frankel A E, Woo J H, Ahn C, Pemmaraju N, Medeiros B C, Carraway H E, et al., Activity of SL-401, a targeted therapy directed to interleukin-3 receptor, in blastic plasmacytoid dendritic cell neoplasm patients, Blood, 2014; 124(3):385-92.

As known from the art, adoptive T-cell therapy using chimeric antigen receptor (CAR) is a promising way to treat hematologic malignancies with a risk to relapse; cf. Grupp S A, Kalos M, Barrett D, Aplenc R, Porter D L, Rheingold S R, et al., Chimeric antigen receptor-modified T cells for acute lymphoid leukemia, The New England journal of medicine, 2013; 368(16):1509-18; and Kochenderfer J N, Dudley M E, Kassim S H, Somerville R P, Carpenter R O, Stetler-Stevenson M, et al., Chemotherapy-refractory diffuse large B-cell lymphoma and indolent B-cell malignancies can be effectively treated with autologous T cells expressing an anti-CD19 chimeric antigen receptor, Journal of clinical oncology: official journal of the American Society of Clinical Oncology, 2015; 33(6):540-9.

According to an embodiment of the present invention, a CAR has been genetically engineered to be made of a single chain variable fragment (ScFv) of heavy and light chains of a monoclonal antibody (MAb) linked to the intracellular signaling chain of a T cell receptor (TCR). Preferably, the intracellular part the CAR comprises a CD3ζ and costimulatory domains such as CD28 and 4-1BB that enable better activation and cell signaling. The CAR can be qualified as a third generation CAR. For more details on CAR: see the review of Andrew D. Fesnak, Carl H. June and Bruce L. Levine, Engineered T cells: the promise and challenges of cancer immunotherapy, Nature, vol. 16, sept. 2016. The ScFV allows the recognition of an antigen independently of major histocompatibility complex (MHC) presentation.

Reports have been made on the efficiency of CAR CD123 in eradicating Acute Myeloid Leukemia in vitro and in several murine patient-derived xenograft models (PDX); cf. Mardiros A, Dos Santos C, McDonald T, Brown C E, Wang X, Budde L E, et al., T cells expressing CD123-specific chimeric antigen receptors exhibit specific cytolytic effector functions and antitumor effects against human acute myeloid leukemia, Blood, 2013, 122(18):3138-48; Gill S, Tasian S K, Ruella M, Shestova O, Li Y, Porter D L, et al., Preclinical targeting of human acute myeloid leukemia and myeloablation using chimeric antigen receptor-modified T cells, Blood, 2014, 123(15):2343-54; Thokala R, Olivares S, Mi T, Maiti S, Deniger D, Huls H, et al., Redirecting Specificity of T cells Using the Sleeping Beauty System to Express Chimeric Antigen Receptors by Mix-and-Matching of VL and VH Domains Targeting CD123+ Tumors, PloS one, 2016, 11(8):e0159477; Cummins K D, Gill S. Anti-CD123 chimeric antigen receptor T-cells (CART): an evolving treatment strategy for hematological malignancies, and a potential ace-in-the-hole against antigen-negative relapse, Leukemia & lymphoma, 2018, 59(7):1539-53; Tettamanti S, Marin V, Pizzitola I, Magnani C F, Giordano Attianese G M, Cribioli E, et al., Targeting of acute myeloid leukaemia by cytokine-induced killer cells redirected with a novel CD123-specific chimeric antigen receptor, British journal of haematology, 2013, 161(3):389-401; and Tasian S K, Kenderian S S, Shen F, Ruella M, Shestova O, Kozlowski M, et al., Optimized depletion of chimeric antigen receptor T cells in murine xenograft models of human acute myeloid leukemia, Blood, 2017; 129(17):2395-407. Another group showed that CAR CD123 could be active against an established BPDCN cell line (CAL-1) and $CD123^{+}$ primary BPDCN samples in mouse models. But this CAR is only used in an allogenic context. It is further of second generation with a suicide system; cf. Cai T, Galetto R, Gouble A, Smith J, Cavazos A, Konoplev S, et al., Pre-Clinical Studies of Anti-CD123 CAR-T Cells for the Treatment of Blastic Plasmacytoid Dendritic Cell Neoplasm (BPDCN), Blood. 2016, 128(22): 4039. However, growing clinical trials show that patients under CAR therapy develop toxicity. This is a major problem in the development of efficient CARs. The Applicant developed a specific CAR that overcomes the problems of the prior art. More particularly, the Applicant engineered both third generation retroviral and lentiviral CARs. The CARs of the invention overcome the problems of the prior art, and particularly those related to cytotoxicity. The CARs of the invention have improved functional activity on BPDCN cells (BPDCN cells lines, PDX cells and primary BPDCN cells) in vitro as in vivo in several mice models of BPDCN. The evaluation of their potential cytotoxicity on $CD123^{low}$ positive cells are surprisingly promising.

According to the invention, monoclonal antibodies (Mab) directed against human CD123 were produced. The monoclonal antibodies of the invention can be used in both allogenic and autologous context.

The production method of the Anti-CD123 monoclonal antibodies included immunization of mouse with recombinant CD123 protein. More specifically, five mice were immunized with the recombinant CD123 available under the reference #301-R3-025, available at R&D Systems, Minnesota, USA). Immunization was carried out by footpad and/or intraperitoneal administration. Lymph-nodes and/or splenic B cells were used to produce hybridomas secreting Mab. Hybridomas were selected based on the affinity and specificity of MAbs using $CD123^{+}$ and $CD123^{-}$ cell lines.

According to the invention, six specific antibodies were selected and respectively named 18B4D5 (also referred herein as AB1, or sometimes abbreviated as B4D5), 17F7B2 (also referred herein as AB2), 11B6E6 (also referred herein as AB3), 14G12D7 (also referred herein as AB4), 11A12C6 (also referred herein as AB5) and 15E11B7 (also referred herein as AB6). Molecular characterization and DNA sequencing has been made according to SANGER method.

VDJ and VJ gene rearrangements were sequenced and identified after alignment of consensus nucleotide sequences against the IMGT® database using the VQUEST online tool; cf. Brochet X, Lefranc M P, Giudicelli V. IMGT/V-QUEST: the highly customized and integrated system for IG and TR standardized V-J and V-D-J sequence analysis, Nucleic acids research, 2008; 36(Web Server issue):W503-8. Respective sequences (nucleotide sequences and amino acid sequences) of the six antibodies of the invention are listed in FIGS. 1 to 9.

FIG. 1 shows the nucleotide sequence and the amino acid sequence of complementary determining region 1 (CDR1), complementary determining region 2 (CDR2) and complementary determining region 3 (CDR3) of both the heavy chain and the light chain of the antibodies of the invention 18B4D5, 17F7B2, 11B6E6, 14G12D7, 11A12C6 and 15E11B7 respectively. The figure shows nucleotide sequences encoding CDR1 of the heavy chain of the antibodies 18B4D5 (SEQ ID NO: 158), 17F7B2 (SEQ ID NO: 159), 11B6E6 (SEQ ID NO: 160), 14G12D7 (SEQ ID NO: 161), 11A12C6 (SEQ ID NO: 162) and 15E11B7 (SEQ ID NO: 163) and the corresponding amino acid sequences 18B4D5 (SEQ ID NO: 25), 17F7B2 (SEQ ID NO: 27), 11B6E6 (SEQ ID NO: 29), 14G12D7 (SEQ ID NO: 31), 11A12C6 (SEQ ID NO: 33) and 15E11B7 (SEQ ID NO: 35); the nucleotide sequences encoding CDR1 of the light chain of the antibodies 18B4D5 (SEQ ID NO: 170), 17F7B2 (SEQ ID NO: 171), 11B6E6 (SEQ ID NO: 172), 14G12D7 (SEQ ID NO: 173), 11A12C6 (SEQ ID NO: 174) and 15E11B7 (SEQ ID NO: 175) and the corresponding amino acid sequences 18B4D5 (SEQ ID NO: 26), 17F7B2 (SEQ ID NO: 28), 11B6E6 (SEQ ID NO: 30), 14G12D7 (SEQ ID NO: 32), 11A12C6 (SEQ ID NO: 34) and 15E11B7 (SEQ ID NO: 36. The figure also shows nucleotide sequences encoding CDR2 of the heavy chain of the antibodies 18B4D5 (SEQ ID NO: 152), 17F7B2 (SEQ ID NO: 153), 11B6E6 (SEQ ID NO: 154), 14G12D7 (SEQ ID NO: 155), 11A12C6 (SEQ ID NO: 156) and 15E11B7 (SEQ ID NO: 157) and the corresponding amino acid sequences 18B4D5 (SEQ ID NO: 13), 17F7B2 (SEQ ID NO: 15), 11B6E6 (SEQ ID NO: 17), 14G12D7 (SEQ ID NO: 19), 11A12C6 (SEQ ID NO: 21) and 15E11B7 (SEQ ID NO: 23); the nucleotide sequences encoding CDR2 of the light chain of the antibodies 18B4D5, 17F7B2, 11B6E6, 14G12D7, 11A12C6 and 15E11B7, and the corresponding amino acid sequences 18B4D5 (SEQ ID NO: 14), 17F7B2 (SEQ ID NO: 16), 11B6E6 (SEQ ID NO: 18), 14G12D7 (SEQ ID NO: 20), 11A12C6 (SEQ ID NO: 22) and 15E11B7 (SEQ ID NO: 24. The further figure shows nucleotide sequences encoding CDR3 of the heavy chain of the antibodies 18B4D5 (SEQ ID NO: 146), 17F7B2 (SEQ ID NO: 147), 11B6E6 (SEQ ID NO: 148), 14G12D7 (SEQ ID NO: 149), 11A12C6 (SEQ ID NO: 150) and 15E11B7 (SEQ ID NO: 151) and the corresponding amino acid sequences 18B4D5 (SEQ ID NO: 1), 17F7B2 (SEQ ID NO: 3), 11B6E6 (SEQ ID NO: 5), 14G12D7 (SEQ ID NO: 7), 11A12C6 (SEQ ID NO: 9) and 15E11B7 (SEQ ID NO: 11); the nucleotide sequences encoding CDR2 of the light chain of the antibodies 18B4D5 (SEQ ID NO: 164), 17F7B2 (SEQ ID NO: 165), 11B6E6 (SEQ ID NO: 166), 14G12D7 (SEQ ID NO: 167), 11A12C6 (SEQ ID NO: 168) and 15E11B7 (SEQ ID NO: 169), and the corresponding amino acid sequences 18B4D5 (SEQ ID NO: 2), 17F7B2 (SEQ ID NO: 4), 11B6E6 (SEQ ID NO: 6), 14G12D7 (SEQ ID NO: 8), 11A12C6 (SEQ ID NO: 10) and 15E11B7 (SEQ ID NO: 12).

FIG. 2 shows the nucleotide sequence and the amino acid sequence of framework region 1 (FR1), framework region 2 (FR2), framework region 3 (FR3) and framework region 4 (FR4) of the heavy chain of the antibodies of the invention 18B4D5, 17F7B2, 11B6E6, 14G12D7, 11A12C6 and 15E11B7 respectively. The figure shows nucleotide sequences encoding FR1 of the heavy chain of the antibodies 18B4D5 (SEQ ID NO: 98), 17F7B2 (SEQ ID NO: 99), 11B6E6 (SEQ ID NO: 100), 14G12D7 (SEQ ID NO: 101), 11A12C6 (SEQ ID NO: 102) and 15E11B7 (SEQ ID NO: 103) and the corresponding amino acid sequences 18B4D5 (SEQ ID NO: 37), 17F7B2 (SEQ ID NO: 41), 11B6E6 (SEQ ID NO: 45), 14G12D7 (SEQ ID NO: 49), 11A12C6 (SEQ ID NO: 53) and 15E11B7 (SEQ ID NO: 57).The figure shows nucleotide sequences encoding FR2 of the heavy chain of the antibodies 18B4D5 (SEQ ID NO: 104), 17F7B2 (SEQ ID NO: 105), 11B6E6 (SEQ ID NO: 106), 14G12D7 (SEQ ID NO: 107), 11A12C6 (SEQ ID NO: 108) and 15E11B7 (SEQ ID NO: 109) and the corresponding amino acid sequences 18B4D5 (SEQ ID NO: 38), 17F7B2 (SEQ ID NO: 42), 11B6E6 (SEQ ID NO: 46), 14G12D7 (SEQ ID NO: 50), 11A12C6 (SEQ ID NO: 54) and 15E11B7 (SEQ ID NO: 58). The also figure shows nucleotide sequences encoding FR3 of the heavy chain of the antibodies 18B4D5 (SEQ ID NO: 110), 17F7B2 (SEQ ID NO: 111), 11B6E6 (SEQ ID NO: 112), 14G12D7 (SEQ ID NO: 113), 11A12C6 (SEQ ID NO: 114) and 15E11B7 (SEQ ID NO: 115) and the corresponding amino acid sequences 18B4D5 (SEQ ID NO: 39), 17F7B2 (SEQ ID NO: 43), 11B6E6 (SEQ ID NO: 47), 14G12D7 (SEQ ID NO: 51), 11A12C6 (SEQ ID NO: 55) and 15E11B7 (SEQ ID NO: 59). The figure further shows nucleotide sequences encoding FR4 of the heavy chain of the antibodies 18B4D5 (SEQ ID NO: 116), 17F7B2 (SEQ ID NO: 117), 11B6E6 (SEQ ID NO: 118), 14G12D7 (SEQ ID NO: 119), 11A12C6 (SEQ ID NO: 120) and 15E11B7 (SEQ ID NO: 121) and the corresponding amino acid sequences 18B4D5 (SEQ ID NO: 40), 17F7B2 (SEQ ID NO: 44), 11B6E6 (SEQ ID NO: 48), 14G12D7 (SEQ ID NO: 52), 11A12C6 (SEQ ID NO: 56) and 15E11B7 (SEQ ID NO: 60).

FIG. 3 shows the nucleotide sequence and the amino acid sequence of framework region 1 (FR1), framework region 2 (FR2), framework region 3 (FR3) and framework region 4 (FR4) of the light chain of the antibodies of the invention 18B4D5, 17F7B2, 11B6E6, 14G12D7, 11A12C6 and 15E11B7 respectively. The figure shows nucleotide sequences encoding FR1 of the light chain of the antibodies 18B4D5 (SEQ ID NO: 122), 17F7B2 (SEQ ID NO: 123), 11B6E6 (SEQ ID NO: 124), 14G12D7 (SEQ ID NO: 125), 11A12C6 (SEQ ID NO: 126) and 15E11B7 (SEQ ID NO: 127) and the corresponding amino acid sequences 18B4D5 (SEQ ID NO: 61), 17F7B2 (SEQ ID NO: 65), 11B6E6 (SEQ ID NO: 69), 14G12D7 (SEQ ID NO: 73), 11A12C6 (SEQ ID NO: 77) and 15E11B7 (SEQ ID NO: 81). The figure also shows nucleotide sequences encoding FR2 of the light chain of the antibodies 18B4D5 (SEQ ID NO: 128), 17F7B2 (SEQ ID NO: 129), 11B6E6 (SEQ ID NO: 130), 14G12D7 (SEQ ID NO: 131), 11A12C6 (SEQ ID NO: 132) and 15E11B7 (SEQ ID NO: 133) and the corresponding amino acid sequences 18B4D5 (SEQ ID NO: 62), 17F7B2 (SEQ ID NO: 66), 11B6E6 (SEQ ID NO: 70), 14G12D7 (SEQ ID NO: 74), 11A12C6 (SEQ ID NO: 78) and 15E11B7 (SEQ ID NO: 82). The figure further shows nucleotide sequences encoding FR3 of the light chain of the antibodies 18B4D5 (SEQ ID NO: 134), 17F7B2 (SEQ ID NO: 135), 11B6E6 (SEQ ID NO: 136), 14G12D7 (SEQ ID NO: 137), 11A12C6 (SEQ ID NO: 138) and 15E11B7 (SEQ ID NO: 139) and the corresponding amino acid sequences 18B4D5 (SEQ ID NO: 63), 17F7B2 (SEQ ID NO: 67), 11B6E6 (SEQ ID NO: 71), 14G12D7 (SEQ ID NO: 75), 11A12C6 (SEQ ID NO: 79) and 15E11B7 (SEQ ID NO: 83). The figure shows nucleotide sequences encoding FR4 of the light chain of the antibodies 18B4D5 (SEQ ID NO: 140), 17F7B2 (SEQ ID NO: 141), 11B6E6 (SEQ ID NO: 142), 14G12D7 (SEQ ID NO: 143), 11A12C6 (SEQ ID NO: 144) and 15E11B7 (SEQ ID NO: 145) and the corresponding amino acid sequences 18B4D5 (SEQ ID NO: 64), 17F7B2 (SEQ ID NO: 68), 11B6E6 (SEQ ID NO: 72), 14G12D7 (SEQ ID NO: 76), 11A12C6 (SEQ ID NO: 80) and 15E11B7 (SEQ ID NO: 84).

FIG. 4 shows the consensus amino acid sequence of the light chain (SEQ ID NO: 86) and the consensus amino acid sequence of the heavy chain (SEQ ID NO: 85) of a first antibody AB1 of the invention named 18B4D5 or B4D5. Amino acids corresponding to the CDR1, CDR2 and CDR3 are respectively highlighted from left to right in reading order.

FIG. 5 shows the consensus amino acid sequence of the light chain (SEQ ID NO: 88) and the consensus amino acid sequence of the heavy chain (SEQ ID NO: 87) of a second antibody AB2 of the invention named 17F7B2. Amino acids corresponding to the CDR1, CDR2 and CDR3 are respectively highlighted from left to right in reading order.

FIG. 6 shows the consensus amino acid sequence of the light chain (SEQ ID NO: 90) and the consensus amino acid sequence of the heavy chain (SEQ ID NO: 89) of a third antibody AB3 of the invention named 11B6E6. Amino acids corresponding to the CDR1, CDR2 and CDR3 are respectively highlighted from left to right in reading order.

FIG. 7 shows the consensus amino acid sequence of the light chain (SEQ ID NO: 92) and the consensus amino acid sequence of the heavy chain (SEQ ID NO: 91) of a fourth antibody AB4 of the invention named 14G12D7. Amino acids corresponding to the CDR1, CDR2 and CDR3 are respectively highlighted from left to right in reading order.

FIG. 8 shows the consensus amino acid sequence of the light chain (SEQ ID NO: 94) and the consensus amino acid sequence of the heavy chain (SEQ ID NO: 93) of a fifth antibody AB5 of the invention named 11A12C6. Amino acids corresponding to the CDR1, CDR2 and CDR3 are respectively highlighted from left to right in reading order.

FIG. 9 shows the consensus amino acid sequence of the light chain (SEQ ID NO: 96) and the consensus amino acid sequence of the heavy chain (SEQ ID NO: 95) of a sixth antibody AB6 of the invention named 15E11B7. Amino acids corresponding to the CDR1, CDR2 and CDR3 are respectively highlighted from left to right in reading order.

Respective sequence homology for heavy chain VH and JH as well as for light chain VK and JK is shown in table 1

TABLE 1

Sequence homology of variable chains.

| Antibody | | Heavy Chain | | homologie | Light Chain | | homologie |
|---|---|---|---|---|---|---|---|
| AB1 | 18B4D5 | VH | VH 3-2*02* | 97.22 | VK | VK 4-74*01 | 96.1 |
| | | JH | JH2*01 | 89.13 | JK | JK 1*01 | 100 |
| AB2 | 17F7B2 | VH | VH 1-5*01* | 95.49 | VK | VK 1-110*01 | 98.9 8 |
| | | JH | JH 3*01 | 95.83 | JK | JK 4*01 | 100 |
| AB3 | 11B6E6 | VH | VH 2-9-2*01* | 97.89 | VK | VK 8-21*01 | 98.32 |
| | | JH | JH 4*01 | 98.15 | JK | JK 4*01 | 100 |
| AB4 | 14G12D7 | VH | VH 3-2*02 | 97.22 | VK | VK 4-57-1*01 | 98.23 |
| | | JH | JH 2*01 | 89.36 | JK | JK 2*01 | 100 |
| AB5 | 11A12C6 | VH | VH 2-9*01 | 98.25 | VK | VK 8-21*01 | 96.63 |
| | | JH | JH 1*01 | 100 | JK | JK 4*01 | 100 |
| AB6 | 15E11B7 | VH | VH 1-20*01 | 96.88 | VK | VK 3-12*01 | 96.22 |
| | | JH | JH 3*01 | 95.83 | JK | JK 2*01 | 100 |

Affinity of the antibodies of the invention to CD123 is tested on streptavidin biosensors. Herein, to determine $K_D$ values seven different concentrations of CD123 were used on immobilized antibodies of the invention. The results were analyzed according to the Octet system available at FortéBio.

Results of antibody affinity is shown in table 2.

TABLE 2

Antibody affinity.

| Loading Sample ID | Conc. (nM) | Response | KD (M) | kon (1/Ms) | Kdis (1/s) | Full R^2 |
|---|---|---|---|---|---|---|
| AB1 (18B4D5) | 50 | 0.6972 | <1.0E−12 | 1.22E+05 | <1.0E−07 | 0.9988 |
| AB1 (18B4D5) | 25 | 0.4202 | <1.0E−12 | 1.22E+05 | <1.0E−07 | 0.9988 |
| AB1 (18B4D5) | 12.5 | 0.2301 | <1.0E−12 | 1.22E+05 | <1.0E−07 | 0.9988 |

TABLE 2-continued

Antibody affinity.

| Loading Sample ID | Conc. (nM) | Response | KD (M) | kon (1/Ms) | Kdis (1/s) | Full R^2 |
|---|---|---|---|---|---|---|
| AB1 (18B4D5) | 6.25 | 0.12 | <1.0E−12 | 1.22E+05 | <1.0E−07 | 0.9988 |
| AB5 (11A12C6) | 12.5 | 0.4158 | <1.0E−12 | 3.26E+05 | <1.0E−07 | 0.9885 |
| AB5 (11A12C6) | 6.25 | 0.2815 | <1.0E−12 | 3.26E+05 | <1.0E−07 | 0.9885 |
| AB5 (11A12C6) | 3.13 | 0.1349 | <1.0E−12 | 3.26E+05 | <1.0E−07 | 0.9885 |
| AB3 (11B6E6) | 50 | 0.3164 | 9.368E−09 | 7.01E+04 | 6.57E−04 | 0.9973 |
| AB3 (11B6E6) | 25 | 0.1794 | 9.368E−09 | 7.01E+04 | 6.57E−04 | 0.9973 |
| AB3 (11B6E6) | 12.5 | 0.0895 | 9.368E−09 | 7.01E+04 | 6.57E−04 | 0.9973 |
| AB3 (11B6E6) | 6.25 | 0.0349 | 9.368E−09 | 7.01E+04 | 6.57E−04 | 0.9973 |
| AB4 (14G12D7) | 100 | 0.3965 | 8.843E−09 | 3.67E+04 | 3.25E−04 | 0.9986 |
| AB4 (14G12D7) | 50 | 0.2206 | 8.843E−09 | 3.67E+04 | 3.25E−04 | 0.9986 |
| AB4 (14G12D7) | 25 | 0.1342 | 8.843E−09 | 3.67E+04 | 3.25E−04 | 0.9986 |
| AB2 (17F7B2) | 50 | 0.5066 | 2.552E−09 | 3.46E+05 | 8.82E−04 | 0.9747 |
| AB2 (17F7B2) | 25 | 0.34 | 2.552E−09 | 3.46E+05 | 8.82E−04 | 0.9747 |

TABLE 2-continued

Antibody affinity.

| Loading Sample ID | Conc. (nM) | Response | KD (M) | kon (1/Ms) | Kdis (1/s) | Full R^2 |
|---|---|---|---|---|---|---|
| AB2 (17F7B2) | 12.5 | 0.2645 | 2.552E−09 | 3.46E+05 | 8.82E−04 | 0.9747 |
| AB2 (17F7B2) | 6.25 | 0.1486 | 2.552E−09 | 3.46E+05 | 8.82E−04 | 0.9747 |
| AB6 (15E11B7) | 25 | 0.3052 | 2.485E−09 | 3.32E+05 | 8.26E−04 | 0.9829 |
| AB6 (15E11B7) | 12.5 | 0.1552 | 2.485E−09 | 3.32E+05 | 8.26E−04 | 0.9829 |
| AB6 (15E11B7) | 6.25 | 0.0878 | 2.485E−09 | 3.32E+05 | 8.26E−04 | 0.9829 |

Cells used to work the present invention, and particularly those for the purposes of the examples and results herein were obtained from humans. More precisely, primary cells from BPDCN patients (DC-2008-713 and DC-2016-2791 collections) were used for CD123 expression evaluation, cytotoxicity assays and amplification of primary cells in NSG mice to produce PDXs (primary derived xenograft), cf. Philippe L. et al., Bortezomib as a new therapeutic approach for blastic plasmacytoid dendritic cell neoplasm. Haematologica, 2017. These cases have been characterized according to current recommendations for the diagnosis of BPDCN established by the Applicant, cf. Garnache-Ottou F, Feuillard J, Ferrand C, Biichle S, Trimoreau F, Seilles E, et al., Extended diagnostic criteria for plasmacytoid dendritic cell leukaemia, British journal of haematology, 2009, 145(5): 624-36 and Swerdlow, S.H., Campo, E., Harris, N.L., Jaffe, E. S., Pileri, S.A., Stein, H., Thiele, J., Arber, D.A., Hasserjian, R.P., Le Beau, M.M., Orazi, A. & Siebert, R. (2017) WHO classification of tumors of haematopoeitic and lymphoid tissues. In: WHO Classification of Tumors of Haematopoietic and Lymphoid Tissues. (ed. by Swerdlow, S.H., Campo, E., Harris, N.L., Jaffe, E. S., Pileri, S.A., Stein, H., Thiele, J., Arber, D.A., Hasserjian, R.P., Le Beau, M.M., Orazi, A. & Siebert, R.), pp. 98-106. IARC, Lyon, France. PDX cells P127B, P25B, CM60915, F13-CAL1 and F13-LAN were cultured in vitro in an appropriate culture medium. Two $CD123^+$ BPDCN cell lines (GEN 2.2 and CAL-1, Dr. Maeda, Nagasaki University, Japan) and $CD123^-$ cell lines (Daudi, Jurkat, HL-60, REH). K562 CD123 cell line were generated by lentiviral transduction to express CD123. To study CD123 expression, cells derived from normal blood (n=19) and bone marrow (n=4), acute leukemia (myeloid AML, n=3) and lymphoid (B-ALL, n=3; T-ALL, n=3) were obtained from healthy donor and/or patients. In the invention, to produce genetically modified T cells peripheral blood mononuclear cells (PBMCs) were used. The PBMCs were isolated by FicoLL™ gradient density centrifugation (using the commercially available FicoLL-PAQUE™) of healthy donors or cord blood samples that were collected at the French Blood Center (EFS B/FC, Besangon, France).

Unless indicated otherwise, statistical analysis herein are expressed in mean values. More particularly, results are expressed as mean [minimum-maximum]for MFI and MFIR and as means±standard deviations for all other results. All statistical analyses in the described embodiments were performed using GraphPad Prism 7 (GraphPad Software, San Diego, CA, USA). Comparisons between two groups were assessed by Student t test. Survival studies were assessed by Kaplan-Meier curves and the log-rank (Mantel-Cox) test.

Using flow cytometry, the profiles of CD123 expression on normal hematopoietic cells and BPDCN cells were tested. Using the antibody of the invention B4D5 (AB1) and a commercial antiCD123 antibody (6H6) the profile of CD123 expression in normal cells and BPDCN patient cells were determined. More precisely, normal blood and bone marrow cells, i.e. normal pDC (targeted with CD304), monocytes ($CD14^+$), lymphocytes ($CD45^{+high}/SSC^{low}$), granulocytes ($CD45^+$, $SSC^{high}$ and $FSC^{high}$) and CSH/progenitors ($CD34^+$) were compared to BPDCN patients cells ($CD45^{+low}$, $CD304^+$). The mean fluorescence intensity ratio (MFIR) was calculated by dividing the mean fluorescence intensity (MFI) of CD123 by the one of the isotype control mAb. Cells were considered positive for CD123 expression for a MFIR higher than 2; cf. Garand R, Robillard N., Immunophenotypic characterization of acute leukemias and chronic lymphoproliferative disorders: practical recommendations and classifications. Hematology and cell therapy, 1996; 38(6):471-86. CD123 is the highest on normal pDC and BPDCN (respectively 130.6 [118.4-146.8], n=5 and 136 [102.1-158.1], n=5). A low expression is detected on monocytes (20.7 [4.5-51.1], n=7) and CD34+ cells (23.7 [19.2-32.2], n=4) whereas Lymphocytes (1.4 [1-2.4], n=7) and polynuclear cells (1.1 [1.1-1.2], n=3) do not express CD123.

Figure 10:
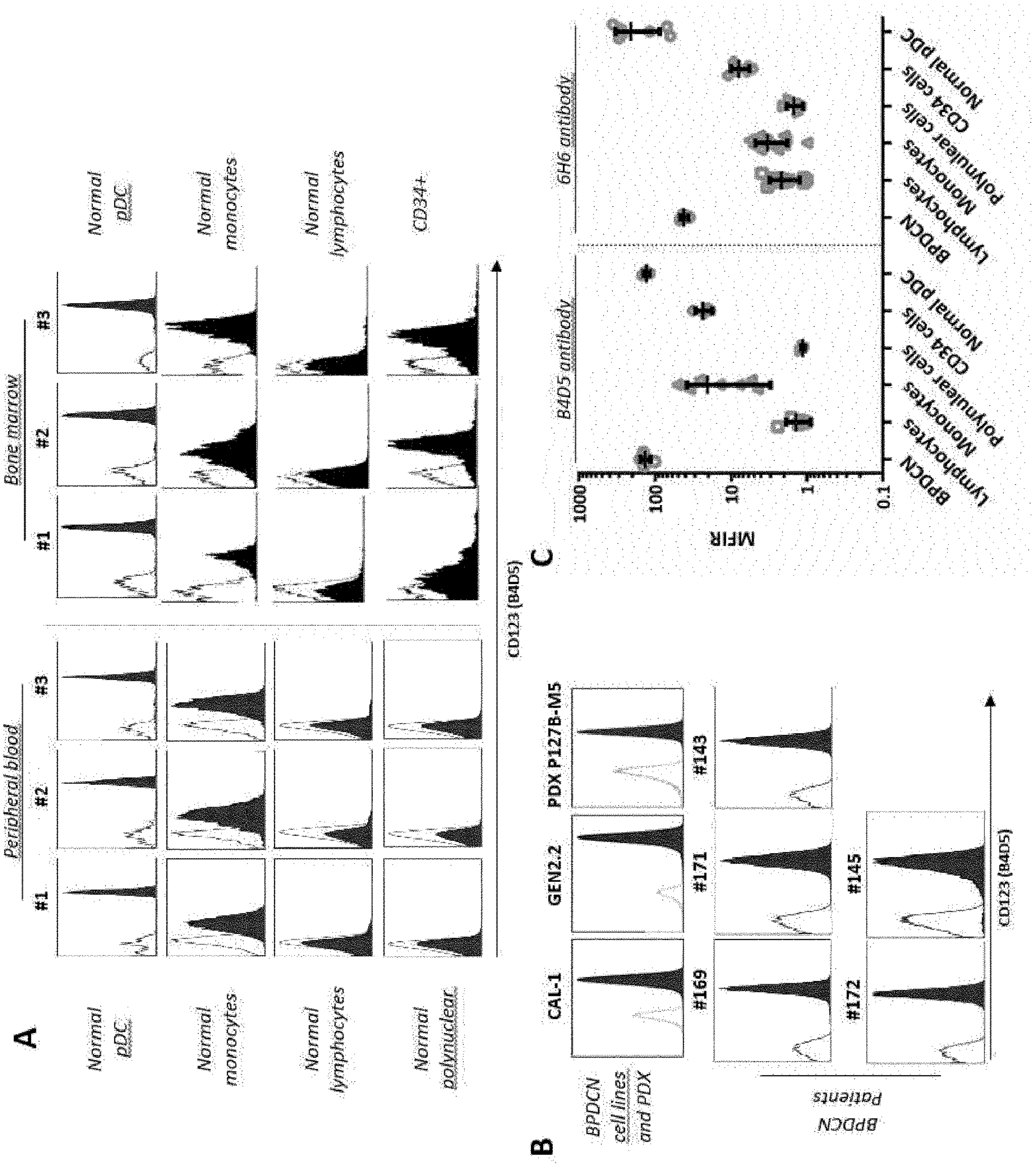
FIG. 10 shows flow cytometry graphs based on evaluation of CD123 expression on normal hematopoietic cells and BPDCN.

FIG. 10 shows flow cytometry graphs based on the evaluation of CD123 expression on normal hematopoietic cells and BPDCN. Particularly, shows flow cytometry graphs based on the evaluation of CD123 expression on normal hematopoietic cells and BPDCN using B4D5 antibody in comparison with a commercial antibody 6H6. Isotype control appear in white and antiCD123 B4D5 in dark. As mentioned above, normal cells were evaluated in peripheral blood and bone marrow, cf. FIG. 10 A, BPDCN cells lines (CAL-1 and GEN 2.2), PDX (Pl27B-M5) and primary cells of BPDCN patients, cf. FIG. 10 B. Further, CD123 expression evaluated by MFIR (ratio of mean fluorescence intensity of CD123 by the one of the isotype control mAb) using the antiCD123 B4D5 and 6H6 commercial antibodies on lymphocytes (n=7 and 12), monocytes (n=7 and 12), granulocytes (n=3 and 5), normal pDC (n=5 and 7). Expect for the CD34 population, data from blood and bone marrow samples (n=4 and 7) are pooled since we observe no difference of CD123 level expression, FIG. 10 C.

Further, some non-pDC acute leukemia were tested with the B4D5 monoclonal antibody. The Applicant confirmed that BPDCN express a higher level of CD123 than AML, B or T lymphoid acute leukemia tested.

Figure 11:
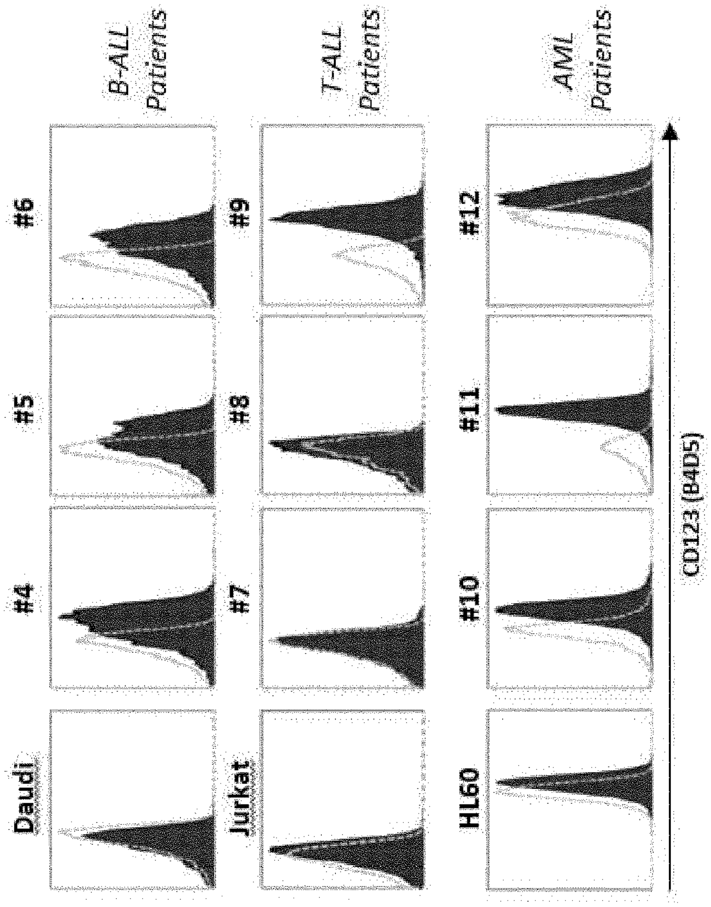
FIG. 11 shows a table and flow cytometry graphs based on evaluation of CD123 expression in BPDCN and other non-pDC acute leukemia.

FIG. 11 shows a table and flow cytometry graphs based on evaluation of CD123 expression in BPDCN and other non-pDC acute leukemia. FIG. 11 shows CD123 expression evaluated by MFIR (ratio of mean fluorescence intensity of CD123 divided by the one of the isotype control mAb) using the 6H6 commercial antibody on lymphocytes (n=12), monocytes (n=12), granulocytes (n=5), normal pDC (n=7), cf. FIG. 11 A. Data from blood and bone marrow samples are pooled since we observe no difference of CD123 level. Expression on the CD34 population is evaluated on bone marrow. FIG. 11 also shows the flow cytometry evaluation of CD123 expression on B-LAL, T-LAL and AML cells lines and patient primary cells using CD123 B4D5 antibody in dark, while the isotype control appears in white, cf. FIG. 11 B. The level of CD123 expression in non-pDC acute leukemia is lower than the one of BPDCN patients, cf. FIG. 11 B.

Figure 12:
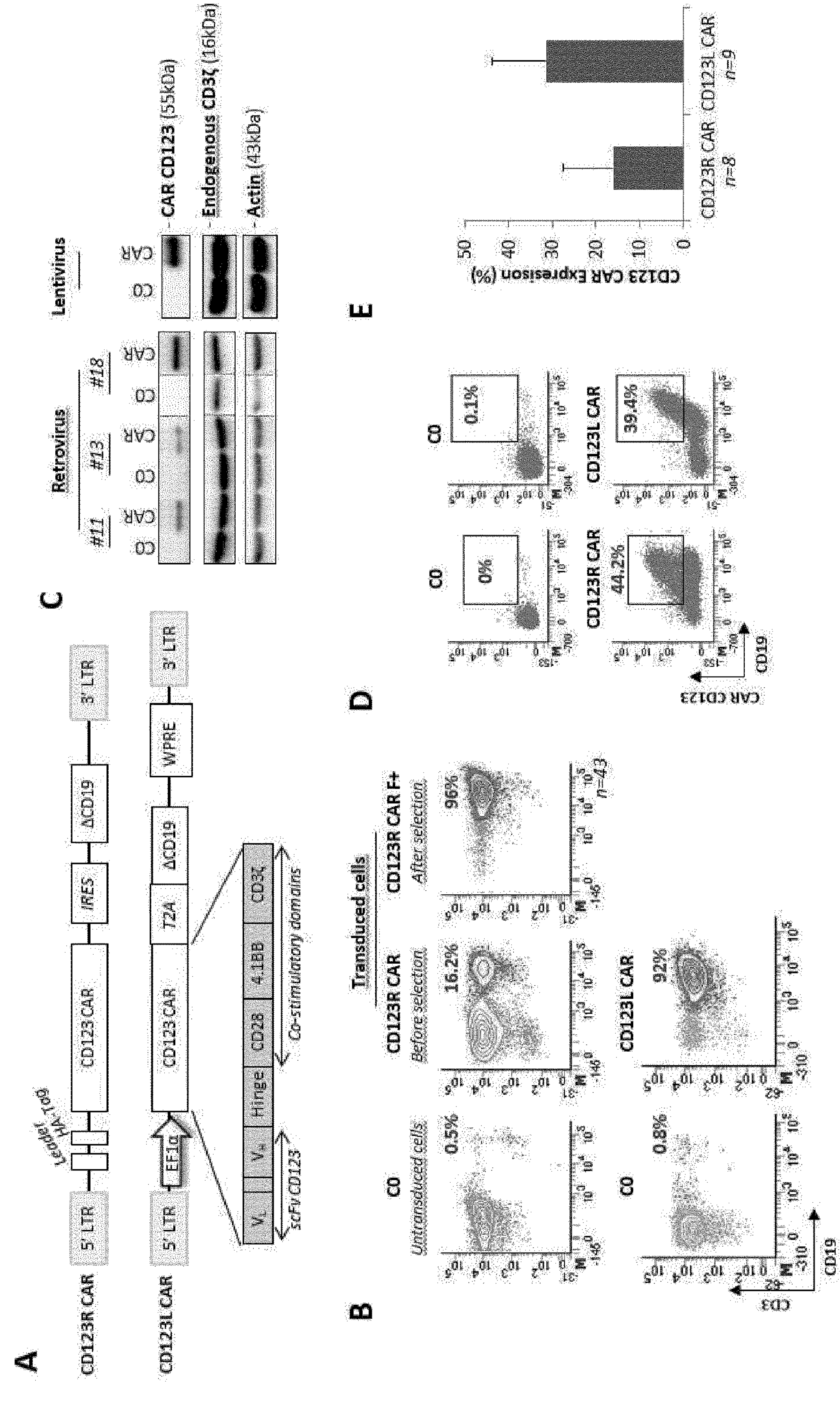
FIG. 12 shows a diagram of the design of a chimeric antigen receptor of the invention, a western blot and flow cytometry graphs relative to the production of a T cell according to the invention comprising the chimeric antigen receptor of the invention.

FIG. 12 shows a diagram of the design of a chimeric antigen receptor of the invention, a western blot and flow cytometry graphs relative to the production of a T cell according to the invention comprising the chimeric antigen receptor of the invention.

FIG. 12 shows the design and production of CD123 CAR T cells according to the invention. Using the antibody AB1 of the present invention an Anti-CD123 CAR T cell was constructed. The CAR of the present embodiment of the invention is based on the scFv of B4D5 (AB1), the specific domain of activation of T cells (CD3ζ) and two co-activation domains (CD28 and 4.1BB). The sequences encoding the CAR, a 2A sequence (encoding a 2A self-cleaving peptide) and the selection marker ΔCD19 (a truncated CD19) were cloned into a pSFG retroviral vector (SFG.CAR CD123.IRES.ΔCD19 vector). Retroviral supernatant was produced from a PG13 packaging cell line that had been transfected with the SFG.CAR CD123.IRES.ΔCD19 vector.

According to another embodiment of the invention, a lentiviral construct was also generated: the same CAR sequence is under control of EF1α promotor and downstream is a T2A ribosome skip sequence and a truncated human CD19 transduction marker.

Both the retroviral and the lentiviral embodiments are shown at FIG. 12 A. More precisely, item A of FIG. 12 shows a schematic diagram of the third generation retroviral anti-CD123 CAR vector (CD123R CAR) and the third generation lentiviral anti-CD123 CAR vector (CD123L CAR). The scFv CD123 derived from the B4D5 antibody of the invention is fused to T cell signaling domains CD28, 4.1BB and CD3ζ. The selection marker (ΔCD19) is also indicated.

Genetically modified primary T cells in the present invention were generated by viral transduction. PBMCs were activated with CD3/CD28 Dynabeads (Life Technologies, California, USA) for two days prior to transduction. Retroviral transduction is done in a 6-well-retronectin (1.2 pg/cm$^2$ in PBS overnight at 4° C., Takara, Japan)-coated plate. Cells were then spin-transduced (1.5 h, 2000 g, 10° C.) with the retroviral particles. For lentiviral transduction, cells were spin-transduced at 800 g, 32° C. for 1 h with MOI equals to 10. Transduction efficiency was determined by performing flow cytometric analysis to identify ΔCD19 cell surface marker expression on CD3$^+$ cells. Retro-transduced positive cells were magnetically labeled with microbeads (CD19 microbeads, Miltenyi Biotec, Bergisch Gladbach, Germany) and loaded onto a MACS® Column, according to the manufacturer's protocol. Transduced T cells will be named CD123R CAR for T cell obtained by retroviral transduction and CD123L CAR for lentiviral transduction. From the same donor, untransduced T cells (called C0) were gathered and cultured analogously to the above but without viral transduction: these cells are used as control in all experiments. CD123 CAR T-cells were expanded 21 days and cryopreserved.

For the purpose of the described embodiments of the invention, unless indicated otherwise, cytotoxicity can be evaluated based of BPDCN Patient derived transduced T cells. More particularly, T cells from BPDCN Patient (DC 2016-2791) are activated from PBMC using human CD3/CD28 Dynabeads and magnetic selection. The negative fraction contains BPDCN blast (60% on the blood cell differential count) that can be used to evaluated cytotoxicity of CAR and B lymphocytes. Further, T cells are transduced with lentiviral construct as previously described. After 10 days transduction efficiency and CAR expression is determined by flow cytometry as described. Cytotoxic activity was evaluated against BPCDN blast for 24 h with E:T ratio=5:1.

For the purpose of the described embodiments of the invention, unless indicated otherwise, immunophenotyping may be carried out as follows. Antibody binding is detected on a LSR Fortessa flow cytometer or BD FACS CANTO II and analyzed with Diva software (BD Biosciences, New Jersey, USA). Appropriately matched isotype controls are included for analysis. Briefly, T-cells are stained with CD3, CD4, CD8, CD19. CD3$^+$/CD19$^+$ T-cells are CD123 CAR T-cells. BPDCN cells, lines and PDX are characterized with CD123 staining using B4D5 (AB1 used for the CAR construction) and a commercial antibody (i.e. 6H6) to obtain more results. Normal blood and bone marrow samples are analyzed using anti CD45 (T cells are CD45$^{high}$/SSC$^{Low}$ and granulocytes are CD45$^+$/SSC$^{high}$/FSC$^{high}$), CD304 (normal pDC), CD14 (monocytes), and CD34 (CSH/progenitors). BPDCN samples from patients are stained with CD56, CD4, CD303, CD304, CD45. Some embodiments of the invention refer to a BPDCN mice model. Accordingly, in the BPDCN mice model, blast count (Anti-human hCD45, hCD123) and T cells (C0 and CD123 CAR) (hCD3, hCD19) are monitored weekly in blood cell samples using BD TRUCOUNT-tubes. In humanized mice, peripheral blood is analyzed by flow cytometry (Attune NxT Flow Cytometer, Life Technologies) to quantify human cells: total leucocytes (hCD45$^+$), monocytes (CD45/SSC$^{+medium}$, hCD33$^+$), B lymphocytes (hCD19$^+$), T lymphocytes (hCD3$^+$), pDC (hCD123$^+$, hCD304$^+$) and CSH/progenitors (CD34$^+$) in bone marrow after mice sacrifice. The monoclonal antibodies used to characterize cell surface phenotype are presented in Table 3.

TABLE 3

Monoclonal antibodies used to characterize cell surface phenotype.

| Fluo | Target | Provider | Ref | Cells targeted | Aim |
|---|---|---|---|---|---|
| VioBlue | CD3 | Milteniy Biotec | 130-114-519 | T-cells | T-cell characterization |
| APC | CD19 | Milteniy Biotec | 130-113-642 | CAR T-cells | |
| PE-Cy7 | CD4 | Sony Biotechnology | RT2387050 | T-cells | |
| FITC | CD8 | Sony Biotechnology | RT2323520 | T-cells | |
| V500 | CD45 | BDPharmingen | 560777 | ALL | Evaluation of CD123 expression on normal hematopoietic cells and BPDCN |
| V450 | CD34 | BDPharmingen | 345804 | AML | |
| PE-CY7 | CD123 | Biolegend | 306010 | ALL | |
| PERCP CY5.5 | CD33 | BDPharmingen | 333146 | AML | |
| APC | CD38 | BDPharmingen | 345807 | AML | |
| FITC | CD2 | Beckman Coulter | A07743 | T-ALL | |
| APC | CD3 | Beckman Coulter | IM2467 | T-ALL | |
| V450 | CD7 | BDPharmingen | 642916 | T-ALL | |
| FITC | CD10 | Beckman Coulter | A07759 | B-ALL | |
| APC | CD19 | Beckman Coulter | A07769 | B-ALL | |
| PERCE CY5.5 | CD22 | BDPharmingen | 563942 | B-ALL | |
| APC-H7 | CD4 | BDPharmingen | 560158 | BPDCN | |
| V450 | CD56 | BDPharmingen | 560360 | BPDEN | |

TABLE 3-continued

Monoclonal antibodies used to characterize cell surface phenotype.

| Fluo | Target | Provider | Ref | Cells targeted | Aim |
|---|---|---|---|---|---|
| APC | CD303 (BDCA-2) | Biolegend | 354206 | BPDCN | |
| APC | CD304 (BDCA-4) | Biolegend | 354506 | BPDEN | |
| APC-H7 | CD14 | BDPharmingen | 641394 | Monocytes | |
| BV711 | hCD45 | BDPharmingen | 304050 | Human cells | Evaluation the |
| FITC | mCD45 | BDPharmingen | 553080 | Murine cells | CAR CD123 |
| PerCP-Cy5.5 | CD33 | BDPharmingen | 333146 | Monocytes Granulocytes | toxicity of on normal |
| PE | BDCA4 /CD304 | Miltenyi Biotec | 130-111-893 | pDC | hematopoietic cells in in vivo |
| PE-Cy7 | CD123 | Sony Biotechnology | RT2130050 | pDC | model |
| APC | CD3 | Miltenyi Biotec | 130-11-135 | T cells | |
| APC-Vio770 | CD19 | Miltenyi Biotec | 130-113-643 | B cells | |
| FITC | CD38 | BDPharmingen | 555459 | CSH | |
| PE | mCD45 | Miltenyi Biotec | 130-110-797 | Murine cells | |
| BV421 | CD34 | BDPharmingen | 744904 | CSH | |
| BV421 | CD3 | BD Pharmingen | 562426 | T-cells | Memory T-cell |
| BV510 | CD8 | BD Pharmingen | 563919 | CAR T-cells | subset |
| APC | CD19 | Miltenyi Biotec | 130-091-248 | T-cells | |
| PE-CY | CD45RA | BD Pharmingen | 560675 | | |
| PERCP CY5.5 | CD45RO | BD Pharmingen | 560607 | T-cells | |
| FITC | CCR7 | R&D System | EAB197E-100 | | |
| PE | CD95 | BD Pharmingen | 555674 | T-cells | |

Some embodiments described herein further refer to in vitro cytotoxicity assays and functional analysis. For this, C0 or CD123 CAR T-cells ($1.10^6$ cells/mL) are labeled with Cell Proliferation Dye eFluor 450 (ThermoFischer, Ecublens, Switzerland) following manufacturer's protocol. Labeled cells are then cultured with appropriated effector to target (E:T) ratio with target cells (CAL-1, GEN 2.2, DAUDI, HL-60, K562 CD123 and PDX) at 37° C. for 24 h or 15 h (PDX). After co-culture, cells are labeled with 7-AAD (Beckman Coulter), anti-CD3, anti-CD19 (to evaluate C0 or CAR T cells) and anti-CD123 in order to evaluate cell death of target cells ($7\text{-AAD}^+$ $CD123^+$ cells). Functional propriety of CD123 CAR T cells are tested in vitro for CD107aPE degranulation assays (Clone H4A3, BD Biosciences) and $IFN\gamma^{PE}$ intracellular production (clone B27, BD Biosciences) are performed according manufacturer's protocol using BD Cytofix/Cytoperm™ Plus Fixation/Permeabilization Solution Kit with BD GolgiPlug™ (BD Biosciences). Co-culture supernatants are analyzed by CBA Human Th1/Th2/Th17 Cytokine Kit (BD Biosciences) according to the manufacturer's protocol. CAR cytotoxicity against HMEC adherent cell line or primary monocytes is evaluated using MTT Cell Proliferation test (Sigma-Aldrich, Missouri, USA) according to the manufacturer's protocol.

Some embodiments described herein further refer to tissue Micro Array and immunohistochemistry. Specificity of the B4D5 (AB1) antibody is analyzed by Tissue MicroArray including 90 tissue cores (30 organs) of three individual donors per organ (US Biomax, Rockville, United States). Immunostaining is detected using UltraView Universal DAB Detection Kit (Ventana, USA) and images are analyzed with NDP.view 2 software. The staining intensity is graduated as follows: negative (0), weak staining (1+), moderate staining (2+), or positive staining (3+), strong staining (4+). High CD123 (CAL-1) or negative (Daudi) expressing cell lines are respectively used as positive or negative controls. For each tissue that demonstrated a CD123 staining (colon, stomach, muscle, esophagus, skin and thyroid gland), CD123 expression is controlled by immunohistochemistry (IHC) on paraffin-embedded normal tissues from three patients and compared to skin from two BPDCN patients.

Further, some embodiments described herein refer to in vivo models to evaluate CAR CD123 efficiency. For this, NOD/SCID/IL2Rγc-deficient (NSG) mice (6-8 weeks of age, The Jackson laboratory, Sacramento, CA, USA) are irradiated (2.5 Gy) and inoculated intravenously with appropriated number of luciferase expressing CAL-1 ($1\text{-}10^6$/mouse) or PDX cells ($2\cdot10^6$/mouse). Engraftment and quantification of BPDCN cells are already described; cf. Philippe L, Ceroi A, Bole-Richard E, Jenvrin A, Biichle S, Perrin S, et al., Bortezomib as a new therapeutic approach for blastic plasmacytoid dendritic cell neoplasm, Haematologica, 2017, 102(11):1861-8. T cells (untransduced and transduced) are injected in the tail vein on day 3 for CAL-1 model. Engraftment is monitored weekly by BLI measurements: mice received intraperitoneal 3 mg of luciferin (VivoGlo Luciferin, #P1043, Promega, Wisconsin, USA) within 10 minutes before imaging (IVIS Lumina Series III, Perkin Elmer, Massachusetts, USA). In PDX models, mice received T cells when BPDCN blasts are detected in blood sample. Blast count is monitored every 10 days by flow cytometry using anti-hCD45, anti-CD123 and BD TRUCOUNT™ tubes.

Some other embodiments described herein refer to an evaluation of the CAR toxicity on $CD123^{low}$ cells. For this a humanized mice model is used. More particularly, a humanized mice model (female hCD34-engrafted murine NOD/Shi-scid/IL-2Rγnull immunodeficient mouse strain: hu-NOG) is used to study the in vivo toxicity of CAR of the invention on normal human hematopoietic cells (n=3 donors). At day −15, 2 humanized mice are sacrificed; T cells are harvested from spleen and transduced to obtain CD123 CAR T cells or C0. At day 0, two humanized mices (generated with the same donor) are retro orbital injected with $20 \cdot 10^6$ C0 or CD123 CAR. At Day −5 and D15, total leucocytes, monocytes, B and T lymphocytes, pDC and basophiles are quantified in blood and HSC/progenitors in bone marrow obtained after sacrifice (only at D15). For the evaluation of the in vitro cytotoxicity of CAR T-cells on normal autologous CD34 cells, magnetically sorted CD34+ cells can be used (CD34 microbeads, Miltenyi Biotec) that have been obtained from bone marrow of sacrificed humanized mice and CD123 CAR. Or alternatively, C0 produced from T cells obtained from the same humanized mice as described above (n=3) can be used. Co-culture are done in the same conditions that are described for BPDCN cells in a E:T ratio of 5:1. The numbers of viable $hCD34^+$ after co-culture with the CD123 CAR or C0 are compared. Same experiments are done using CD34 cells magnetically sorted from cord blood co-cultured with CAR CD123 or C0 produced from the same cord blood T lymphocytes (n=3).

FIG. 12 shows transduction efficiency, cf. FIG. 12 B. The transduction efficiency was evaluated by quantification of T cells co-expressing CD3 and CD19. Variable transduction level of 17.8% in average was observed ([3-57%], n=43) with the retroviral construct. This may indicate a variable transduction capacity that can be controlled by using magnetic selection in order to effectively use CAR T cells (purity of transduced T cell were 90%±9.5% ([60-98.5%], n=43). More precisely, Item B of FIG. 12 shows a representative phenotype CD3/CD19 of untransduced T cells (C0) compared to transduced T cells of the invention (CD123 CAR T cells or Anti-CD123 CAR T cells) before and after magnetic cell separation for T cells of the invention.

Lentiviral transduction show good transduction efficiency (91.2%±5.22, n=6), cf. FIG. 12 B.

For the purpose of the present invention, evaluation of the expression of the CAR construction in transduced cells can be made by Western blotting. More particularly, untransduced T cells (C0) and CD123 CAR T-cells according to the invention are lysed by sonication in RIPA buffer supplemented with a protease inhibitor cocktail (complete Mini EDTA-free; Roche, France). Equivalent amounts of protein are fractioned with SDS-PAGE, and were electrotransferred onto PVDF membranes (Bio Rad, California, USA). Membranes are probed overnight with primary antibodies (diluted at 1:1000) that bound to human CD3ζ chain (51-6527GR, BD Biosciences). antibodies are added (diluted $1:10^6$) that recognize β-actin (clone AC15, #A5441, Sigma-Aldrich, Missouri, USA) as an internal loading control. To carry out immunodetection, a secondary antibody is added (diluted at 1:6000): sheep anti-mouse IgG (#515-035-062, Jackson, Pennsylvania, USA). Chemiluminescence is detected by adding appropriate detection reagents (Clarity™ Western ECL Blotting Substrates, Bio-Rad, Cressier, Switzerland), and by using a camera and Bio-1D software (Wilber-Lourmat, Collégien, France).

FIG. 12 also shows western blotting, cf. FIG. 12 C. The expression of the CAR of the invention was verified by immunoblotting in 3 experiments (FIG. 2C). The lower band (16 kDa) corresponding to the endogenous CD3ζ chain was detected in transduced and untransduced T cells lysates but an additional band appears at 55 kDa in CD123 CAR T cells corresponding to theoretical size of the CD123 CAR construct. This band is absent from untransduced T cells. More precisely, item C of FIG. 12 shows western blot analysis of the CD123 CAR protein expression (55 kDa, CD3ζ fused to CAR construct compared to endogenous CD3ζ (16 kDa)) in whole-cell lysate derived from genetically modified T cells (CAR) compared to no expression in C0.

FIG. 12 also shows cytometric flow analysis, cf. FIG. 12 D and FIG. 12 E. Surface expression of CD123 CAR on T cells was confirmed by flow cytometric analysis using biotin-conjugated CD123 protein. Fixation of the protein CD123 occurred only on the transduced T cells (16%±11.5, n=8 for CD123R CAR and 31.5%±12.2, n=9 for CD123L CAR) versus 0% on untranduced T cells. Item D of FIG. 12 shows the CAR cell surface expression by flow cytometry: CD123 CAR and C0 are stained with biotin conjugated CD123 protein plus streptavidinPE. More precisely, at item D of FIG. 12 is shown an example of expression and in item E of FIG. 12 is shown the mean value of a total of 17 different experiments (n=8 for CD123R CAR and n=9 for CD123L CAR) are reported. Expression was not detected in untransduced cells.

More generally, for the purpose of the present invention, the evaluation of the surface expression of the CAR in transduced cells is done by flow cytometry. More precisely, the expression of the anti-CD123 scFV on cell surface of transduced T-cells is examined by flow cytometry. T-cells (100 000 cells) are stained with 0.25 μg of biotinylated CD123 protein for 1 h at room temperature followed by PE-conjugated streptavidin (BD Biosciences). The fixation of CD123 on the $CD3^+$ $CD19^+$ CAR cells in comparison to C0 is then evaluated.

FIG. 13 shows the nucleic acid sequence (SEQ ID NO: 97) of a CAR according to the invention.

The CAR is built with antibody AB1 of the invention. Nucleic acids corresponding to the Peptide signal, Tag HA, Heavy Chain, Hinge1, Light chain, Hinge2, CD28, 4.1BB, and CD3z are respectively highlighted in different shades from left to right in reading order.

Accordingly, an object of the present invention is an isolated nucleic acid molecule encoding a chimeric antigen receptor (CAR), wherein the nucleic acid molecule consists of a sequence having an identity of at least 85%, preferentially 90%, more preferentially 95% to SEQ ID NO: 97.

Another object of the present invention is an isolated nucleic acid molecule encoding a chimeric antigen receptor (CAR), wherein the nucleic acid consists of SEQ ID NO: 97.

Figure 14:
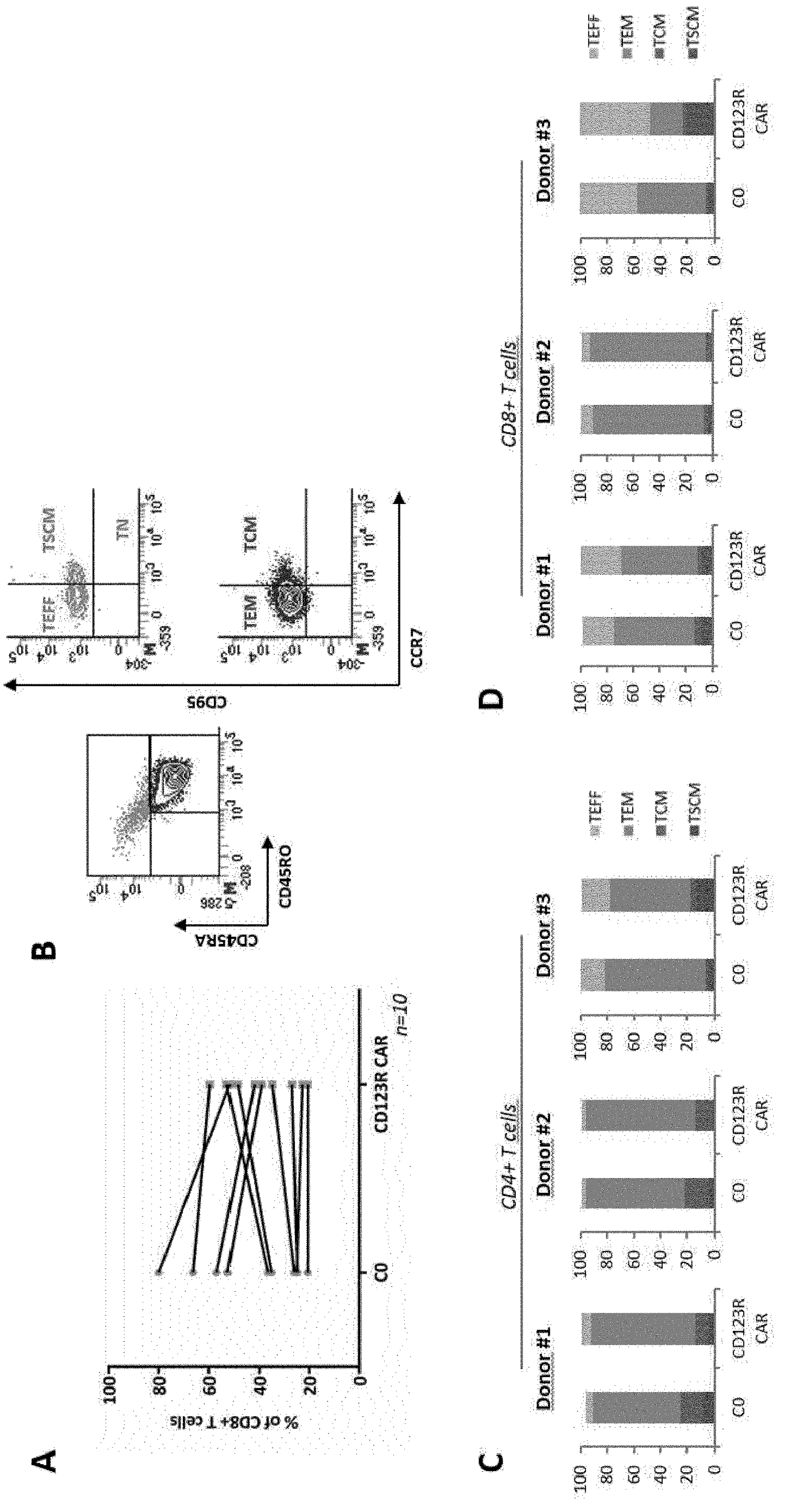
FIG. 14 shows flow cytometry graphs relative to the evaluation of the phenotype of CAR T cells according to the invention compared to non-transduced T cells.

FIG. 14 shows flow cytometry graphs relative to the evaluation of the phenotype of CAR T cells according to the invention compared to untransduced T cells.

CAR CD123 cells product of the present embodiment comprises a mix of CD4 T cells (58% [22.6-84.8%], n=23) and CD8 T cells (39.6% [16.1-74.9%], n=23). No difference of CD4/CD8 ratio is observed between untransduced and transduced T cells. Item A of FIG. 14 shows the percentage of the CD8 population (in contrario to CD4 population) in untransduced T cells C0 and genetically modified cells (GMC) CD123R CAR T cells in 10 experiments based on ten different donors. Overall, there is no significant difference in the repartition of both populations (CD4 and CD8) in transduced and untransduced cells (ns, p=0,57), cf. FIG. 14 A. Item B of FIG. 14 shows a representative example of flow cytometry analysis of memory T-cell phenotype based on expression of CD45RA and CD45RO and of CD95 and CCR7, cf. FIG. 14 B. Items C and D of FIG. 14 respectively show repartition of T subpopulations of CD4 and CD8 in CD123R CAR T cells (GMC) compared to C0 for three donors. TEFF: effector T cell; TEM: effector memory T cell; TCM: central memory T cell; TSCM: T memory stem cell FIG. 15 shows a diagram of co-culturing target cells with chimeric antigen receptors of the invention and non-transduced cells and flow cytometry graphs relative to specific cytotoxicity against BPDCN cell lines and BPDCN patient-derived xenografts cells of a CAR of the invention, and further against CD123 negative cells demonstrating specificity of targeting.

Figure 15:
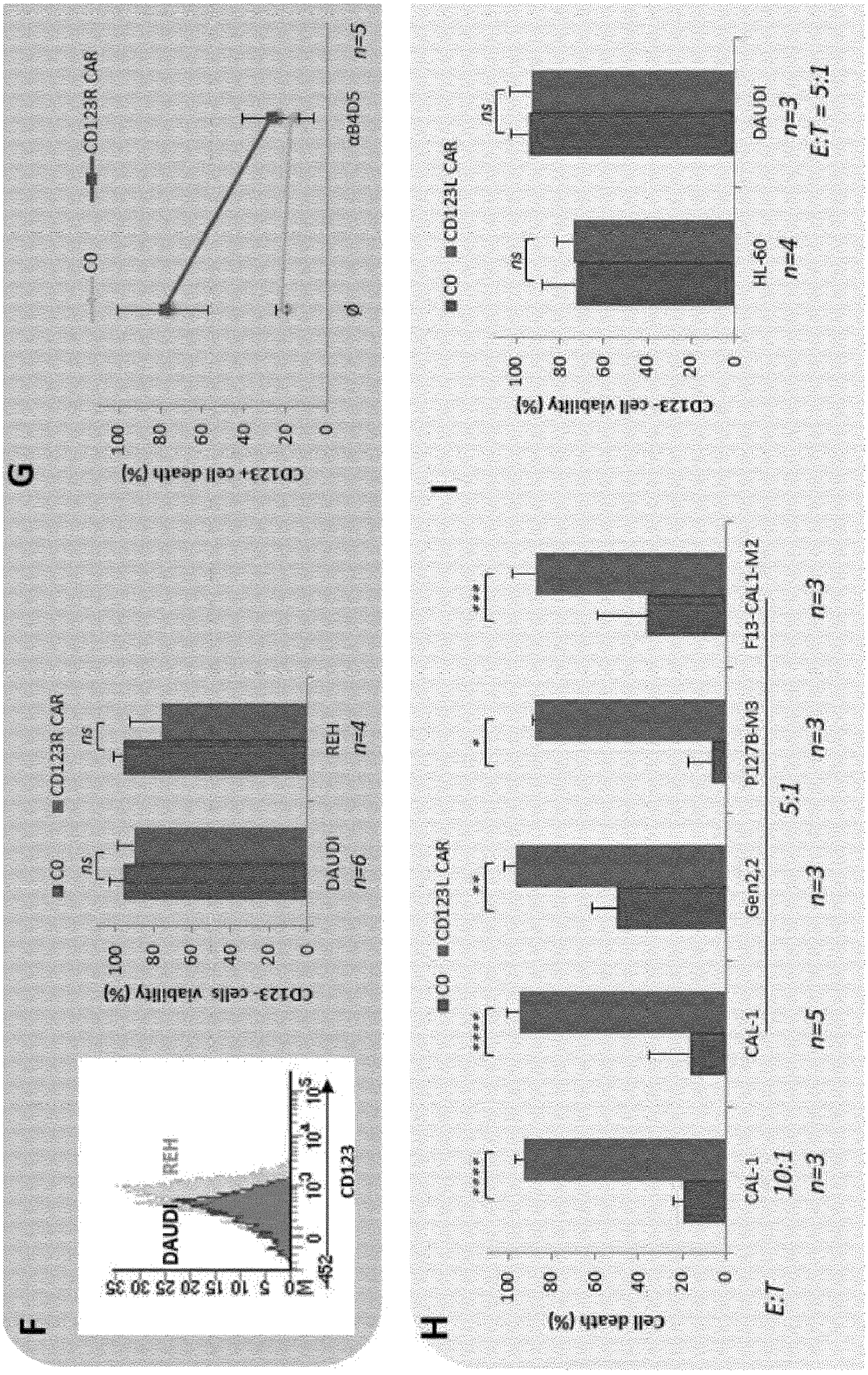
FIG. 15 shows a diagram of co-culturing target cells with chimeric antigen receptors of the invention and non-transduced cells and flow cytometry graphs relative to specific cytotoxicity against BPDCN cell lines and BPDCN patient-derived xenografts cells of a CAR of the invention.

More generally, FIG. 15 shows specific cytotoxicity against BPDCN cell lines and BPDCN patient-derived xenografts cells of a CAR of the invention. For each graph, mean and SD are indicated.

Item A of FIG. 15 shows on the left a picture of the general principal of co-culturing C0 and CD123 CAR T cells against BPDCN cells, followed on the right by flow cytometry results. To evaluate CD123 CAR T cells cytotoxicity (e.g. ability to induce apoptosis on target cells), target cells were co-cultured for 16 h (PDX) or 24 h (CAL-1, GEN 2.2, DAUDI, REH) with effector T cells (C0 or CD123 CAR) at a E:T ratio of 10:1 (CD123R CAR) or 5:1 (CD123L CAR) or alone 1:0 (control), cf. FIG. 15 A. T-cells are targeted using eDye cell proliferation and 7-AAD staining allow to detect BPDCN cell death. Living target cells are 7-AAD$^-$ CD123+ (grey).The percentage of depletion was calculated by comparison of the number of living target cells (7AAD$^-$/CD123$^+$) in the CAR CD123 culture or C0 culture versus culture alone. As the T lymphocytes used for CAR production are allogenic to target cells, cytotoxicity is obtained in the C0 culture conditions (linked to the allogenecity of T cells). This is compared to cytotoxicity obtained in the CAR CD123 culture. Specific cytotoxicity of C0 or CD123 CAR conditions represented % of target cell death compared to % of death in target alone condition.

Item B of FIG. 15 shows CD123 expression in BPDCN cell lines (CAL-1 and GEN 2.2) by flow cytometry, item C of FIG. 15 shows specific cytotoxicity of CD123R CAR T cells against CAL-1 and GEN 2.2 after co-culture (CAL-1, n=22 and GEN 2.2, n=10) with an E:T of 10:1, item D of FIG. 15 shows CD123 expression in BPDCN PDXs cells by flow cytometry and item E of FIG. 15 shows cytotoxicity of CD123 CAR T cells against indicated CD123+ PDXs cells (n=9 for Pl27B-M5 and n=6 for P25B-M1. CD123R CAR T cells demonstrated robust antigen-specific cytotoxicity when cultured with CAL-1 cell lines (depletion of 69.1%±27.4 with CD123R CAR versus 22.2%±11.8 with C0, n=22, p<0.0001); GEN 2.2 cell lines (65.7%±26.4 with CD123R CAR versus 25.3%±12.2 with C0, n=10, p=0.0004) as well as PDX cells (68%±22.2 with CD123R CAR versus 13%±29.5 with C0, n=15), cf. FIG. 15 B, FIG. 15 C, FIG. 15 D and FIG. 15 E.

Item F of FIG. 15 shows on the left the absence of CD123 expression in DAUDI and REH cell lines by flow cytometry and on the right the percentage of viability of these cell lines (DAUDI, n=6 and REH, n=4) after co-culture with C0 and CD123 CAR. There was no cytotoxicity on the CD123$^-$ cell lines DAUDI and REH, cf. FIG. 15 F.

Item G of FIG. 15 shows a graphic of cell death percentage in conditions wherein CAL-1 are incubated with B4D5 antibody for 1 h before co-culture with C0 or CD123R CAR T cells.

Confirmation of specific cytotoxicity of the CD123R CAR T cells is carried out by pre-incubation of CAL-1 cells with the B4D5 CD123 antibody (AB1). Pre-incubation induce an inhibition of the cytotoxicity of CD123R CAR T cells, n=5. Inhibition of the CAR CD123 cytotoxicity leads to a level of death with CD123R CAR similar to cell death observed with C0 (27.2%±13.7 with CD123 CAR and 17.2%±11 with C0, (ns, p=0.2368, n=5), cf. FIG. 15 G). Indeed, the CD123R CAR T cells show a specific cytotoxic against CD123$^+$ leukemic cell in vitro.

Item H of FIG. 15 shows specific cytotoxicity of CD123L CAR against CAL-1 (E:T=10:1, n=3 or E:T=5:1, n=5), GEN 2.2 (E:T=5:1, n=3) and 2 PDX (E:T=5:1, Pl27B-M3, n=3 and F13-CAL-1-M2, n=3). Cytotoxicity assays are validated with CD123L CAR at E:T=10:1 and 5:1 ratio, cf. FIG. 15 H). For CAL-1, at a E:T ratio equals to 5:1, a depletion of 94.6%±6.1 with CD123L CAR is observed versus 16.6%±18.7 with C0 (p<0.0001, n=5); GEN 2.2: depletion of 96.7%±4.9 with CD123L CAR versus 7%±11.9 with C0 (p=0.0032, n=3); PDX: depletion of 87.5%±6.8 with CD123L CAR versus 21.2%±22.7 with C0 (p<0.0001, n=6), cf. FIG. 15 H.

Item I of FIG. 15 shows percentage of viability of CD123− cell lines (DAUDI, n=3 and HL-60, n=4) after co-culture with C0 and CD123L CAR T cells. Again, no toxicity against CD123$^-$ cell line HL-60 and DAUDI is observed (viability of HL-60 of 73.8±7.3 with CD123L CAR versus 72.5±15.5 with C0, n=4; viability of DAUDI of 93 i 9.9, with CD123L CAR versus 94.1±8.4 with C0, n=3), cf. FIG. 3 I.

Figure 16:
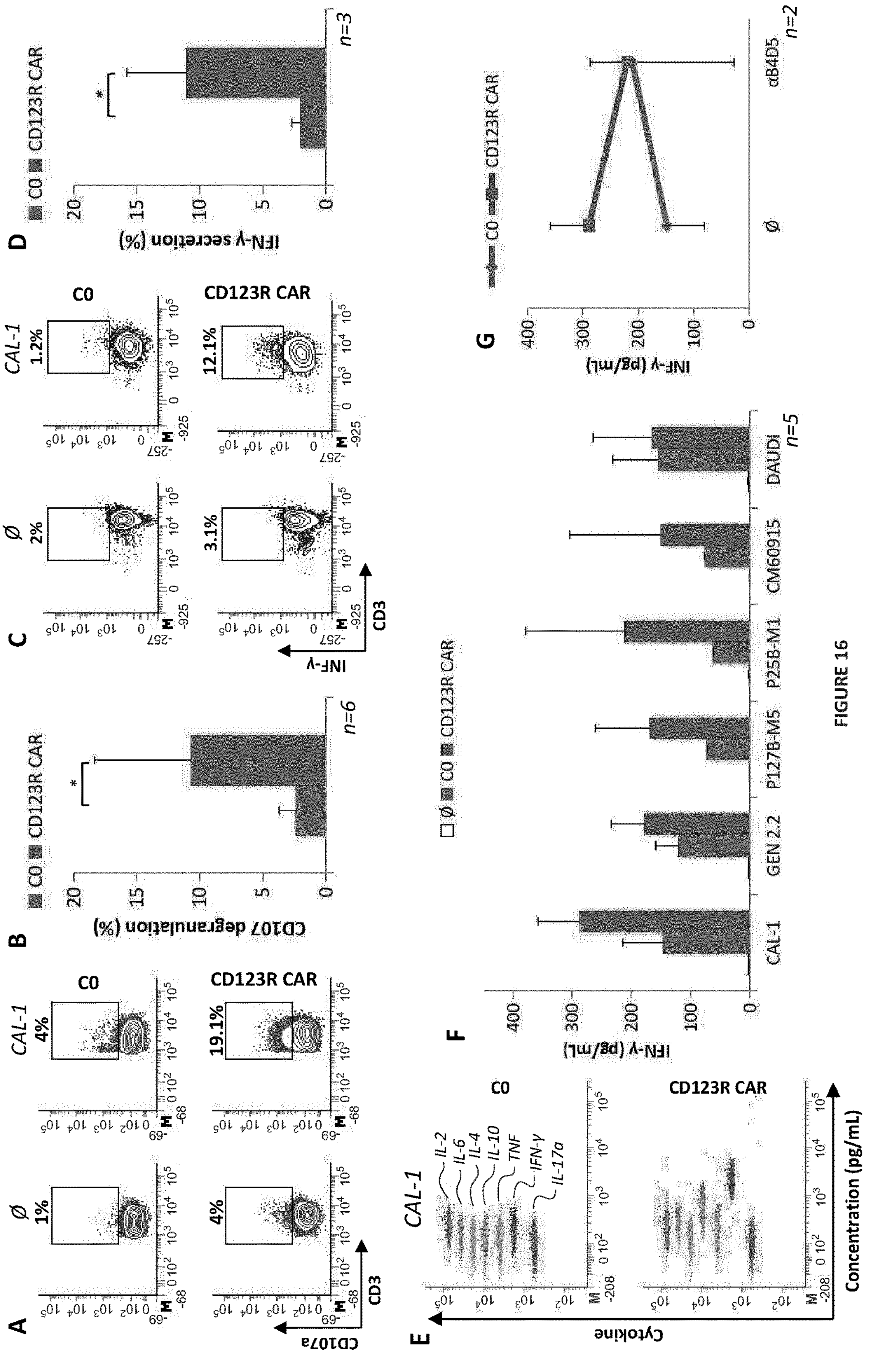
FIG. 16 shows graphs of flow cytometry relative to functional characterization of CD123R CAR T cells of the invention in co-culture with $CD123^+$ target cells.

FIG. 16 shows graphs of flow cytometry relative to functional characterization of CD123R CAR T cells of the invention in co-culture with CD123$^+$ target cells.

Item A of FIG. 16 shows a representative degranulation assay with CD107a expression of CD123R CAR compared to untransduced cells (C0) after co-culture with CAL-1 cells line for 6 h with an E:T of 10:1. Item B of FIG. 16 shows histograms representing the mean value of 6 experiments+/−SD, *p=0,0253. In order to determine the effector function of CD123R CAR T cells, different parameters were measured after co-culture. CD123R CAR T cells degranulate since they expressed an amount of CD107a (10.7%±7.6 for CD123R CAR against 2.4±1.3 for C0, p=0.0253, n=6, cf. FIG. 16 A and FIG. 16 B.

Item C of FIG. 16 shows intracellular cytokine IFN-γ staining after 24 h of co-culture with CAL-i. Item D of FIG. 16 shows histograms representing the mean of 3 experiments+/−SD, *p=0,0314. CD123R CAR T cells secrete IFN-γ in the intracellular compartment (11%±4.7 for CD123R CAR against 2%±0.7 for C0, p=0.0314, n=3) (FIG. 4C&D) indicating a CD123R CAR T-cell activation, cf. FIG. 16 C and FIG. 16 D.

Item E of FIG. 16 shows A representative Cytokine Bead Array Human Th1/Th2/Th17 analysis in co-culture supernatant (from up to down: IL-2; IL-6; IL-4; IL-10; TNF; IFN-γ; IL-17a—data are available in color where red=IL-2; orange=IL-6; yellow=IL-4; green=IL-10; blue=TNF; dark blue=IFN-γ; purple=IL-17a). In supernatants is found a higher level of IFN-γ and IL10 (CBA analysis) with the CD123 CAR co-culture (IL-10: 91.4 pg/mL±19.4 with CD123R CAR against 31.6±6.8 with C0, n=5), cf. FIG. 16 E.

Item F of FIG. 16 shows histograms representing the mean of INF-γ secretion by C0 and CD123R CAR after co-culture with different target cells, n=3. A significant augmentation of IFN-γ secretion (288 pg/mL±70 with CD123 CAR against 147 pg/mL±67 with C0, n=5) is observed. The secretion is specific since CD123R CAR T-cells do not secreted IFN-γ in co-culture with CD123$^-$ DAUDI cell lines, cf. FIG. 16 F.

Item G of FIG. 16 shows a graphic of IFN-γ secretion in conditions wherein inhibition of the IFN-γ secretion is measured by CBA analysis of CD123R CAR after co-culture with CAL-1 pre-incubated with B4D5 antibody 1 h, n=5. IFN-γ production by CD123R CAR T-cells is reduced when CAL-1 cells where pre-incubated with the CD123 B4D5 antibody of the invention leading to the level of cytotoxicity observed with C0, cf. FIG. 16 G. IL10 was also increase but at a lower level (91 pg/mL±19 with CD123 CAR against 31±6 with C0, n=5), cf. FIG. 16 E.

Figure 17:
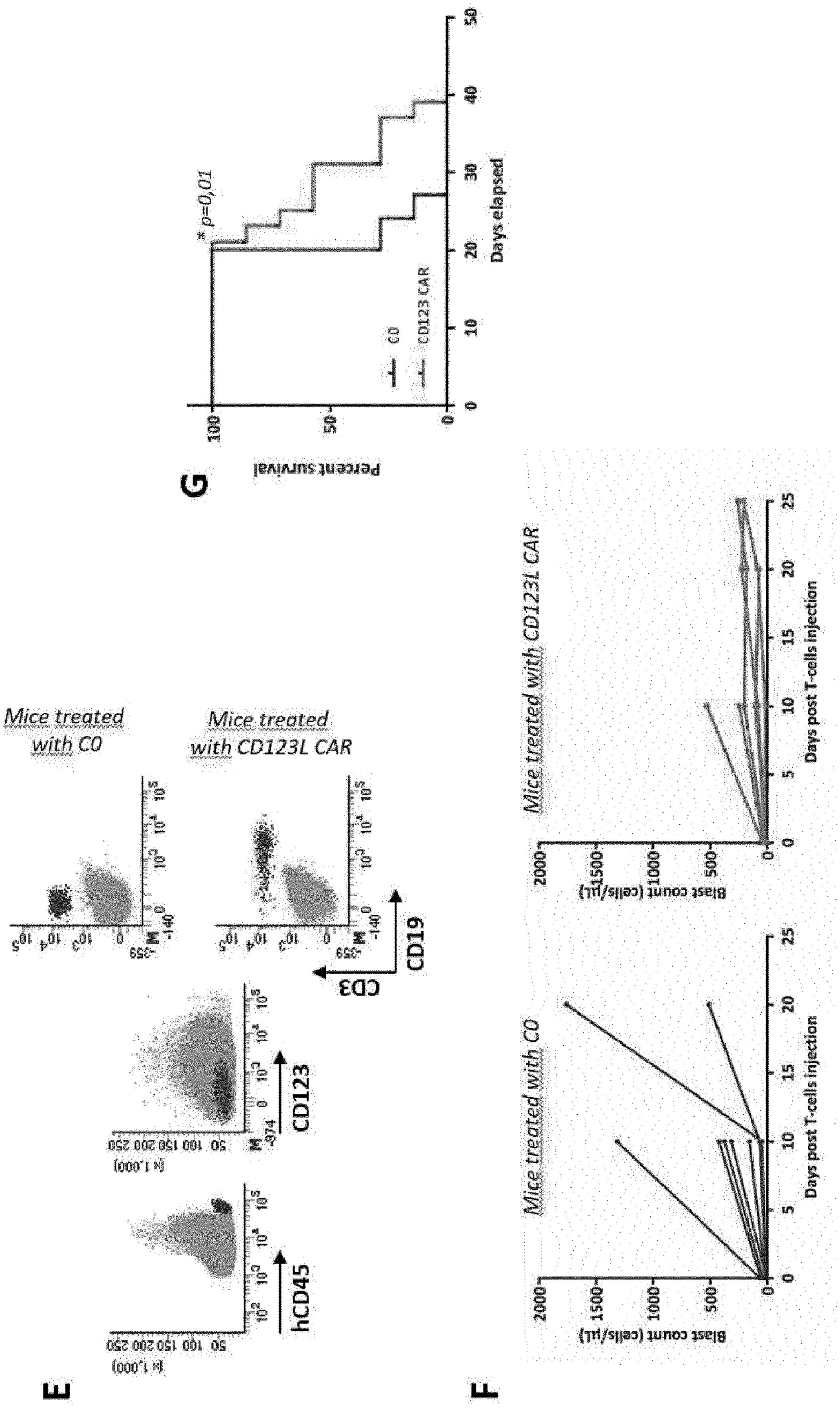
FIG. 17 shows a diagram of a xenograft model, bioluminescence imaging and graphs relative thereto, and flow cytometry graphs relative to in vivo antitumor activity of T cells of the invention against BPDCN cell lines (CAL-1) and patient derived xenograft cells (PDX)

FIG. 17 shows a diagram of a xenograft model, bioluminescence imaging and graphs relative thereto, and flow cytometry graphs relative to in vivo antitumor activity of T cells of the invention against BPDCN cell lines (CAL-1) and primary derived xenograft cells (PDX).

More generally, FIG. 17 shows in vivo antitumor activity of CD123L CAR T cells of the invention against CAL-1 and PDX (primary derived xenografts or patient derived xenografts).

Item A of FIG. 17 shows a general diagram of a xenograft model. The model is based on 6-8 week-old NSG mice that are irradiated (2,5 Gy) one day before CAL-1 luciferase cell line ($1\cdot10^6$) or PDX ($2\cdot10^6$) intravenously injection. C0 T cells or T cells comprising a CD123L CAR of the invention are injected in tail vein (5 or $10\cdot10^6$/mouse) at day 3 in CAL-1 model or when hCD45$^+$/CD123$^+$ BPDCN cells were detected in blood sample by flow cytometry, cf. FIG. 17 A.

Item B of FIG. 17 shows pictures of bioluminescence imaging analysis both prior and during CAR Anti-CD123 or C0 treatment for 33 days. A Cross indicates dead mice. Item C of FIG. 17 shows a diagram of a quantification of bioluminescence (cts/s) detected in C0 (dotted line) and CD123L CAR (full line) treated mice. Luminescence reflecting leukemia infiltration is higher in mice treated with C0 compared to CD123L CAR. This demonstrates the ability of CD123L CAR of the invention to control and/or treat BPDCN. Overall survival of mice treated with one dose of CD123L CAR show a highly survival compared to C0 treated mice (41 versus 26, 5 mice/group, p=0.0017 Log-rank test), cf. FIG. 17 B and FIG. 17 C.

Item D of FIG. 17 shows a diagram of overall survival analysis of mice. It appears clearly that a significant gain in survival occurs in mice treated with the CAR of the invention compared to C0 treated mice (n=5 mice per group). CD123L CAR of the invention controls BPDCN in a dose dependent manner. This is supported by the fact that a dose of $10\cdot10^6$ of CD123L CAR induce a better mice survival than a dose of $5\cdot10^6$ CD123L CAR. Further it is supported by a lower tumor burden (41 for $5\cdot10^6$ T cells versus 55 for $10\cdot10^6$ T cells, 5 mice/group, p=0.0173, Log-rank test), cf. FIG. 17 D.

The same foregoing experiments relative to FIG. 17 are further verified with the CD123R CAR, i.e. the retrovirus version of the invention.

Figure 18:
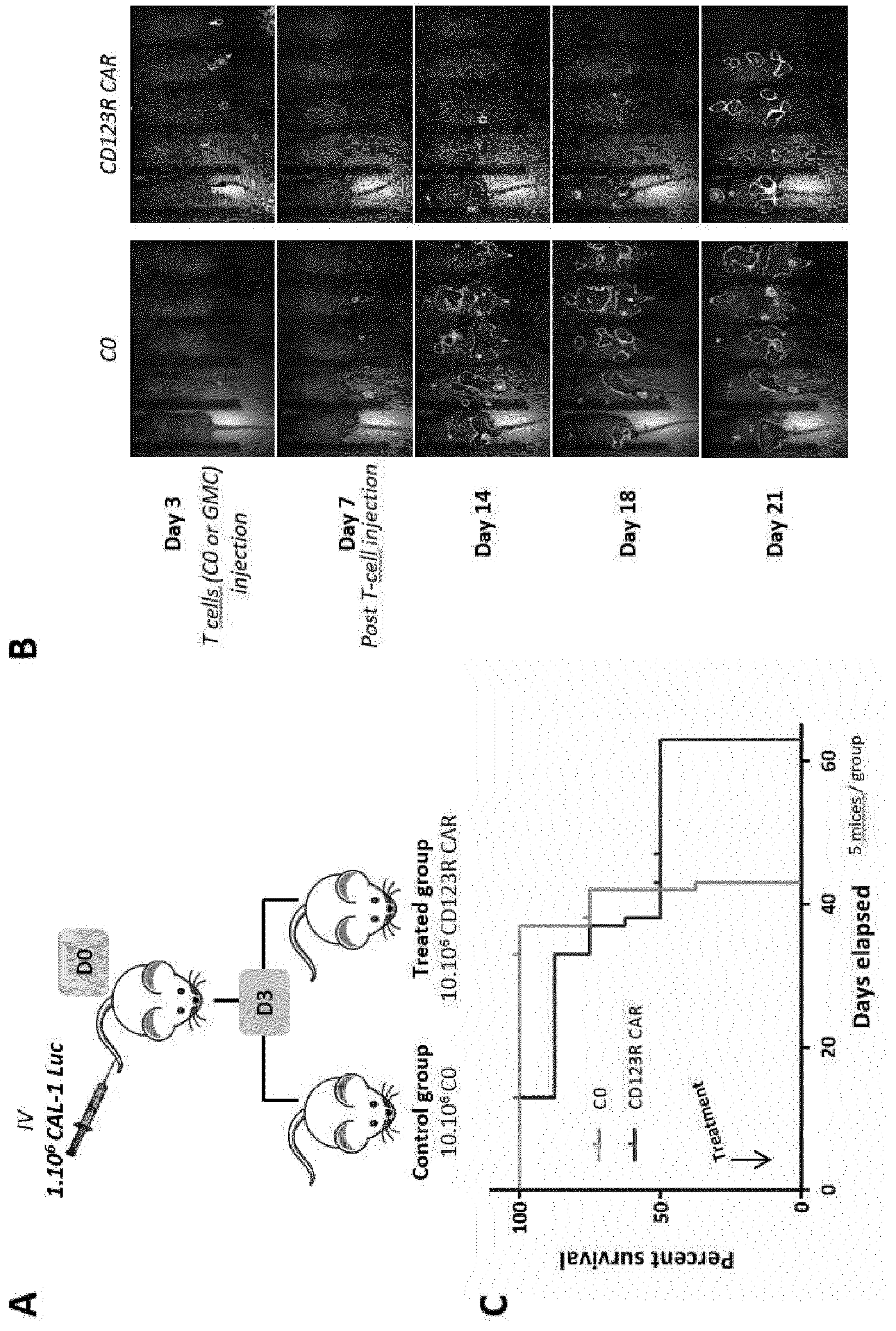
FIG. 18 shows a diagram of a xenograft model, bioluminescence imaging and graphs thereof relative to in vivo antitumor activity of T cells of the invention against a BPDCN cell lines (CAL-1)

Accordingly, FIG. 18 shows a diagram of a xenograft model, bioluminescence imaging and graphs thereof relative to in vivo antitumor activity of T cells of the invention against a BPDCN cell lines (CAL-1).

More generally, FIG. 18 shows in vivo antitumor activity of CD123R CAR T cells against CAL-i. Item A of FIG. 18 shows a general diagram of a xenograft model: NSG mice were irradiated (2,5 Gy) on day before CAL-1 luciferase injection ($1\cdot10^6$/mouse). C0 and GMC ($10\cdot10^6$) were injected in tail vein on day 3, cf. FIG. 18 A. Item B of FIG. 18 shows pictures of bioluminescence imaging prior and after CD123R CAR T-cell or C0 treatment following CAL-1 luciferase transplantation, cf. FIG. 18 B. Item C of FIG. 18 shows a diagram of overall survival analysis of mice. Survival analysis revealed significant survival for CD123R CAR treated mice compared to C0 treated mice (n=5 mices).

Consequently, the CARs of the invention treat effectively BPDCN.

Le CAR lentiviral version of the invention is further examined as shown in FIG. 17.

More particularly, the results are confirmed in a PDX model, cf. FIG. 17 A.

Item E of FIG. 17 shows a representative example of blood immunostaining performed during C0 or CD123L CAR treatment. Human T cells and primary BPDCN cells are distinguishable based on hCD45 expression. C0 (hCD45$^{High}$/CD123$^-$/CD3+ CD19−) or CD123L CAR (hCD45$^{High}$/CD123$^-$/CD3+ CD19+) are in grey (data are also available in color: blue); BPDCN cells (hCD45$^{Low}$/CD123$^+$) are in black (data are also available in color: pink). Item F of FIG. 17 shows graphs of mean BPDCN cell counts in blood mice injected with LAN PDX during treatment with C0 (dark line, or blue line when data in color) or CD123 CAR (grey line, or red line when data in color). Item G of FIG. 17 shows a graph showing overall survival of PDX xenograft mice. There is a higher survival for CD123L CAR treated mice compared to C0 treated mice (p=0,01). More particularly, in the PDX F13-LAN model, 78 days after injection, BPDCN cells are detected in all mice blood samples: one group received $5\cdot10^6$ of CD123L CAR (mean of BPDCN cells: 24 blast/μL [1-56], n=8) and the other one received $5\cdot10^6$ of C0 (26 blast/μL [1-66], n=8). Mice are monitored by blood analysis using trucount analysis during 25 days. At days 7, BPDCN cells and T-cells are quantified in mice blood samples, cf. FIG. 17 E and FIG. 17 F. During follow up, it is shown that treatment with CD123L CAR allow a control of the number of circulating BPDCN cells, cf. FIG. 17 C, and a higher overall survival of mice (31 days for CD123L CAR treatment versus 20 days for C0 treatment, p=0.0103), cf. FIG. 17 G). Overall, results obtained in mice models with a BPDCN line and PDX cells show that the CAR CD123L according to the invention allow a control of BPDCN in vivo.

The CAR retroviral version of the invention has been confirmed in the analogous experiments to those shown for the lentiviral version.

FIG. 19 shows a fluorescence graph relative to CD123 expression in different cell types, an immunohistochemistry picture of CD123 expression in tumor and normal tissues, flow cytometry graphs relative to CD123 expression, a diagram of the production of autologous T cells of the invention, and flow cytometry graphs relative toxicity of T cells of the invention to CD123 against cells expressing CD123 at low level.

More generally, FIG. 19 shows evaluation of toxicity of CD123L CAR T cells of the invention against cells expressing CD123 at low level.

It is demonstrated above that anti-CD123 antibodies (B4D5 of the invention and commercial antibody 6H6) show a close staining of CD123, cf. FIG. 10 C). Accordingly, 6H6 antibody was used to compare CD123 expression on normal haematopoietic cells and an endothelial cell line (HMEC) in comparison to BPDCN.

Item A of FIG. 19 shows a graph of CD123 expression in different cell lines. CD123 expression is studied using the 6H6 commercial antibody in order to compare BPDCN (n=60) to lymphocytes (n=31), monocytes (n=22), normal pDC (n=30) in blood and bone marrow samples, CD34 cells (n=16) in normal bone marrow and endothelial HMEC cell line (n=4). Results are presented in MFI, cf. FIG. 19 A. A low expression is detected on monocytes (MFI=1704 [778-4578], n=22), endothelial cell line (MFI=1252 [602-2283], n=4) and CD34+ cells (MFI=874 [326-1424], n=16) compared to BPDCN cells (MFI=11677 [2962-33439], n=60) and normal pDC (MFI=34352 [17822-76610], n=30). The CD123 CARs of the invention have less cytotoxicity on $CD123^{low}$ cells than on $CD123^{high}$ BPDCN cells in vivo.

To evaluate CD123 expression on tissues, tissue microarray is performed using the AB1 of the invention (or 18B4D5 antibody). For this, a US Food and Drug Administration standard frozen tissue array, including 90 tissue cores (30 organs) of 3 individual donors per organ (US Biomax, Rockville, MD, USA) was used. Immunostaining was detected using the UltraView Universal DAB Detection Kit (Ventana, USA). Images were acquired and analyzed with NDP.view 2.0 software. The staining intensity was graduated as follows: negative (0), weak staining (1+), moderate (2+), positive (3+), strong (4+). High CD123 (Cal-1) or negative (Daudi) expressing cell lines were respectively used as positive or negative controls.

Table 4 shows the results of the tissue microarray.

TABLE 4

Tissue micro array results.

| Tissues | Expression |
|---|---|
| CAL-1 cell line | Cytoplasm (4+) |
| Daudi cell line | 0 |
| Lymph node | Endothelial cells (3+) |
| Skeletal muscle | Endothelial cells (0/+1) |
| Prostate | 0 |
| Kidney | 0 |
| Liver | 0 |
| Lung | Endothelial cells and pneumocytes (1+) |
| Stomach | Endothelial cells (3+) |
| Esophagus | Endothelial cells (1+) |
| Heart | 0 |
| Colon | Endothelial cells (3+) |
| Small intestine | Vessels (1+) |
| Peripheral nerve | 0 |
| Smooth muscle | 0 |
| Cerebellum tissue | 0 |
| Ovary | Endothelial cells (1+) |
| Pancreas | 0 |
| Salivary gland | Endothelial cells (1+/2+) |
| Pituitary gland | 0 |
| Placenta | 0 |
| Skin | Endothelial cells (0/1+) |
| Spinal cord | 0 |
| Spleen | Endothelial cells (1+) |
| Testis | Endothelial cells (1+) |
| Adrenal gland | Medullosurrenal (1+) |
| Thyroid gland | Vessels (2+) |
| Ureter | Vessels (1+) |
| Uterine cervix | Vessels (1+) |

Results show that there is no significant expression of CD123 on specific tissue cells, only some endothelial cells in lymph node, stomach, colon, muscle, esophagus, skin and thyroid gland expressed CD123.

Item B of FIG. 19 shows pictures of immunohistochemistry with the B4D5 antibody on tumor tissues (BPDCN) and normal tissues. To compare the level of CD123 expression on endothelial cells in these tissues to the level of CD123 expression on BPDCN, IHC was realized on 3 normal tissues with the AB1 (18B4D5) antibody of the invention. Expression is compared to the expression level obtained on cutaneous lesions of BPDCN patients (n=2). A high level of CD123 expression on cutaneous lesions for the 2 patients is obtained as well as low expression on endothelial cells of the tested tissues, cf. FIG. 19 B. More particularly, BPDCN Patient 1 and Patient 2 show a high CD123 expression in the intradermal blastic infiltration of BPDCN cells. CD123 immunostaining of different healthy tissues show a low level of CD123 expression on endothelial cells (arrows). Specific tissue cells are CD123 negative. Low unspecific labelling is found in gastric and thyroid secretions.

Both approaches show a low level of CD123 on monocytes, CD34+ cells and endothelial cells which indicates a low potential "on target off tumor" of the CAR CD123 of the invention.

Item C of FIG. 19 shows representative expression of CD123 K532. More particularly, representative expression of CD123 on alive K562 CD123 line cultured alone or with C0 or CD123 CAR at E:T ratio=5:1 during 24 h is shown. The $CD123^{-}$ area is delimited by native K562 line (which is CD123-), $CD123^{low}$ area correspond to the maximum expression on monocytes and HMEC cells. $CD123^{pos}$ represent the level of CAL-1 expression and $CD123^{high}$ a level higher than CAL-i. This modelling shows the relationship between the level of CD123 expression on target cells and the killing efficiency of CD123L CAR using the K562 cell line that express different levels of CD123 (K562 CD123). As mentioned, cell lines are co-cultured with C0 or CD123 CAR or alone. Compare is made of the persistence of K562 cells in percentage of the entire population depending of their level of CD123 expression namely $CD123^{-}$, $CD123^{Low}$ (corresponding of the maximum of CD123 expression on monocyte and endothelial HMEC cells), $CD123^{+/High}$(corresponding of the level of CD123 expression on CAL-1 and more), cf. FIG. 19 C.

Item D of FIG. 19 shows a graph of the percentage of cells in each subgroup of K562's. The percentage of K562 $CD123^{low}$ cells are not decrease when cells are cultured with CAR CD123 whereas K562 $CD123^{pos/high}$ cells disappear; K562 $CD123^{-}$ cells increase in percentage (because CD123+ decrease), n=3. More particularly, distribution of K562 cells in relation with each expression level is the same alone or in co-culture with C0 whereas when K562 CD123 are co-culture with CD123L CAR, proportion of positive/high positive CD123 cells decrease significantly (n=3, p=0.0001) (and consequently the percentage of CD123− cells increase), cf. FIG. 19 D. Moreover for the $CD123^{Low}$ cells, the percentage of persistent cells was similar between the culture with C0 or CD123L CAR indicating a non-significant toxicity of the CD123L CAR on $C123^{low}$ cells. This demonstrates the capacity of CD123L CAR of the invention to kill CD123 high expresser cells with no or very little impact on weak expresser's cells.

Item E of FIG. 19 shows a graph relative to inhibition of target cell proliferation. Cytotoxicity of CD123L CAR T was evaluated on an endothelial cell line HMEC and primary monocytes. The inhibition of proliferation after 18 h co-culture is evaluated using a proliferation test (MTT cell proliferation test). Percentage of inhibition of cell growth is represented. CAL-1 is used as $CD123^{+}$ positive control and DAUDI as CD123− negative control, cf. FIG. 19 E.

Item F of FIG. 19 shows a diagram of experimental production of autologous CD123L CAR T-cells from human $CD34^{+}$ engrafted humanized mice. Item G of FIG. 19 shows a graph of CD123L CAR toxicity against CD34 cells. Two sources of CD34 cells are used. CD123L CAR T-cells produced from humanized mice. Further, cord blood are used to generated CD123L CAR T cells that are cultured with CD34+ cells sorted from the same cord blood, p=0, 0019. Item H of FIG. 19 shows representative expression of CD123 on $CD34^{+}$ cells from mice bone marrow after co-culture with autologous CAR T-cells or C0. The CD123L CAR induce a low lysis level of the $CD123^{low}$ expressing HMEC demonstrating a potential low toxicity of CD123L CAR on endothelial cells. Since CD123 is expressed at low level on CD34$^+$ cells, in vitro cytotoxicity of CD123L CAR T cells was investigated using the two strategies mentioned above. First, cord-blood sorted T cells are transduced to produce CD123L CAR or C0 T cells and co-cultured with autologous cord-blood-sorted CD34$^+$ cells; No depletion of CD34+ cells due to CD123L CAR is observed (depletion of 5.7%±5.1 for CD123L CAR and 11.7%±10.2 for C0, n=3, p=0.41), cf. FIG. 19 G. Second, human T-cells sorted from humanized mice are used to produce CD123L CAR or C0 that are co-cultured with autologous CD34 cells, cf. FIG. 19 F, FIG. 19 G and FIG. 19 H. Co-culture with CD123L CAR T cells or C0 cells lead to a low depletion of CD34+ cells (12.7%±16.3 for CD123L CAR whereas 2.7%±3.1 for C0, (ns, p=0.3542, n=3), cf. FIG. 19 G. Focusing on the CD34+/CD123+ subpopulation (representing 38% and 16% of the CD34+ cells, n=2), it is observed that only CD34$^+$/CD123$^+$ cells are killed with CD123L CAR (depletion of 82.1%±0.6) whereas CD34+/CD123− cells stay alive (depletion 3.5%±4.9), cf. FIG. 19 G and FIG. 19** H.

Further, CD123L CAR reactivity against autologous hematopoietic cells in vivo in the above mentioned humanized mice model is studied. Human CD123 CAR T cells or C0 were produced from human T cells. Transduction efficiency was 55.4%±9.2 (n=3) and efficiency of this CD123L CAR T-cells were validated in vitro before mice re-infusion.

FIG. 20 shows graphs based on flow cytometry relative to evaluation of toxicity of CD123L CAR T cells from humanized mice against CAL-1 and HL-60. More particularly, the toxicity of CD123L CAR T cells obtained from humanized mice against autologous CAL-1 and CD123 negative HL-60 cells is shown. A depletion of CAL-1 cells of 98.6% (±0.5%, n=3) with the CAR CD123 whereas only 0.7% (±0.6, n=3) with C0 and no difference of depletion between C0 and CD123L CAR against the CD123$^-$ HL-60 cell line is observed.

Item I of FIG. 19 shows a graph of a representative example of in vivo toxicity of CD123L CAR in humanized mice. For each mice, the fold change (FC) of human hematopoietic populations between D-5 and D15 (blood: B and T lymphocytes, monocytes, pDC) is measured. No significant differences in human immunes cells population (T and B lymphocytes, monocytes, pDC, basophiles) between the 2 groups of mice (C0 and CD123L CAR). Fold change of different immunocompetent cell subpopulations (total hCD45$^+$ cells, B-cells, T cells, monocytes) at days 15 after C0 or CD123L CAR injection is calculated against day-5 as reference. Cells count is performed from peripheral blood harvested by retro-orbital samples, a representative example is shown, n=3.

Item J of FIG. 19 shows a graph of the percentage of CD34+ cells in bone marrow of humanized mice 15 days after C0 or CD123L CAR T-cells injection, n=3 donors. In brief, FC is compared for mice injected with CD123L CAR and mice injected with C0, cf. FIG. 19 I and FIG. 19 J.

In three experiments, no difference of number of T, B lymphocytes, monocytes, pDC between the 2 groups of mice (C0 and CD123L CAR) is observed. Bone marrow CD34$^+$ cells are analyzed only at D15 and compared between mice injected with C0 versus CD123 CARL (n=3): no significant diminution of the percentage of the number CD34 in human CD45+ cells is observed, cf. FIG. 19 J.

These data confirm the absence or at least very low cytotoxicity of the CD123L CAR of the invention on CD123$^{low}$ hematopoietic cells. Further, the data confirm a selective cytotoxicity on the CD123+ subpopulation. In vivo no significant impact on circulating monocytes, lymphocytes and pDC and bone marrow CD34+ cells is observed.

FIG. 21 shows flow cytometry and graphs relative to CD123 CAR T-cells from BPDCN patient induced specific cytotoxicity against autologous BPDCN blasts. The results show that patient autologous CD123L CAR T-cells successfully eliminate primary BPDCN blast in vitro without cytotoxicity on normal blood cells (B and T lymphocytes).

Item A of FIG. 21 shows graphs from a flow cytometry phenotype assay wherein a phenotype CD3/CD19 of untransduced T cells (C0) is compared to transduced CD123L CAR T cells of the invention. For one BPDCN patient, autologous T-cells were used to generate effective CD123 CAR T-cells and C0. Greater than 79.2% transduction efficiency was achieved after 9 days, cf. FIG. 21 A. This efficiency is similar to those achieved in healthy donor T-cells, cf. FIG. 12 B.

Item B of FIG. 21 shows graphs of flow cytometry of CD123 CAR cell surface expression using biotin conjugated CD123 protein plus streptavidin$^{PE}$. This is the control of CD123 CAR cell surface expression with biotin conjugated CD123 protein, cf. FIG. 21 B.

Item C of FIG. 21 shows graphs of patient negative fraction after CD3/CD28 magnetic selection/activation. Grey data (pink in colored data) represent blast cells (CD45$^{Low}$, CD3$^-$, CD19$^-$, CD303$^+$, CD123$^{high}$), dark grey (blue in colored data) represent T lymphocytes cells (CD45$^{High}$, CD3$^+$, CD19$^-$, CD303$^-$, CD123$^-$) and light grey (orange in colored data) represent B lymphocytes cells (CD45$^{High}$, CD3$^-$, CD19$^+$, CD303$^-$, CD123$^-$). More particularly, functional activity of autologous CAR T cells against the patient BPDCN blasts is tested. The blast fraction is constituted from negative fraction of T-cell selection. It is composed of BPDCN blast (grey/pink population: CD45$^{Low}$/CD3$^-$/CD19$^-$/CD303$^+$/CD123$^{High}$), T-cells (blue/dark grey population: CD45$^{High}$/CD3$^+$/CD19$^-$/CD303$^-$/CD123$^-$) and B-cells (orange/light grey population: CD45$^{High}$/CD3$^-$/CD19$^+$/CD303$^-$/CD123$^-$), cf. FIG. 21 C. Co-culture of CD123L CAR and C0 with this autologous blast fraction for 24 h at an E:T ratio of 5:1 is made.

Item D of FIG. 21 shows graphs of flow cytometry and a cell viability diagram. It shows the specific cytotoxicity of CD123L CAR T cells against autologous BPDCN blasts after 24 h of co-culture with an E:T of 5:1 (Orange=B cells; pink=BPDCN blast; blue=T-cells, grey=C0 or CD123L CAR). More particularly, 95% elimination of BPDCN blast (CD123+) with no cytotoxicity on CD123− cells (T and B cells) is observed. As patient had no monocytes in blood toxicity evaluation on autologous monocytes cannot be performed. Yet, taken together, these results show that autologous CD123L CAR T cells of the invention are selectively effective at eliminating BPDCN blast in vitro.

As discussed above BPDCN is a clonal disease that progress in most cases to aggressive leukemia with very poor prognosis. Improved treatment is needed. While BPDCN cells are sensitive to chemotherapy, patients nevertheless relapse and develop resistance to second line treatment. The present invention provides a targeted therapy against CD123 which is the highly expressed "key antigen" in BPDCN patients. More particularly, the invention provides a BPDCN treatment using therapy based on a specific designed chimeric antigen receptor (CAR). The invention enables to selectively target and kill BPDCN cells in patients. Further the invention provides long-lasting remission in BPDCN.

Accordingly, the invention provides genetically engineered T-cells with a 3$^{rd}$ generation CAR that specifically recognizes and/or specifically binds CD123. The CAR of the invention is fabricated using retroviral or lentiviral strategy.

Both, retroviral or lentiviral strategy mediate anti-tumor activity. T cells expressing CD123 CAR of the invention can specifically lyse BPDCN cells. More particularly T cells expressing CD123 CAR of the invention can specifically lyse different BPDCN targets, i.e. BPDCN lines CAL-1 and GEN2.2 and/or BPDCN PDXs and primary BPDCN patient cells. When the CAR of the invention is cultured with these targets cells activate effector functions in vitro such as IFN-γ release and CD107a degranulation. Functionality of the CAR of the invention is specific to CD123 expression by target cells. In fact, when CD123 expression is blocked by pre-incubation with an anti-CD123 antibody of the invention (e.g. AB1) both the cytotoxicity and cytokines secretion are reversed. Moreover, a surprising effect of the invention is that no cytotoxicity (or substantially none) and/or no secretion of cytokine (or substantially none) takes place when the CAR of the invention is co-cultured with $CD123^{-}$ lines (Daudi, REH, HL-60). In vivo, T cells expressing the CAR of the invention display anti-leukemic activity against BPDCN lines. This positive effect of the invention provides long-term survival of BPDCN affected subjects (e.g. mouse).

The art discloses agents targeting CD123, i.e. antibodies [cf. Li F, Sutherland M K, Yu C, Walter R B, Westendorf L, Valliere-Douglass J, et al., Characterization of SGN-CD123A, A Potent CD123-Directed Antibody-Drug Conjugate for Acute Myeloid Leukemia, Molecular cancer therapeutics, 2018, 17(2):554-64; Xie L H, Biondo M, Busfield S J, Arruda A, Yang X, Vairo G, et al., CD123 target validation and preclinical evaluation of ADCC activity of anti-CD123 antibody CSL362 in combination with NKs from AML patients in remission, Blood cancer journal, 2017, 7(6):e567; and Kovtun Y, Jones G E, Adams S, Harvey L, Audette C A, Wilhelm A, et al., A CD123-targeting antibody-drug conjugate, IMGN632, designed to eradicate AML while sparing normal bone marrow cells, Blood advances, 2018, 2(8):848-58], fusion protein [Frankel A E, Woo J H, Ahn C, Pemmaraju N, Medeiros B C, Carraway H E, et al., Activity of SL-401, a targeted therapy directed to interleukin-3 receptor, in blastic plasmacytoid dendritic cell neoplasm patients, Blood, 2014; 124(3):385-92], BiTes [Pizzitola I, Anjos-Afonso F, Rouault-Pierre K, Lassailly F, Tettamanti S, Spinelli O, et al.; Chimeric antigen receptors against CD33/CD123 antigens efficiently target primary acute myeloid leukemia cells in vivo, Leukemia, 2014, 28(8):1596-605; Chu S Y, Pong E, Chen H, Phung S, Chan E W, Endo N A, et al., Immunotherapy with Long-Lived Anti-CD123×Anti-CD3 Bispecific Antibodies Stimulates Potent T Cell-Mediated Killing of Human AML Cell Lines and of CD123+ Cells in Monkeys: A Potential Therapy for Acute Myelogenous Leukemia, Blood, 2014, 124(21):2316; and Ruella M, Barrett D M, Kenderian S S, Shestova O, Hofmann T J, Perazzelli J, et al., Dual CD19 and CD123 targeting prevents antigen-loss relapses after CD19-directed immunotherapies, The Journal of clinical investigation, 2016, 126(10):3814-26], DART [Al-Hussaini M, Rettig M P, Ritchey J K, Karpova D, Uy G L, Eissenberg L G, et al., Targeting CD123 in acute myeloid leukemia using a T-cell-directed dual-affinity retargeting platform, Blood, 2016, 127(1):122-31], triplebodies or even CAR T-cells [Gill S, Tasian S K, Ruella M, Shestova O, Li Y, Porter D L, et al. Preclinical targeting of human acute myeloid leukemia and myeloablation using chimeric antigen receptor-modified T cells, Blood, 2014, 123(15):2343-54; and Tettamanti S, Marin V, Pizzitola I, Magnani C F, Giordano Attianese G M, Cribioli E, et al., Targeting of acute myeloid leukaemia by cytokine-induced killer cells redirected with a novel CD123-specific chimeric antigen receptor, British journal of haematology, 2013, 161(3):389-401]. While some of those studies demonstrate efficacy to some extend of anti-CD123 therapeutics on AML, various negative impacts on normal hematopoiesis are yet being reported, cf. Pemmaraju N, Lane A A, Sweet K L, Stein A S, Vasu S, Blum W, et al., Tagraxofusp in Blastic Plasmacytoid Dendritic-Cell Neoplasm, The New England journal of medicine, 2019, 380(17):1628-37.. The recent study using SL-401 (IL3 associated to diphtheria toxin) on 32 BPDCN patients at first line treatment relate a complete clinical response for 72% of the patients and 52% of survival at 24 months (including 45% of patients bring to allograft). Among the 15 previously treated patients, the response rate was 67%, and the median overall survival was 8.5 months. However, negative side effects (grade 3 or higher) are observed in 78% of patients leading to deaths of 3 patients in the study. As a consequence, toxicity is a major concern. The invention drastically improves the situation by addressing this problem.

Active CAR of the invention are tested clinical trials on BPDCN patients (and also on AML patients). No major toxicity events and/or negative effects are being reported.

Tissue micro-array (TMA) and immunohistochemistry (IHC) confirm that when an antibody of the invention (e.g. 18B4D5) is used to produce a CAR, none or low cytotoxicity occurs in $CD123^{low}$ cells.

Further, none or very weak cytotoxicity of CAR CD123L of the invention occurs on HMEC endothelial cell line.

In vivo data gathered from humanized mice injected with autologous CAR CD123 of the invention show no significant effect on mice treated with CD123 CAR of the invention on blood subpopulations: total CD45+ cells, T and B-cells and monocytes. The art reported problems potentially induced by CAR T-cells. The so called cytokine release syndrome (CRS) is frequent and studies show that monocyte are a major source of IL-1 and IL-6 during CRS, cf. Giavridis T, van der Stegen S J C, Eyquem J, Hamieh M, Piersigilli A, Sadelain M., CAR T cell-induced cytokine release syndrome is mediated by macrophages and abated by IL-1 blockade, Nat Med, 2018, 24(6):731-8; and Norelli M, Camisa B, Barbiera G, Falcone L, Purevdorj A, Genua M, et al., Monocyte-derived IL-1 and IL-6 are differentially required for cytokine-release syndrome and neurotoxicity due to CAR T cells, Nat Med, 2018, 24(6):739-48. The invention provides data leading the inventors to believe that a potential low level of monocytes depletion in vivo by CD123 CAR T-cells of the invention can participate to limit CRS (since monocytes express low level of CD123).

To control the CAR of the invention and for the purpose of treatment in humans, an embodiment of the T cell of the invention includes a suicide gene, i.e. system iCASP9/rimiducid, cf. Warda W, Larosa F, Neto Da Rocha M, Trad R, Deconinck E, Fajloun Z, et al. CML Hematopoietic Stem Cells Expressing IL1RAP Can Be Targeted by Chimeric Antigen Receptor-Engineered T Cells, Cancer research, 2019, 79(3):663-75.

The invention further provides anti-CD123 CAR T-cells that can specifically target and kill $CD123^{+}$ blast of BPDCN in vitro and in vivo with a safety profile evaluated on normal $CD123^{low}$ cells. Lentiviral strategy allows a good and reproducible transgene expression and good activity in vitro and in vivo. In clinical applications and or clinical development, the lentiviral version of the CAR of the invention is preferred, cf. Zufferey R, Donello J E, Trono D, Hope T J., Woodchuck hepatitis virus posttranscriptional regulatory element enhances expression of transgenes delivered by retroviral vectors. Journal of virology, 1999, 73(4):2886-92;

Miyoshi H, Blomer U, Takahashi M, Gage F H, Verma I M., Development of a self-inactivating lentivirus vector, Journal of virology, 1998, 72(10):8150-7; Zufferey R, Dull T, Mandel R J, Bukovsky A, Quiroz D, Naldini L, et al., Self-inactivating lentivirus vector for safe and efficient in vivo gene delivery. Journal of virology, 1998, 72(12):9873-80.

Accordingly, the object of the present invention is defined in appending claims. A further object of the invention is as defined in appending claims with reference to sequence homology instead of sequence identity.

Accordingly, an embodiment of the present invention is directed to an antibody selected in the group consisting of AB1, AB2, AB3, AB4, AB5 and AB6, wherein AB1 comprises a heavy chain having and a light chain, and wherein the heavy chain comprises a complementary determining region 1 (CDR1) having at least 90%, preferentially 100%, homology to amino acid sequence SEQ ID NO: 25, a complementary determining region 2 (CDR2) having at least 90%, preferentially 100%, homology to amino acid sequence SEQ ID NO: 13, and a complementary determining region 3 (CDR3) having at least 90%, preferentially 100%, homology to amino acid sequence SEQ ID NO: 1, and wherein the light chain comprises a complementary determining region 1 (CDR1) having at least 90%, preferentially 100%, homology to amino acid sequence SEQ ID NO: 26, a complementary determining region 2 (CDR2) having at least 90%, preferentially 100%, homology to amino acid sequence SEQ ID NO: 14, and a complementary determining region 3 (CDR3) having at least 90%, preferentially 100%, homology to amino acid sequence SEQ ID NO: 2

AB2 comprises a heavy chain and a light chain, and wherein the heavy chain comprises a complementary determining region 1 (CDR1) having at least 90%, preferentially 100%, homology to amino acid sequence SEQ ID NO: 27, a complementary determining region 2 (CDR2) having at least 90%, preferentially 100%, homology to amino acid sequence SEQ ID NO: 15, and a complementary determining region 3 (CDR3) having at least 90%, preferentially 100%, homology to amino acid sequence SEQ ID NO: 3, and wherein the light chain comprises a complementary determining region 1 (CDR1) having at least 90%, preferentially 100%, homology to amino acid sequence SEQ ID NO: 28, a complementary determining region 2 (CDR2) having at least 90%, preferentially 100%, homology to amino acid sequence SEQ ID NO: 16, and a complementary determining region 3 (CDR3) having at least 90%, preferentially 100%, homology to amino acid sequence SEQ ID NO: 4;

AB3 comprises a heavy chain having and a light, and wherein the heavy chain comprises a complementary determining region 1 (CDR1) having at least 90%, preferentially 100%, homology to amino acid sequence SEQ ID NO: 29, a complementary determining region 2 (CDR2) having at least 90%, preferentially 100%, homology to amino acid sequence SEQ ID NO: 17, and a complementary determining region 3 (CDR3) having at least 90%, preferentially 100%, homology to amino acid sequence SEQ ID NO: 5, and wherein the light chain comprises a complementary determining region 1 (CDR1) having at least 90%, preferentially 100%, homology to amino acid sequence SEQ ID NO: 30, a complementary determining region 2 (CDR2) having at least 90%, preferentially 100%, homology to amino acid sequence SEQ ID NO: 18, and a complementary determining region 3 (CDR3) having at least 90%, preferentially 100%, homology to amino acid sequence SEQ ID NO: 6;

AB4 comprises a heavy chain and a light chain, and wherein the heavy chain comprises a complementary determining region 1 (CDR1) having at least 90%, preferentially 100%, homology to amino acid sequence SEQ ID NO: 31, a complementary determining region 2 (CDR2) having at least 90%, preferentially 100%, homology to amino acid sequence SEQ ID NO: 19, and a complementary determining region 3 (CDR3) having at least 90%, preferentially 100%, homology to amino acid sequence SEQ ID NO: 7, and wherein the light chain comprises a complementary determining region 1 (CDR1) having at least 90%, preferentially 100%, homology to amino acid sequence SEQ ID NO: 32, a complementary determining region 2 (CDR2) having at least 90%, preferentially 100%, homology to amino acid sequence SEQ ID NO: 20, and a complementary determining region 3 (CDR3) having at least 90%, preferentially 100%, homology to amino acid sequence SEQ ID NO: 8;

AB5 comprises a heavy chain having and a light chain, and wherein the heavy chain comprises a complementary determining region 1 (CDR1) having at least 90%, preferentially 100%, homology to amino acid sequence SEQ ID NO: 33, a complementary determining region 2 (CDR2) having at least 90%, preferentially 100%, homology to amino acid sequence SEQ ID NO: 21, and a complementary determining region 3 (CDR3) having at least 90%, preferentially 100%, homology to amino acid sequence SEQ ID NO: 9, and wherein the light chain comprises a complementary determining region 1 (CDR1) having at least 90%, preferentially 100%, homology to amino acid sequence SEQ ID NO: 34, a complementary determining region 2 (CDR2) having at least 90%, preferentially 100%, homology to amino acid sequence SEQ ID NO: 22, and a complementary determining region 3 (CDR3) having at least 90%, preferentially 100%, homology to amino acid sequence SEQ ID NO: 10; and AB6 comprises a heavy chain having and a light chain, and wherein the heavy chain comprises a complementary determining region 1 (CDR1) having at least 90%, preferentially 100%, homology to amino acid sequence SEQ ID NO: 35, a complementary determining region 2 (CDR2) having at least 90%, preferentially 100%, homology to amino acid sequence SEQ ID NO: 23, and a complementary determining region 3 (CDR3) having at least 90%, preferentially 100%, homology to amino acid sequence SEQ ID NO: 11, and wherein the light chain comprises a complementary determining region 1 (CDR1) having at least 90%, preferentially 100%, homology to amino acid sequence SEQ ID NO: 36, a complementary determining region 2 (CDR2) having at least 90%, preferentially 100%, homology to amino acid sequence SEQ ID NO: 24, and a complementary determining region 3 (CDR3) having at least 90%, preferentially 100%, homology to amino acid sequence SEQ ID NO: 12.

Another object of the invention is an isolated nucleic acid molecule encoding a chimeric antigen receptor (CAR), or an isolated chimeric antigen receptor (CAR) molecule, wherein the CAR comprises an antibody or antibody fragment which includes an anti-CD123 binding domain, a transmembrane domain, and an intracellular signaling domain comprising at least a stimulatory domain, and wherein said anti-CD123 binding domain comprises:

(i) a heavy chain comprising and a complementary determining region 3 (CDR3) having at least 90%, preferentially 100%,and a light chain comprising a complementary determining region 3 (CDR3) having at least 90%, preferentially 100%, identity to amino acid sequence SEQ ID NO: 2;

(ii) a heavy chain comprising a complementary determining region 3 (CDR3) having at least 90%, preferentially 100%, identity to amino acid sequence SEQ ID NO: 3, and a light chain comprising a complementary determining region 3 (CDR3) having at least 90%, preferentially 100%, identity to amino acid sequence SEQ ID NO: 4;

(iii) a heavy chain comprising a complementary determining region 3 (CDR3) having at least 90%, preferentially 100%, identity to amino acid sequence SEQ ID NO: 5, and a light chain comprising a complementary determining region 3 (CDR3) having at least 90%, preferentially 100%, identity to amino acid sequence SEQ ID NO: 6

(iv) a heavy chain comprising a complementary determining region 3 (CDR3) having at least 90%, preferentially 100%, identity to amino acid sequence SEQ ID NO: 7, and a light chain comprising a complementary determining region 3 (CDR3) having at least 90%, preferentially 100%, identity to amino acid sequence SEQ ID NO: 8;

(v) a heavy chain comprising a complementary determining region 3 (CDR3) having at least 90%, preferentially 100%, identity to amino acid sequence SEQ ID NO: 9, and a light chain comprising a complementary determining region 3 (CDR3) having at least 90%, preferentially 100%, identity to amino acid sequence SEQ ID NO: 10 or (vi) a heavy chain comprising a complementary determining region 3 (CDR3) having at least 90%, preferentially 100%, identity to amino acid sequence SEQ ID NO: 11, and a light chain comprising a complementary determining region 3 (CDR3) having at least 90%, preferentially 100%, identity to amino acid sequence SEQ ID NO: 12.

Another embodiment of the invention is the above CAR but with reference to sequence homology instead of sequence identity.

Another object of the invention is an expression vector comprising the nucleic acid molecule as defined above, as well as an engineered immune cell (such as a T cell) comprising the nucleic acid molecule as defined above. According to the invention the cell can be used as a medicament and/or for use in the treatment of a proliferative disease in a mammal, preferably a human, wherein the proliferative disease is a disease associated with CD123 overexpression, preferably Blastic Plasmacytoid Dendritic Cell Neoplasm (BPDCN). Further, the invention is directed to a pharmaceutical composition comprising the engineered immune cell as defined above. Furthermore, the invention is directed to a method of engineering an immune cell comprising a transfection of a cell with an expression vector as defined above.

Another embodiment of the invention features an engineered immune cell comprising the nucleic acid molecule as described in the claims, wherein the cell is a T cell or a natural killer cell.

Other definitions of the invention may encompass an antibody that binds specifically to antigen CD123, wherein said antibody is selected from the group consisting of AB1, AB2, AB3, AB4, AB5 and AB6, and wherein AB1 comprises a heavy chain having at least 85% identity to amino acid sequence SEQ ID NO: 85 and a light chain having at least 85% identity to amino acid sequence SEQ ID NO: 86;

AB2 comprises a heavy chain having at least 85% identity to amino acid sequence SEQ ID NO: 87 and a light chain having at least 85% identity to amino acid sequence SEQ ID NO: 88;

AB3 comprises a heavy chain having at least 85% identity to amino acid sequence SEQ ID NO: 89 and a light chain having at least 85% identity to amino acid sequence SEQ ID NO: 90;

AB4 comprises a heavy chain having at least 85% identity to amino acid sequence SEQ ID NO: 91 and a light chain having at least 85% identity to amino acid sequence SEQ ID NO: 92;

AB5 comprises a heavy chain having at least 85% identity to amino acid sequence SEQ ID NO: 93 and a light chain having at least 85% identity to amino acid sequence SEQ ID NO: 94; and AB6 comprises a heavy chain having at least 85% identity to amino acid sequence SEQ ID NO: 95 and a light chain having at least 85% identity to amino acid sequence SEQ ID NO: 96; and wherein said antibody has a $K_D$ value of not more than $9.5\times10^{-9}$ M, an antibody dissociation rate $k_{off}$ of not more than $9.0\times10^{-4}$ $s^{-1}$, and an antibody association rate $k_{on}$ of at least $7\times10^4$ $Ms^{-1}$.

In one embodiment, the CD123 binding domain is a scFv comprising a light chain variable region comprising an amino acid sequence having at least one, two or three modifications but not more than 30, 20 or 10 modifications of an amino acid sequence of a light chain variable regions of SEQ ID NO: 2, SEQ ID NO 4, SEQ ID NO: 6, SEQ ID NO: 8, SEQ ID NO: 10, SEQ ID NO 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, or SEQ ID NO: 36 and a heavy chain variable region comprising an amino acid sequence having at least one, two or three modifications but not more than 30, 20 or 10 modifications of an amino acid sequence of a heavy chain variable region of SEQ ID NO 1, SEQ ID NO: 3, SEQ ID NO 5, SEQ ID NO 7, SEQ ID NO 9, SEQ ID NO: 11, SEQ ID NO 13, SEQ ID NO 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, or SEQ ID NO: 35.

In another embodiment, the CD123 binding domain is a scFv comprising (i) a light chain variable region comprising a complementary determining region 1 (CDR1) having at least 80%, 85%, 90%, 95%, 96%, 97%, 98%, 99% or having 100% identity with the amino acid sequence SEQ ID NO: 26, SEQ ID NO: 28, SEQ ID NO: 30, SEQ ID NO: 32, SEQ ID NO: 34, or SEQ ID NO: 36, a complementary determining region 2 (CDR2) having at least 80%, 85%, 90%, 95%, 96%, 97%, 98%, 99% or having 100% identity with the amino acid sequence SEQ ID NO: 14, SEQ ID NO: 16, SEQ ID NO: 18, SEQ ID NO: 20, SEQ ID NO: 22, or SEQ ID NO: 24 and a complementary determining region 3 (CDR3) having at least 80%, 85%, 90%, 95%, 96%, 97%, 98%, 99% or having 100% identity with the amino acid sequence SEQ ID NO: 2, SEQ ID NO 4, SEQ ID NO: 6, SEQ ID NO: 8, SEQ ID NO: 10, or SEQ ID NO 12, and (ii) a heavy chain variable region comprising a complementary determining region 1 (CDR1) having at least 80%, 85%, 90%, 95%, 96%, 97%, 98%, 99% or having 100% identity with the amino acid sequence SEQ ID NO: SEQ ID NO: 25, SEQ ID NO 27, SEQ ID NO: 29, SEQ ID NO: 31, SEQ ID NO: 33, or SEQ ID NO: 35, a complementary determining region 2 (CDR2) having at least 80%, 85%, 90%, 95%, 96%, 97%, 98%, 99% or having 100% identity with the amino acid sequence SEQ ID NO: 13, SEQ ID NO: 15, SEQ ID NO: 17, SEQ ID NO: 19, SEQ ID NO: 21, or SEQ ID NO: 23, and a complementary determining region 3 (CDR3) having at least 80%, 85%, 90%, 95%, 96%, 97%, 98%, 99% or having 100% identity with the amino acid sequence SEQ ID NO: 1, SEQ ID NO 3, SEQ ID NO: 5, SEQ ID NO: 7, SEQ ID NO 9, or SEQ ID NO 11.

In an embodiment, the anti-CD123 binding domain is connected to the transmembrane domain by a hinge region. Preferably, the encoded CAR includes a transmembrane domain of CD 28.

In an embodiment, the hinge region comprises the hinge sequence of IgG1 or a sequence with 95-99% identity thereof. In further embodiments, the hinge region comprises the hinge sequence of IgG4 or a sequence with 95-99% identity thereof. In further embodiments, the hinge region may also comprise the CH2-CH3 region of IgG1 or IgG4 or CD8a, or a sequence with 95-99% identity thereof.

In a preferred embodiment, the at least one co-stimulatory domain of the functional intracellular signaling domain is obtained from one or more protein selected from the group consisting of 4.1BB and/or a costimulatory domain obtained from CD3zeta.

The invention claimed is:

1. A monoclonal antibody that binds specifically to antigen CD123, wherein said monoclonal antibody comprises the complementarity determining regions of AB1, said monoclonal antibody having a KD value of $9.5\times10^{-9}$ M, or less, an antibody dissociation rate koff of $9.0\times10^{-4}$ $s^{-1}$ or less, and an antibody association rate kon of $7\times10^{4}$ $Ms^{-1}$, or greater, and comprises a heavy chain and a light chain, and wherein the heavy chain comprises a complementarity determining region 1 (CDR1) comprising the amino acid sequence of SEQ ID NO: 25, a complementarity determining region 2 (CDR2) comprising the amino acid sequence of SEQ ID NO: 13, and a complementarity determining region 3 (CDR3) comprising the amino acid sequence of SEQ ID NO: 1 and wherein the light chain comprises a complementarity determining region 1 (CDR1) comprising the amino acid sequence of SEQ ID NO: 26, a complementarity determining region 2 (CDR2) comprising the amino acid sequence of SEQ ID NO: 14, and a complementarity determining region 3 (CDR3) comprising the amino acid sequence of SEQ ID NO:2.

2. The monoclonal antibody according to claim 1, wherein the heavy chain has a variable region comprising a first framework region (FR1) consisting of the amino acid sequence of SEQ ID NO: 37, a second framework region (FR2) consisting of the amino acid sequence of SEQ ID NO: 38, a third framework region (FR3) consisting of the amino acid sequence of SEQ ID NO: 39, and a fourth framework region (FR4) consisting of the amino acid sequence of SEQ ID NO: 40, and wherein the light chain of AB1 has a variable region comprising a first framework region (FR1) consisting of the amino acid sequence of SEQ ID NO: 61, a second framework region (FR2) consisting of the amino acid sequence of SEQ ID NO: 62, a third framework region (FR3) consisting of the amino acid sequence of SEQ ID NO: 63, and a fourth framework region (FR4) consisting of the amino acid sequence of SEQ ID NO: 64.

3. An isolated nucleic acid molecule encoding a chimeric antigen receptor (CAR), wherein the CAR comprises an antibody or antibody fragment comprising an anti-CD123 binding domain, a transmembrane domain, and an intracellular signaling domain comprising at least a stimulatory domain, and wherein said anti-CD123 binding domain comprises:

a heavy chain comprising a complementarity determining region 1 (CDR1) comprising the amino acid sequence of SEQ ID NO: 25, a complementarity determining region 2 (CDR2) comprising the amino acid sequence of SEQ ID NO: 13, and a complementarity determining region 3 (CDR3) comprising the amino acid sequence of SEQ ID NO: 1, and a light chain comprising a complementarity determining region 1 (CDR1) comprising the amino acid sequence of SEQ ID NO: 26, a complementarity determining region 2 (CDR2) comprising the amino acid sequence of SEQ ID NO: 14, and a complementarity determining region 3 (CDR3) having at least 90% identity to amino acid sequence of SEQ ID NO: 2.

4. The isolated nucleic acid molecule according to claim 3, wherein the anti-CD123 binding domain is selected from the group consisting of an antibody, a Fv, a scFv, or a Fab.

5. The isolated nucleic acid molecule according to claim 3, wherein the intracellular signaling domain is CD3-zeta (CD3δ),optionally further comprising a costimulatory domain selected from the group consisting of CD28, 4. IBB, Inducible T-cell costimulator (COS), OX-40 or a combination thereof.

6. An isolated polypeptide molecule encoded by the nucleic acid molecule of claim 3.

7. An isolated chimeric antigen receptor (CAR) molecule comprising an antibody which includes an anti-CD123 binding domain, a transmembrane domain, and an intracellular signaling domain comprising at least a stimulatory domain, and wherein said anti-CD123 binding domain is the antibody of claim 1.

8. An expression vector comprising the nucleic acid molecule of claim 3, wherein the vector is selected from the group consisting of a DNA, a RNA, a plasmid, a lentivirus vector, an adenoviral vector, or a retrovirus vector.

9. An engineered immune cell comprising the nucleic acid molecule of claim 3.

10. The cell according to claim 9 for use in the treatment of a proliferative disease in a human, wherein the proliferative disease is a disease associated with CD123 overexpression.

11. A pharmaceutical composition comprising the engineered immune cell according to claim 9 and a pharmaceutical excipient.

* * * * *

SEQUENCE LISTING

```
<160> NUMBER OF SEQ ID NOS: 175

<210> SEQ ID NO 1
<211> LENGTH: 6
<212> TYPE: PRT
<213> ORGANISM: Mus <mouse, genus>
<220> FEATURE:
<223> OTHER INFORMATION: HC-CDR3 "18B4D5

<400> SEQUENCE: 1

Ala Arg Gly Leu Asp Tyr
1               5


<210> SEQ ID NO 2
<211> LENGTH: 9
<212> TYPE: PRT
<213> ORGANISM: Mus <mouse, genus>
<220> FEATURE:
<223> OTHER INFORMATION: LC-CDR3 "18B4D5

<400> SEQUENCE: 2

His Gln Leu His Arg Ser Pro Trp Thr
1               5


<210> SEQ ID NO 3
<211> LENGTH: 11
<212> TYPE: PRT
<213> ORGANISM: Mus <mouse, genus>
<220> FEATURE:
<223> OTHER INFORMATION: HC-CDR3 "17F7B2

<400> SEQUENCE: 3

Thr Lys Gly Tyr Arg Tyr Asp Trp Phe Ala Tyr
1               5                   10


<210> SEQ ID NO 4
<211> LENGTH: 9
<212> TYPE: PRT
<213> ORGANISM: Mus <mouse, genus>
<220> FEATURE:
<223> OTHER INFORMATION: LC-CDR3 "17F7B2

<400> SEQUENCE: 4

Ser Gln Asn Thr His Val Pro Phe Thr
1               5


<210> SEQ ID NO 5
<211> LENGTH: 12
<212> TYPE: PRT
```

<213> ORGANISM: Mus <mouse, genus>
<220> FEATURE:
<223> OTHER INFORMATION: HC-CDR3 “11B6E6

<400> SEQUENCE: 5

Val Arg Ala His Gly Tyr Tyr Phe Ala Met Asp Tyr
1 5 10

<210> SEQ ID NO 6
<211> LENGTH: 8
<212> TYPE: PRT
<213> ORGANISM: Mus <mouse, genus>
<220> FEATURE:
<223> OTHER INFORMATION: LC-CDR3 ”11B6E6

<400> SEQUENCE: 6

Lys Gln Ser Tyr Asn Leu Phe Thr
1 5

<210> SEQ ID NO 7
<211> LENGTH: 6
<212> TYPE: PRT
<213> ORGANISM: Mus <mouse, genus>
<220> FEATURE:
<223> OTHER INFORMATION: HC-CDR3 “14G12D7

<400> SEQUENCE: 7

Thr Arg Gly Val Asp Tyr
1 5

<210> SEQ ID NO 8
<211> LENGTH: 9
<212> TYPE: PRT
<213> ORGANISM: Mus <mouse, genus>
<220> FEATURE:
<223> OTHER INFORMATION: LC-CDR3 ”14G12D7

<400> SEQUENCE: 8

Leu Gln Phe Ser Gly Tyr Pro Phe Thr
1 5

<210> SEQ ID NO 9
<211> LENGTH: 12
<212> TYPE: PRT
<213> ORGANISM: Mus <mouse, genus>
<220> FEATURE:
<223> OTHER INFORMATION: HC-CDR3 “11A12C6

<400> SEQUENCE: 9

Val Arg Gly Asp Gly Tyr Tyr Trp Tyr Phe Asp Val
1 5 10

<210> SEQ ID NO 10
<211> LENGTH: 8
<212> TYPE: PRT
<213> ORGANISM: Mus <mouse, genus>
<220> FEATURE:
<223> OTHER INFORMATION: LC-CDR3 ”11A12C6

<400> SEQUENCE: 10

Lys Gln Ser Tyr Ser Leu Phe Thr
1 5

<210> SEQ ID NO 11
<211> LENGTH: 11
<212> TYPE: PRT
<213> ORGANISM: Mus <mouse, genus>

<220> FEATURE:
<223> OTHER INFORMATION: HC-CDR3 "15E11B7

<400> SEQUENCE: 11

Gly Gly Gly Val Arg Gly Ala Trp Phe Ala Phe
1 5 10

<210> SEQ ID NO 12
<211> LENGTH: 9
<212> TYPE: PRT
<213> ORGANISM: Mus <mouse, genus>
<220> FEATURE:
<223> OTHER INFORMATION: LC-CDR3 "15E11B7

<400> SEQUENCE: 12

Gln His Ser Ala Asp Leu Pro Tyr Thr
1 5

<210> SEQ ID NO 13
<211> LENGTH: 7
<212> TYPE: PRT
<213> ORGANISM: Mus <mouse, genus>
<220> FEATURE:
<223> OTHER INFORMATION: HC-CDR2 "18B4D5

<400> SEQUENCE: 13

Ile Ser Phe Ser Gly Ser Thr
1 5

<210> SEQ ID NO 14
<211> LENGTH: 3
<212> TYPE: PRT
<213> ORGANISM: Mus <mouse, genus>
<220> FEATURE:
<223> OTHER INFORMATION: LC-CDR2 "18B4D5

<400> SEQUENCE: 14

Ser Thr Ser
1

<210> SEQ ID NO 15
<211> LENGTH: 8
<212> TYPE: PRT
<213> ORGANISM: Mus <mouse, genus>
<220> FEATURE:
<223> OTHER INFORMATION: HC-CDR2 "17F7B2

<400> SEQUENCE: 15

Phe Tyr Pro Gly Lys Ser Asp Thr
1 5

<210> SEQ ID NO 16
<211> LENGTH: 3
<212> TYPE: PRT
<213> ORGANISM: Mus <mouse, genus>
<220> FEATURE:
<223> OTHER INFORMATION: LC-CDR2 "17F7B2

<400> SEQUENCE: 16

Lys Val Ser
1

<210> SEQ ID NO 17
<211> LENGTH: 7
<212> TYPE: PRT
<213> ORGANISM: Mus <mouse, genus>
<220> FEATURE:

<223> OTHER INFORMATION: HC-CDR2 "11B6E6

<400> SEQUENCE: 17

Ile Trp Thr Gly Gly Gly Thr
1 5

<210> SEQ ID NO 18
<211> LENGTH: 3
<212> TYPE: PRT
<213> ORGANISM: Mus <mouse, genus>
<220> FEATURE:
<223> OTHER INFORMATION: LC-CDR2 "11B6E6

<400> SEQUENCE: 18

Trp Ala Ser
1

<210> SEQ ID NO 19
<211> LENGTH: 7
<212> TYPE: PRT
<213> ORGANISM: Mus <mouse, genus>
<220> FEATURE:
<223> OTHER INFORMATION: HC-CDR2 "14G12D7

<400> SEQUENCE: 19

Ile Ile Tyr Ser Gly Thr Thr
1 5

<210> SEQ ID NO 20
<211> LENGTH: 3
<212> TYPE: PRT
<213> ORGANISM: Mus <mouse, genus>
<220> FEATURE:
<223> OTHER INFORMATION: LC-CDR2 "14G12D7

<400> SEQUENCE: 20

Ser Thr Ser
1

<210> SEQ ID NO 21
<211> LENGTH: 7
<212> TYPE: PRT
<213> ORGANISM: Mus <mouse, genus>
<220> FEATURE:
<223> OTHER INFORMATION: HC-CDR2 "11A12C6

<400> SEQUENCE: 21

Ile Trp Thr Gly Gly Gly Thr
1 5

<210> SEQ ID NO 22
<211> LENGTH: 3
<212> TYPE: PRT
<213> ORGANISM: Mus <mouse, genus>
<220> FEATURE:
<223> OTHER INFORMATION: LC-CDR2 "11A12C6

<400> SEQUENCE: 22

Trp Ala Ser
1

<210> SEQ ID NO 23
<211> LENGTH: 8
<212> TYPE: PRT
<213> ORGANISM: Mus <mouse, genus>
<220> FEATURE:
<223> OTHER INFORMATION: HC-CDR2 "15E11B7

<400> SEQUENCE: 23

Ile Asn Pro Tyr Asn Asp Tyr Thr
1 5

<210> SEQ ID NO 24
<211> LENGTH: 3
<212> TYPE: PRT
<213> ORGANISM: Mus <mouse, genus>
<220> FEATURE:
<223> OTHER INFORMATION: LC-CDR2 ″15E11B7

<400> SEQUENCE: 24

Leu Ala Ser
1

<210> SEQ ID NO 25
<211> LENGTH: 9
<212> TYPE: PRT
<213> ORGANISM: Mus <mouse, genus>
<220> FEATURE:
<223> OTHER INFORMATION: HC-CDR1 “18B4D5

<400> SEQUENCE: 25

Gly Tyr Ser Ile Thr Ser Asp Tyr Thr
1 5

<210> SEQ ID NO 26
<211> LENGTH: 7
<212> TYPE: PRT
<213> ORGANISM: Mus <mouse, genus>
<220> FEATURE:
<223> OTHER INFORMATION: LC-CDR1 ″18B4D5

<400> SEQUENCE: 26

Ser Ser Ile Ser Ser Ser Tyr
1 5

<210> SEQ ID NO 27
<211> LENGTH: 8
<212> TYPE: PRT
<213> ORGANISM: Mus <mouse, genus>
<220> FEATURE:
<223> OTHER INFORMATION: HC-CDR1 “17F7B2

<400> SEQUENCE: 27

Gly Tyr Ser Phe Thr Ser Tyr Trp
1 5

<210> SEQ ID NO 28
<211> LENGTH: 11
<212> TYPE: PRT
<213> ORGANISM: Mus <mouse, genus>
<220> FEATURE:
<223> OTHER INFORMATION: LC-CDR1 ″17F7B2

<400> SEQUENCE: 28

Gln Ser Leu Val His Ser Asn Gly Ile Thr Tyr
1 5 10

<210> SEQ ID NO 29
<211> LENGTH: 8
<212> TYPE: PRT
<213> ORGANISM: Mus <mouse, genus>
<220> FEATURE:
<223> OTHER INFORMATION: HC-CDR1 “11B6E6

<400> SEQUENCE: 29

Gly Phe Ser Leu Thr Ser Tyr Asp
1 5

<210> SEQ ID NO 30
<211> LENGTH: 12
<212> TYPE: PRT
<213> ORGANISM: Mus <mouse, genus>
<220> FEATURE:
<223> OTHER INFORMATION: LC-CDR1 "11B6E6

<400> SEQUENCE: 30

Gln Ser Leu Leu Asn Ser Ser Thr Arg Lys Asn Tyr
1 5 10

<210> SEQ ID NO 31
<211> LENGTH: 9
<212> TYPE: PRT
<213> ORGANISM: Mus <mouse, genus>
<220> FEATURE:
<223> OTHER INFORMATION: HC-CDR1 "14G12D7

<400> SEQUENCE: 31

Gly Tyr Ser Val Thr Ser Asp Tyr Ala
1 5

<210> SEQ ID NO 32
<211> LENGTH: 7
<212> TYPE: PRT
<213> ORGANISM: Mus <mouse, genus>
<220> FEATURE:
<223> OTHER INFORMATION: LC-CDR1 "14G12D7

<400> SEQUENCE: 32

Ser Ser Val Arg Ser Ser Tyr
1 5

<210> SEQ ID NO 33
<211> LENGTH: 8
<212> TYPE: PRT
<213> ORGANISM: Mus <mouse, genus>
<220> FEATURE:
<223> OTHER INFORMATION: HC-CDR1 "11A12C6

<400> SEQUENCE: 33

Gly Phe Ser Leu Thr Ser Tyr Asp
1 5

<210> SEQ ID NO 34
<211> LENGTH: 12
<212> TYPE: PRT
<213> ORGANISM: Mus <mouse, genus>
<220> FEATURE:
<223> OTHER INFORMATION: LC-CDR1 "11A12C6

<400> SEQUENCE: 34

Gln Ser Leu Phe Ser Ser Ser Ala Arg Lys Asn Tyr
1 5 10

<210> SEQ ID NO 35
<211> LENGTH: 8
<212> TYPE: PRT
<213> ORGANISM: Mus <mouse, genus>
<220> FEATURE:
<223> OTHER INFORMATION: HC-CDR1 "15E11B7

<400> SEQUENCE: 35

Gly Tyr Ser Phe Thr Gly Tyr Phe
1 5

<210> SEQ ID NO 36
<211> LENGTH: 10
<212> TYPE: PRT
<213> ORGANISM: Mus <mouse, genus>
<220> FEATURE:
<223> OTHER INFORMATION: LC-CDR1 "15E11B7

<400> SEQUENCE: 36

Lys Ser Val Ser Thr Ser Gly Tyr Asn Tyr
1 5 10

<210> SEQ ID NO 37
<211> LENGTH: 25
<212> TYPE: PRT
<213> ORGANISM: Mus <mouse, genus>
<220> FEATURE:
<223> OTHER INFORMATION: HC-FR1 "18B4D5

<400> SEQUENCE: 37

Glu Val Lys Leu Gln Glu Ser Gly Pro Gly Leu Val Lys Pro Ser Gln
1 5 10 15

Ser Leu Ser Leu Thr Cys Thr Val Thr
20 25

<210> SEQ ID NO 38
<211> LENGTH: 17
<212> TYPE: PRT
<213> ORGANISM: Mus <mouse, genus>
<220> FEATURE:
<223> OTHER INFORMATION: HC-FR2 "18B4D5

<400> SEQUENCE: 38

Trp Asn Trp Ile Arg Gln Phe Pro Gly Asn Lys Leu Glu Trp Met Gly
1 5 10 15

Tyr

<210> SEQ ID NO 39
<211> LENGTH: 38
<212> TYPE: PRT
<213> ORGANISM: Mus <mouse, genus>
<220> FEATURE:
<223> OTHER INFORMATION: HC-FR3 "18B4D5

<400> SEQUENCE: 39

Ser Tyr Asn Pro Ser Leu Lys Ser Arg Leu Ser Ile Thr Arg Asp Thr
1 5 10 15

Ser Lys Asn Gln Phe Phe Leu Gln Leu Asn Ser Val Thr Thr Glu Asp
20 25 30

Thr Ala Thr Tyr Tyr Cys
35

<210> SEQ ID NO 40
<211> LENGTH: 42
<212> TYPE: PRT
<213> ORGANISM: Mus <mouse, genus>
<220> FEATURE:
<223> OTHER INFORMATION: HC-FR4 "18B4D5

<400> SEQUENCE: 40

Trp Gly Gln Gly Thr Thr Leu Thr Val Ser Ser Ala Lys Thr Thr Ala
1 5 10 15

```
Pro Ser Val Tyr Pro Leu Ala Pro Val Cys Gly Asp Thr Thr Gly Ser
            20                  25                  30

Ser Val Thr Leu Gly Cys Leu Val Lys Ser
        35                  40


<210> SEQ ID NO 41
<211> LENGTH: 25
<212> TYPE: PRT
<213> ORGANISM: Mus <mouse, genus>
<220> FEATURE:
<223> OTHER INFORMATION: HC-FR1 "17F7B2

<400> SEQUENCE: 41

Glu Val Gln Leu Gln Gln Ser Gly Thr Val Leu Ala Arg Pro Gly Ala
1               5                   10                  15

Ser Val Lys Met Ser Cys Lys Ala Ser
            20                  25


<210> SEQ ID NO 42
<211> LENGTH: 17
<212> TYPE: PRT
<213> ORGANISM: Mus <mouse, genus>
<220> FEATURE:
<223> OTHER INFORMATION: HC-FR2 "17F7B2

<400> SEQUENCE: 42

Met His Trp Val Lys Gln Arg Pro Gly Gln Gly Leu Glu Trp Ile Gly
1               5                   10                  15

Ala


<210> SEQ ID NO 43
<211> LENGTH: 38
<212> TYPE: PRT
<213> ORGANISM: Mus <mouse, genus>
<220> FEATURE:
<223> OTHER INFORMATION: HC-FR3 "17F7B2

<400> SEQUENCE: 43

Thr Tyr Asn Gln Lys Phe Lys Gly Lys Ala Lys Leu Thr Ala Val Thr
1               5                   10                  15

Ser Ala Ser Thr Ala Tyr Met Glu Leu Ser Ser Leu Thr Asn Glu Asp
            20                  25                  30

Ser Ala Val Tyr Tyr Cys
        35


<210> SEQ ID NO 44
<211> LENGTH: 21
<212> TYPE: PRT
<213> ORGANISM: Mus <mouse, genus>
<220> FEATURE:
<223> OTHER INFORMATION: HC-FR4 "17F7B2

<400> SEQUENCE: 44

Trp Gly Gln Gly Thr Leu Val Thr Val Ser Ala Ala Lys Thr Thr Pro
1               5                   10                  15

Pro Ser Val Tyr Ser
            20


<210> SEQ ID NO 45
<211> LENGTH: 25
<212> TYPE: PRT
<213> ORGANISM: Mus <mouse, genus>
<220> FEATURE:
```

<223> OTHER INFORMATION: HC-FR1 "11B6E6

<400> SEQUENCE: 45

Gln Val Lys Leu Glu Glu Ser Gly Pro Gly Leu Val Ala Pro Ser Gln
1 5 10 15

Ser Leu Ser Ile Thr Cys Thr Val Ser
20 25

<210> SEQ ID NO 46
<211> LENGTH: 17
<212> TYPE: PRT
<213> ORGANISM: Mus <mouse, genus>
<220> FEATURE:
<223> OTHER INFORMATION: HC-FR2 "11B6E6

<400> SEQUENCE: 46

Ile Ser Trp Ile Arg Gln Pro Pro Gly Lys Gly Leu Glu Trp Leu Gly
1 5 10 15

Val

<210> SEQ ID NO 47
<211> LENGTH: 38
<212> TYPE: PRT
<213> ORGANISM: Mus <mouse, genus>
<220> FEATURE:
<223> OTHER INFORMATION: HC-FR3 "11B6E6

<400> SEQUENCE: 47

Asn Tyr Asn Ser Ala Phe Met Ser Arg Leu Ser Ile Ser Lys Asp Asn
1 5 10 15

Ser Lys Ser Gln Val Phe Leu Lys Met Phe Ser Leu Gln Thr Asp Asp
20 25 30

Thr Ala Ile Tyr Tyr Cys
35

<210> SEQ ID NO 48
<211> LENGTH: 42
<212> TYPE: PRT
<213> ORGANISM: Mus <mouse, genus>
<220> FEATURE:
<223> OTHER INFORMATION: HC-FR4 "11B6E6

<400> SEQUENCE: 48

Trp Gly Gln Gly Thr Ser Val Thr Val Ser Ser Ala Lys Thr Thr Ala
1 5 10 15

Pro Ser Val Tyr Pro Leu Ala Pro Val Cys Gly Asp Thr Thr Gly Ser
20 25 30

Ser Val Thr Leu Gly Cys Leu Val Lys Ser
35 40

<210> SEQ ID NO 49
<211> LENGTH: 25
<212> TYPE: PRT
<213> ORGANISM: Mus <mouse, genus>
<220> FEATURE:
<223> OTHER INFORMATION: HC-FR1 "14G12D7

<400> SEQUENCE: 49

Glu Val Gln Leu Gln Glu Ser Gly Pro Gly Leu Val Lys Pro Ser Gln
1 5 10 15

Ser Leu Ser Leu Thr Cys Thr Val Thr
20 25

<210> SEQ ID NO 50
<211> LENGTH: 17
<212> TYPE: PRT
<213> ORGANISM: Mus <mouse, genus>
<220> FEATURE:
<223> OTHER INFORMATION: HC-FR2 "14G12D7

<400> SEQUENCE: 50

Trp Asn Trp Ile Arg Gln Phe Pro Gly Asn Lys Leu Glu Trp Met Gly
1 5 10 15

Tyr

<210> SEQ ID NO 51
<211> LENGTH: 38
<212> TYPE: PRT
<213> ORGANISM: Mus <mouse, genus>
<220> FEATURE:
<223> OTHER INFORMATION: HC-FR3 "14G12D7

<400> SEQUENCE: 51

Ser Tyr Asn Pro Ser Leu Lys Ser Arg Ile Ser Ile Thr Arg Asp Thr
1 5 10 15

Ser Lys Asn Gln Phe Phe Leu Gln Leu Asn Ser Val Thr Thr Glu Asp
20 25 30

Thr Ala Thr Tyr Tyr Cys
35

<210> SEQ ID NO 52
<211> LENGTH: 21
<212> TYPE: PRT
<213> ORGANISM: Mus <mouse, genus>
<220> FEATURE:
<223> OTHER INFORMATION: HC-FR4 "14G12D7

<400> SEQUENCE: 52

Trp Gly Gln Gly Thr Thr Leu Thr Val Ser Ser Ala Lys Thr Thr Pro
1 5 10 15

Pro Ser Val Tyr Ser
20

<210> SEQ ID NO 53
<211> LENGTH: 25
<212> TYPE: PRT
<213> ORGANISM: Mus <mouse, genus>
<220> FEATURE:
<223> OTHER INFORMATION: HC-FR1 "11A12C6

<400> SEQUENCE: 53

Gln Val Gln Leu Lys Glu Ser Gly Pro Gly Leu Val Ala Pro Ser Gln
1 5 10 15

Ser Leu Ser Ile Thr Cys Thr Val Ser
20 25

<210> SEQ ID NO 54
<211> LENGTH: 17
<212> TYPE: PRT
<213> ORGANISM: Mus <mouse, genus>
<220> FEATURE:
<223> OTHER INFORMATION: HC-FR2 "11A12C6

<400> SEQUENCE: 54

Ile Asn Trp Ile Arg Gln Thr Pro Gly Lys Gly Leu Glu Trp Leu Gly
1 5 10 15

```
Val


<210> SEQ ID NO 55
<211> LENGTH: 38
<212> TYPE: PRT
<213> ORGANISM: Mus <mouse, genus>
<220> FEATURE:
<223> OTHER INFORMATION: HC-FR3 "11A12C6

<400> SEQUENCE: 55

Asn Tyr Asn Ser Ala Phe Met Ser Arg Leu Ser Ile Ser Arg Asp Asn
1               5                   10                  15

Ser Lys Ser Gln Val Phe Leu Lys Met Asn Ser Leu Gln Thr Asp Asp
            20                  25                  30

Thr Ala Ile Tyr Tyr Cys
        35


<210> SEQ ID NO 56
<211> LENGTH: 21
<212> TYPE: PRT
<213> ORGANISM: Mus <mouse, genus>
<220> FEATURE:
<223> OTHER INFORMATION: HC-FR4 "11A12C6

<400> SEQUENCE: 56

Trp Gly Ala Gly Thr Thr Val Thr Val Ser Ser Ala Lys Thr Thr Pro
1               5                   10                  15

Pro Ser Val Tyr Ser
            20


<210> SEQ ID NO 57
<211> LENGTH: 25
<212> TYPE: PRT
<213> ORGANISM: Mus <mouse, genus>
<220> FEATURE:
<223> OTHER INFORMATION: HC-FR1 "15E11B7

<400> SEQUENCE: 57

Glu Val Gln Leu Glu Gln Ser Gly Pro Glu Leu Val Lys Pro Gly Asp
1               5                   10                  15

Ser Val Lys Ile Ser Cys Lys Ala Ser
            20                  25


<210> SEQ ID NO 58
<211> LENGTH: 17
<212> TYPE: PRT
<213> ORGANISM: Mus <mouse, genus>
<220> FEATURE:
<223> OTHER INFORMATION: HC-FR2 "15E11B7

<400> SEQUENCE: 58

Met Asn Trp Val Lys Gln Ser His Gly Lys Ser Leu Glu Trp Ile Gly
1               5                   10                  15

Arg


<210> SEQ ID NO 59
<211> LENGTH: 38
<212> TYPE: PRT
<213> ORGANISM: Mus <mouse, genus>
<220> FEATURE:
<223> OTHER INFORMATION: HC-FR3 "15E11B7

<400> SEQUENCE: 59

Phe Asn Asn Gln Lys Phe Lys Asp Lys Ala Thr Leu Thr Val Asp Lys
```

```
1               5                   10                  15

Ser Ser Ser Thr Ala His Met Glu Leu Leu Ser Leu Thr Ser Glu Asp
            20                  25                  30

Ser Ala Val Tyr Tyr Cys
        35


<210> SEQ ID NO 60
<211> LENGTH: 42
<212> TYPE: PRT
<213> ORGANISM: Mus <mouse, genus>
<220> FEATURE:
<223> OTHER INFORMATION: HC-FR4 "15E11B7

<400> SEQUENCE: 60

Trp Gly Gln Gly Thr Leu Val Thr Val Ser Glu Ala Lys Thr Thr Ala
1               5                   10                  15

Pro Ser Val Tyr Pro Leu Ala Pro Val Cys Gly Asp Thr Thr Gly Ser
            20                  25                  30

Ser Val Thr Leu Gly Cys Leu Val Lys Ser
        35                  40


<210> SEQ ID NO 61
<211> LENGTH: 26
<212> TYPE: PRT
<213> ORGANISM: Mus <mouse, genus>
<220> FEATURE:
<223> OTHER INFORMATION: LC-FR1 "18B4D5

<400> SEQUENCE: 61

Asp Ile Val Met Thr Gln Ser Pro Ala Ile Met Ser Ala Ser Leu Gly
1               5                   10                  15

Glu Arg Val Thr Met Thr Cys Thr Ala Ser
            20                  25


<210> SEQ ID NO 62
<211> LENGTH: 17
<212> TYPE: PRT
<213> ORGANISM: Mus <mouse, genus>
<220> FEATURE:
<223> OTHER INFORMATION: LC-FR2 "18B4D5

<400> SEQUENCE: 62

Leu Tyr Trp Tyr Gln Gln Lys Pro Gly Ser Ser Pro Lys Leu Trp Ile
1               5                   10                  15

Tyr


<210> SEQ ID NO 63
<211> LENGTH: 36
<212> TYPE: PRT
<213> ORGANISM: Mus <mouse, genus>
<220> FEATURE:
<223> OTHER INFORMATION: LC-FR3 "18B4D5

<400> SEQUENCE: 63

Asn Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Thr Tyr Tyr Cys
        35


<210> SEQ ID NO 64
```

<211> LENGTH: 20
<212> TYPE: PRT
<213> ORGANISM: Mus <mouse, genus>
<220> FEATURE:
<223> OTHER INFORMATION: LC-FR4 "18B4D5

<400> SEQUENCE: 64

Phe Gly Gly Gly Thr Lys Leu Glu Ile Lys Arg Ala Asp Ala Ala Pro
1 5 10 15

Thr Val Ser Thr
20

<210> SEQ ID NO 65
<211> LENGTH: 26
<212> TYPE: PRT
<213> ORGANISM: Mus <mouse, genus>
<220> FEATURE:
<223> OTHER INFORMATION: LC-FR1 "17F7B2

<400> SEQUENCE: 65

Asp Val Val Met Thr Gln Thr Pro Leu Ser Leu Pro Val Ser Leu Gly
1 5 10 15

Asp Gln Ala Ser Ile Ser Cys Arg Ser Ser
20 25

<210> SEQ ID NO 66
<211> LENGTH: 17
<212> TYPE: PRT
<213> ORGANISM: Mus <mouse, genus>
<220> FEATURE:
<223> OTHER INFORMATION: LC-FR2 "17F7B2

<400> SEQUENCE: 66

Leu His Trp Tyr Leu Gln Lys Pro Gly Gln Ser Pro Lys Leu Leu Ile
1 5 10 15

Tyr

<210> SEQ ID NO 67
<211> LENGTH: 36
<212> TYPE: PRT
<213> ORGANISM: Mus <mouse, genus>
<220> FEATURE:
<223> OTHER INFORMATION: LC-FR3 "17F7B2

<400> SEQUENCE: 67

Asn Arg Phe Ser Gly Val Pro Asp Arg Phe Ser Gly Ser Gly Ser Gly
1 5 10 15

Thr Asp Phe Thr Leu Lys Ile Ser Arg Val Glu Ala Glu Asp Leu Gly
20 25 30

Val Tyr Phe Cys
35

<210> SEQ ID NO 68
<211> LENGTH: 20
<212> TYPE: PRT
<213> ORGANISM: Mus <mouse, genus>
<220> FEATURE:
<223> OTHER INFORMATION: LC-FR4 "17F7B2

<400> SEQUENCE: 68

Phe Gly Ser Gly Thr Lys Leu Glu Ile Lys Arg Ala Asp Ala Ala Pro
1 5 10 15

Thr Val Ser Thr
20

<210> SEQ ID NO 69
<211> LENGTH: 26
<212> TYPE: PRT
<213> ORGANISM: Mus <mouse, genus>
<220> FEATURE:
<223> OTHER INFORMATION: LC-FR1 "11B6E6

<400> SEQUENCE: 69

Asp Ile Val Leu Thr Gln Ser Pro Ser Ser Leu Ala Val Ser Ala Gly
1               5                   10                  15

Glu Lys Val Thr Met Arg Cys Lys Ser Ser
            20                  25

<210> SEQ ID NO 70
<211> LENGTH: 17
<212> TYPE: PRT
<213> ORGANISM: Mus <mouse, genus>
<220> FEATURE:
<223> OTHER INFORMATION: LC-FR2 "11B6E6

<400> SEQUENCE: 70

Leu Ala Trp Tyr Gln Gln Lys Pro Gly Gln Ser Pro Lys Leu Leu Ile
1               5                   10                  15

Tyr

<210> SEQ ID NO 71
<211> LENGTH: 36
<212> TYPE: PRT
<213> ORGANISM: Mus <mouse, genus>
<220> FEATURE:
<223> OTHER INFORMATION: LC-FR3 "11B6E6

<400> SEQUENCE: 71

Thr Arg Glu Ser Gly Val Pro Asp Arg Phe Thr Gly Ser Gly Ser Gly
1               5                   10                  15

Thr Asp Phe Thr Leu Thr Ile Ser Ser Val Gln Ala Glu Asp Leu Ala
            20                  25                  30

Val Tyr Tyr Cys
        35

<210> SEQ ID NO 72
<211> LENGTH: 20
<212> TYPE: PRT
<213> ORGANISM: Mus <mouse, genus>
<220> FEATURE:
<223> OTHER INFORMATION: LC-FR4 "11B6E6

<400> SEQUENCE: 72

Phe Gly Ser Gly Thr Lys Leu Glu Ile Lys Arg Ala Asp Ala Ala Pro
1               5                   10                  15

Thr Val Ser Thr
            20

<210> SEQ ID NO 73
<211> LENGTH: 26
<212> TYPE: PRT
<213> ORGANISM: Mus <mouse, genus>
<220> FEATURE:
<223> OTHER INFORMATION: LC-FR1 "14G12D7

<400> SEQUENCE: 73

Glu Ile Val Ile Thr Gln Ser Pro Ala Ile Met Ser Ala Ser Pro Gly
1               5                   10                  15

Glu Lys Val Thr Met Thr Cys Arg Ala Ser
20 25

<210> SEQ ID NO 74
<211> LENGTH: 17
<212> TYPE: PRT
<213> ORGANISM: Mus <mouse, genus>
<220> FEATURE:
<223> OTHER INFORMATION: LC-FR2 "14G12D7

<400> SEQUENCE: 74

Leu His Trp Tyr Gln Gln Lys Ser Gly Ala Ser Pro Lys Leu Trp Ile
1 5 10 15

Tyr

<210> SEQ ID NO 75
<211> LENGTH: 36
<212> TYPE: PRT
<213> ORGANISM: Mus <mouse, genus>
<220> FEATURE:
<223> OTHER INFORMATION: LC-FR3 "14G12D7

<400> SEQUENCE: 75

Asn Leu Ala Ser Gly Val Pro Ala Arg Phe Ser Gly Ser Gly Ser Gly
1 5 10 15

Thr Ser Tyr Ser Leu Thr Ile Ser Ser Val Glu Ala Glu Asp Ala Ala
20 25 30

Thr Tyr Tyr Cys
35

<210> SEQ ID NO 76
<211> LENGTH: 20
<212> TYPE: PRT
<213> ORGANISM: Mus <mouse, genus>
<220> FEATURE:
<223> OTHER INFORMATION: LC-FR4 "14G12D7

<400> SEQUENCE: 76

Phe Gly Gly Gly Thr Lys Leu Glu Ile Lys Arg Ala Asp Ala Ala Pro
1 5 10 15

Thr Val Ser Thr
20

<210> SEQ ID NO 77
<211> LENGTH: 26
<212> TYPE: PRT
<213> ORGANISM: Mus <mouse, genus>
<220> FEATURE:
<223> OTHER INFORMATION: LC-FR1 "11A12C6

<400> SEQUENCE: 77

Asp Ile Val Met Thr Gln Ser Pro Ser Ser Leu Ala Val Ser Ala Gly
1 5 10 15

Glu Lys Val Thr Met Ser Cys Lys Ser Ser
20 25

<210> SEQ ID NO 78
<211> LENGTH: 17
<212> TYPE: PRT
<213> ORGANISM: Mus <mouse, genus>
<220> FEATURE:
<223> OTHER INFORMATION: LC-FR2 "11A12C6

<400> SEQUENCE: 78

Leu Ala Trp Tyr Gln Gln Arg Pro Gly Gln Ser Pro Lys Leu Leu Ile
1 5 10 15

Tyr

<210> SEQ ID NO 79
<211> LENGTH: 36
<212> TYPE: PRT
<213> ORGANISM: Mus <mouse, genus>
<220> FEATURE:
<223> OTHER INFORMATION: LC-FR3 "11A12C6

<400> SEQUENCE: 79

Thr Arg Glu Ser Gly Val Pro Asp Arg Phe Thr Gly Ser Gly Ser Gly
1 5 10 15

Thr Asp Phe Thr Leu Thr Ile Gly Ser Val Gln Ala Glu Asp Leu Ala
20 25 30

Val Tyr Tyr Cys
35

<210> SEQ ID NO 80
<211> LENGTH: 20
<212> TYPE: PRT
<213> ORGANISM: Mus <mouse, genus>
<220> FEATURE:
<223> OTHER INFORMATION: LC-FR4 "11A12C6

<400> SEQUENCE: 80

Phe Gly Ser Gly Thr Lys Leu Glu Ile Lys Arg Ala Asp Ala Ala Pro
1 5 10 15

Thr Val Ser Thr
20

<210> SEQ ID NO 81
<211> LENGTH: 26
<212> TYPE: PRT
<213> ORGANISM: Mus <mouse, genus>
<220> FEATURE:
<223> OTHER INFORMATION: LC-FR1 "15E11B7

<400> SEQUENCE: 81

Asp Ile Val Leu Thr Gln Ser Thr Thr Ser Leu Ala Val Ser Leu Gly
1 5 10 15

Gln Arg Ala Thr Ile Ser Cys Arg Ala Ser
20 25

<210> SEQ ID NO 82
<211> LENGTH: 17
<212> TYPE: PRT
<213> ORGANISM: Mus <mouse, genus>
<220> FEATURE:
<223> OTHER INFORMATION: LC-FR2 "15E11B7

<400> SEQUENCE: 82

Met His Trp Tyr Gln Gln Lys Pro Gly Gln Pro Pro Lys Leu Leu Ile
1 5 10 15

Tyr

<210> SEQ ID NO 83
<211> LENGTH: 36
<212> TYPE: PRT
<213> ORGANISM: Mus <mouse, genus>
<220> FEATURE:
<223> OTHER INFORMATION: LC-FR3 "15E11B7

<400> SEQUENCE: 83

Asn Leu Glu Ser Gly Val Pro Ala Arg Phe Ser Gly Ser Gly Ser Gly
1 5 10 15

Thr Asp Phe Thr Leu Asn Ile His Pro Val Glu Glu Glu Asp Ala Ala
20 25 30

Thr Tyr Tyr Cys
35

<210> SEQ ID NO 84
<211> LENGTH: 20
<212> TYPE: PRT
<213> ORGANISM: Mus <mouse, genus>
<220> FEATURE:
<223> OTHER INFORMATION: LC-FR4 "15E11B7

<400> SEQUENCE: 84

Phe Gly Gly Gly Thr Lys Leu Glu Ile Lys Arg Ala Asp Ala Ala Pro
1 5 10 15

Thr Val Ser Thr
20

<210> SEQ ID NO 85
<211> LENGTH: 144
<212> TYPE: PRT
<213> ORGANISM: Mus <mouse, genus>
<220> FEATURE:
<223> OTHER INFORMATION: Consensus HC "18B4D5

<400> SEQUENCE: 85

Glu Val Lys Leu Gln Glu Ser Gly Pro Gly Leu Val Lys Pro Ser Gln
1 5 10 15

Ser Leu Ser Leu Thr Cys Thr Val Thr Gly Tyr Ser Ile Thr Ser Asp
20 25 30

Tyr Thr Trp Asn Trp Ile Arg Gln Phe Pro Gly Asn Lys Leu Glu Trp
35 40 45

Met Gly Tyr Ile Ser Phe Ser Gly Ser Thr Ser Tyr Asn Pro Ser Leu
50 55 60

Lys Ser Arg Leu Ser Ile Thr Arg Asp Thr Ser Lys Asn Gln Phe Phe
65 70 75 80

Leu Gln Leu Asn Ser Val Thr Thr Glu Asp Thr Ala Thr Tyr Tyr Cys
85 90 95

Ala Arg Gly Leu Asp Tyr Trp Gly Gln Gly Thr Thr Leu Thr Val Ser
100 105 110

Ser Ala Lys Thr Thr Ala Pro Ser Val Tyr Pro Leu Ala Pro Val Cys
115 120 125

Gly Asp Thr Thr Gly Ser Ser Val Thr Leu Gly Cys Leu Val Lys Ser
130 135 140

<210> SEQ ID NO 86
<211> LENGTH: 118
<212> TYPE: PRT
<213> ORGANISM: Mus <mouse, genus>
<220> FEATURE:
<223> OTHER INFORMATION: Consensus LC "18B4D5

<400> SEQUENCE: 86

Asp Ile Val Met Thr Gln Ser Pro Ala Ile Met Ser Ala Ser Leu Gly
1 5 10 15

Glu Arg Val Thr Met Thr Cys Thr Ala Ser Ser Ser Ile Ser Ser Ser

```
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Leu His Arg Ser Pro
                85                  90                  95

Trp Thr Phe Gly Gly Gly Thr Lys Leu Glu Ile Lys Arg Ala Asp Ala
            100                 105                 110

Ala Pro Thr Val Ser Thr
        115


<210> SEQ ID NO 87
<211> LENGTH: 128
<212> TYPE: PRT
<213> ORGANISM: Mus <mouse, genus>
<220> FEATURE:
<223> OTHER INFORMATION: Consensus HC "17F7B2

<400> SEQUENCE: 87

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Ala Phe Tyr Pro Gly Lys Ser Asp Thr Thr Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Lys Gly Tyr Arg Tyr Asp Trp Phe Ala Tyr Trp Gly Gln Gly Thr
            100                 105                 110

Leu Val Thr Val Ser Ala Ala Lys Thr Thr Pro Pro Ser Val Tyr Ser
        115                 120                 125


<210> SEQ ID NO 88
<211> LENGTH: 122
<212> TYPE: PRT
<213> ORGANISM: Mus <mouse, genus>
<220> FEATURE:
<223> OTHER INFORMATION: Consensus LC "17F7B2

<400> SEQUENCE: 88

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Ile Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Leu Gly Val Tyr Phe Cys Ser Gln Asn
                85                  90                  95

Thr His Val Pro Phe Thr Phe Gly Ser Gly Thr Lys Leu Glu Ile Lys
            100                 105                 110

Arg Ala Asp Ala Ala Pro Thr Val Ser Thr
        115                 120
```

```
<210> SEQ ID NO 89
<211> LENGTH: 149
<212> TYPE: PRT
<213> ORGANISM: Mus <mouse, genus>
<220> FEATURE:
<223> OTHER INFORMATION: Consensus HC "11B6E6

<400> SEQUENCE: 89

Gln Val Lys Leu Glu Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Ser Ile Ser Lys Asp Asn Ser Lys Ser Gln Val Phe Leu
65                  70                  75                  80

Lys Met Phe Ser Leu Gln Thr Asp Asp Thr Ala Ile Tyr Tyr Cys Val
                85                  90                  95

Arg Ala His Gly Tyr Tyr Phe Ala Met Asp Tyr Trp Gly Gln Gly Thr
            100                 105                 110

Ser Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Ser
145
```

```
<210> SEQ ID NO 90
<211> LENGTH: 122
<212> TYPE: PRT
<213> ORGANISM: Mus <mouse, genus>
<220> FEATURE:
<223> OTHER INFORMATION: Consensus LC "11B6E6

<400> SEQUENCE: 90

Asp Ile Val Leu Thr Gln Ser Pro Ser Ser Leu Ala Val Ser Ala Gly
1               5                   10                  15

Glu Lys Val Thr Met Arg Cys Lys Ser Ser Gln Ser Leu Leu Asn Ser
            20                  25                  30

Ser Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Phe Thr Phe Gly Ser Gly Thr Lys Leu Glu Ile Lys
            100                 105                 110
```

```
Arg Ala Asp Ala Ala Pro Thr Val Ser Thr
        115                 120


<210> SEQ ID NO 91
<211> LENGTH: 123
<212> TYPE: PRT
<213> ORGANISM: Mus <mouse, genus>
<220> FEATURE:
<223> OTHER INFORMATION: Consensus HC "14G12D7

<400> SEQUENCE: 91

Glu Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Val Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ile Tyr Ser Gly Thr Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Thr Arg Gly Val Asp Tyr Trp Gly Gln Gly Thr Thr Leu Thr Val Ser
            100                 105                 110

Ser Ala Lys Thr Thr Pro Pro Ser Val Tyr Ser
        115                 120


<210> SEQ ID NO 92
<211> LENGTH: 118
<212> TYPE: PRT
<213> ORGANISM: Mus <mouse, genus>
<220> FEATURE:
<223> OTHER INFORMATION: Consensus LC "14G12D7

<400> SEQUENCE: 92

Asp Ile Val Leu Thr Gln Ser Pro Ala Ile Met Ser Ala Ser Pro Gly
1               5                   10                  15

Glu Lys Val Thr Met Thr Cys Arg Ala Ser Ser Ser Val Arg Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Leu Gln Phe Ser Gly Tyr Pro
                85                  90                  95

Phe Thr Phe Gly Gly Gly Thr Lys Leu Glu Ile Lys Arg Ala Asp Ala
            100                 105                 110

Ala Pro Thr Val Ser Thr
        115


<210> SEQ ID NO 93
<211> LENGTH: 128
<212> TYPE: PRT
<213> ORGANISM: Mus <mouse, genus>
<220> FEATURE:
<223> OTHER INFORMATION: Consensus HC "11A12C6
```

<400> SEQUENCE: 93

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Asp Ile Asn Trp Ile Arg Gln Thr Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Ser Ile Ser Arg Asp Asn Ser Lys Ser Gln Val Phe Leu
65                  70                  75                  80

Lys Met Asn Ser Leu Gln Thr Asp Asp Thr Ala Ile Tyr Tyr Cys Val
                85                  90                  95

Arg Gly Asp Gly Tyr Tyr Trp Tyr Phe Asp Val Trp Gly Ala Gly Thr
            100                 105                 110

Thr Val Thr Val Ser Ser Ala Lys Thr Thr Pro Pro Ser Val Tyr Ser
        115                 120                 125

<210> SEQ ID NO 94
<211> LENGTH: 121
<212> TYPE: PRT
<213> ORGANISM: Mus <mouse, genus>
<220> FEATURE:
<223> OTHER INFORMATION: Consensus LC "11A12C6

<400> SEQUENCE: 94

Ile Val Met Thr Gln Ser Pro Ser Ser Leu Ala Val Ser Ala Gly Glu
1               5                   10                  15

Lys Val Thr Met Ser Cys Lys Ser Ser Gln Ser Leu Phe Ser Ser Ser
            20                  25                  30

Ala Arg Lys Asn Tyr Leu Ala Trp Tyr Gln Gln Arg Pro Gly Gln Ser
        35                  40                  45

Pro Lys Leu Leu Ile Tyr Trp Ala Ser Thr Arg Glu Ser Gly Val Pro
    50                  55                  60

Asp Arg Phe Thr Gly Ser Gly Ser Gly Thr Asp Phe Thr Leu Thr Ile
65                  70                  75                  80

Gly Ser Val Gln Ala Glu Asp Leu Ala Val Tyr Tyr Cys Lys Gln Ser
                85                  90                  95

Tyr Ser Leu Phe Thr Phe Gly Ser Gly Thr Lys Leu Glu Ile Lys Arg
            100                 105                 110

Ala Asp Ala Ala Pro Thr Val Ser Thr
        115                 120

<210> SEQ ID NO 95
<211> LENGTH: 149
<212> TYPE: PRT
<213> ORGANISM: Mus <mouse, genus>
<220> FEATURE:
<223> OTHER INFORMATION: Consensus HC "15E11B7

<400> SEQUENCE: 95

Glu Val Gln Leu Glu Gln Ser Gly Pro Glu Leu Val Lys Pro Gly Asp
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Asp Tyr Thr Phe Asn Asn Gln Lys Phe
    50                  55                  60

Lys Asp Lys Ala Thr Leu Thr Val Asp Lys Ser Ser Ser Thr Ala His
65                  70                  75                  80

Met Glu Leu Leu Ser Leu Thr Ser Glu Asp Ser Ala Val Tyr Tyr Cys
                85                  90                  95

Gly Gly Gly Val Arg Gly Ala Trp Phe Ala Phe Trp Gly Gln Gly Thr
            100                 105                 110

Leu Val Thr Val Ser Glu Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Ser
145

<210> SEQ ID NO 96
<211> LENGTH: 121
<212> TYPE: PRT
<213> ORGANISM: Mus <mouse, genus>
<220> FEATURE:
<223> OTHER INFORMATION: Consensus LC "15E11B7

<400> SEQUENCE: 96

Asp Ile Val Leu Thr Gln Ser Thr Thr Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Ala
                85                  90                  95

Asp Leu Pro Tyr Thr Phe Gly Gly Gly Thr Lys Leu Glu Ile Lys Arg
            100                 105                 110

Ala Asp Ala Ala Pro Thr Val Ser Thr
        115                 120

<210> SEQ ID NO 97
<211> LENGTH: 1533
<212> TYPE: DNA
<213> ORGANISM: Homo sapiens
<220> FEATURE:
<223> OTHER INFORMATION: CAR-18B4D5 Nucleic Acid Sequence

<400> SEQUENCE: 97
atgaaactgc ccgtgagact gctggtgctg atgttttgga ttcccgcttc ctcgagcgac 60
ccatacgatg ttccagatta cgccatcctg tctgatgtgc agcttcagga gtcgggacct 120
ggcctggtga aaccttctca gtctctgtcc ctcacctgca ctgtcactgg ctactcaatc 180
accagtgatt atacctggaa ctggattcgg cagtttccag gaaacaaact ggagtggatg 240
ggctacataa gcttcagtgg tagcactagc tacaacccat ctctcaaaag tcgactctct 300
atcacccgag acacatccaa gaaccagttc ttcctgcagt tgaattctgt gactactgag 360
gacacagcca catattactg tgcaagaggg ctcgactact ggggccaagg caccactctc 420

```
acagtctcct caggaggcgg ttcaggcgga ggtggctctg gcggtggcgg atcgataatg    480

tccagaggac aaattgttct cacccagtct ccagcaatca tgtctgcatc tcttggggaa    540

cgggtcacca tgacctgcac tgccagctca agtataagtt ccagttactt gtactggtac    600

cagcagaagc caggctcctc ccccaaactc tggatttata gcacatccaa cctggcttct    660

ggagtcccag ctcgcttcag tggcagtggg tctgggacct cttactctct cacaatcagc    720

agcatggagg ctgaagatgc tgccacttat tactgccacc agttgcatcg ttccccgtgg    780

acgttcggtg gaggcaccaa gctggaaatc aaagagccca aatcttgtga caaaactcac    840

acatgcccac cgtgccctga tcccaaattt tgggtgctgg tggtggttgg tggagtcctg    900

gcttgctata gcttgctagt aacagtggcc tttattattt tctgggtgag gagtaagagg    960

agcaggctcc tgcacagtga ctacatgaac atgactcccc gccgccccgg gcccacccgc   1020

aagcattacc agccctatgc cccaccacgc gacttcgcag cctatcgctc caaacggggc   1080

agaaagaaac tcctgtatat attcaaacaa ccatttatga gaccagtaca aactactcaa   1140

gaggaagatg gctgtagctg ccgatttcca gaagaagaag aaggaggatg tgaactgaga   1200

gtgaagttca gcaggagcgc agacgccccc gcgtaccagc agggccagaa ccagctctat   1260

aacgagctca atctaggacg aagagaggag tacgatgttt tggacaagag gcgtggccgg   1320

gaccctgaga tgggggggaaa gccgagaagg aagaaccctc aggaaggcct gtacaatgaa  1380

ctgcagaaag ataagatggc ggaggcctac agtgagattg ggatgaaagg cgagcgccgg   1440

aggggcaagg ggcacgatgg cctttaccag ggtctcagta cagccaccaa ggacacctac   1500

gacgcccttc acatgcaggc cctgcccccct cgc                               1533
```

<210> SEQ ID NO 98
<211> LENGTH: 75
<212> TYPE: DNA
<213> ORGANISM: Mus <mouse, genus>
<220> FEATURE:
<223> OTHER INFORMATION: HC-FR1 “18B4D5” DNA

<400> SEQUENCE: 98

```
gaggtcaagc tgcaggagtc aggacctggc ctggtgaaac cttctcagtc tctgtccctc     60

acctgcactg tcact                                                      75
```

<210> SEQ ID NO 99
<211> LENGTH: 75
<212> TYPE: DNA
<213> ORGANISM: Mus <mouse, genus>
<220> FEATURE:
<223> OTHER INFORMATION: HC-FR1 “17F7B2” DNA

<400> SEQUENCE: 99

```
gaggttcagc tccagcagtc tgggactgtg ctggcaaggc ctggggcttc cgtgaagatg     60

tcctgcaagg cttct                                                      75
```

<210> SEQ ID NO 100
<211> LENGTH: 75
<212> TYPE: DNA
<213> ORGANISM: Mus <mouse, genus>
<220> FEATURE:
<223> OTHER INFORMATION: HC-FR1 “11B6E6” DNA

<400> SEQUENCE: 100

```
caggtcaagc tggaggagtc aggacctggc ctggtggcgc cctcacagag cctgtccatt     60
```

acctgcactg tctct 75

<210> SEQ ID NO 101
<211> LENGTH: 75
<212> TYPE: DNA
<213> ORGANISM: Mus <mouse, genus>
<220> FEATURE:
<223> OTHER INFORMATION: HC-FR1 "14G12D7" DNA

<400> SEQUENCE: 101
gaggttcagc tgcaggagtc tggacctggc ctggtgaaac cttctcagtc tctgtccctc 60
acctgcactg tcact 75

<210> SEQ ID NO 102
<211> LENGTH: 75
<212> TYPE: DNA
<213> ORGANISM: Mus <mouse, genus>
<220> FEATURE:
<223> OTHER INFORMATION: HC-FR1 "11A12C6" DNA

<400> SEQUENCE: 102
caggtgcagc tgaaggagtc aggacctggc ctggtggcgc cctcacagag cctgtccatt 60
acctgcactg tctct 75

<210> SEQ ID NO 103
<211> LENGTH: 75
<212> TYPE: DNA
<213> ORGANISM: Mus <mouse, genus>
<220> FEATURE:
<223> OTHER INFORMATION: HC-FR1 "15E11B7" DNA

<400> SEQUENCE: 103
gaggttcagc tggagcagtc tggacctgag ctggtgaagc ctggggattc agtgaagata 60
tcctgcaagg cttct 75

<210> SEQ ID NO 104
<211> LENGTH: 51
<212> TYPE: DNA
<213> ORGANISM: Mus <mouse, genus>
<220> FEATURE:
<223> OTHER INFORMATION: HC-FR2 "18B4D5" DNA

<400> SEQUENCE: 104
tggaactgga tccggcagtt tccaggaaac aaactggagt ggatgggcta c 51

<210> SEQ ID NO 105
<211> LENGTH: 51
<212> TYPE: DNA
<213> ORGANISM: Mus <mouse, genus>
<220> FEATURE:
<223> OTHER INFORMATION: HC-FR2 "17F7B2" DNA

<400> SEQUENCE: 105
atgcactggg taaaacagag gcctgggcag ggtctagaat ggattggtgc t 51

<210> SEQ ID NO 106
<211> LENGTH: 51
<212> TYPE: DNA
<213> ORGANISM: Mus <mouse, genus>
<220> FEATURE:
<223> OTHER INFORMATION: HC-FR2 "11B6E6" DNA

<400> SEQUENCE: 106
ataagctgga ttcgccagcc accaggaaag ggtctggagt ggcttggagt a 51

<210> SEQ ID NO 107
<211> LENGTH: 51
<212> TYPE: DNA
<213> ORGANISM: Mus <mouse, genus>
<220> FEATURE:
<223> OTHER INFORMATION: HC-FR1 “14G12D7” DNA

<400> SEQUENCE: 107
tggaactgga tccggcagtt tcccggaaac aaactggagt ggatgggcta c 51

<210> SEQ ID NO 108
<211> LENGTH: 51
<212> TYPE: DNA
<213> ORGANISM: Mus <mouse, genus>
<220> FEATURE:
<223> OTHER INFORMATION: HC-FR2 “11A12C6” DNA

<400> SEQUENCE: 108
ataaactgga ttcgccagac accaggaaag ggtctggagt ggcttggagt a 51

<210> SEQ ID NO 109
<211> LENGTH: 51
<212> TYPE: DNA
<213> ORGANISM: Mus <mouse, genus>
<220> FEATURE:
<223> OTHER INFORMATION: HC-FR2 “15E11B7” DNA

<400> SEQUENCE: 109
atgaactggg tgaaacagag ccatggaaag agccttgagt ggattggacg t 51

<210> SEQ ID NO 110
<211> LENGTH: 114
<212> TYPE: DNA
<213> ORGANISM: Mus <mouse, genus>
<220> FEATURE:
<223> OTHER INFORMATION: HC-FR3 “18B4D5” DNA

<400> SEQUENCE: 110
agctacaacc catctctcaa aagtcgactc tctatcactc gagacacatc caagaaccag 60
ttcttcctgc agttgaattc tgtgactact gaggacacag ccacatatta ctgt 114

<210> SEQ ID NO 111
<211> LENGTH: 114
<212> TYPE: DNA
<213> ORGANISM: Mus <mouse, genus>
<220> FEATURE:
<223> OTHER INFORMATION: HC-FR3 “17F7B2” DNA

<400> SEQUENCE: 111
acctacaacc agaagttcaa gggcaaggcc aaactgactg ccgtcacatc cgccagtact 60
gcctacatgg agctcagcag cctgacaaat gaggactctg cggtctatta ctgt 114

<210> SEQ ID NO 112
<211> LENGTH: 114
<212> TYPE: DNA
<213> ORGANISM: Mus <mouse, genus>
<220> FEATURE:
<223> OTHER INFORMATION: HC-FR3 “11B6E6” DNA

<400> SEQUENCE: 112
aattataatt cagctttcat gtccagactg agcatcagca aggacaactc caagagccaa 60
gttttcttaa aaatgttcag tctgcaaact gatgacacag ccatatatta ctgt 114

<210> SEQ ID NO 113
<211> LENGTH: 114
<212> TYPE: DNA
<213> ORGANISM: Mus <mouse, genus>
<220> FEATURE:
<223> OTHER INFORMATION: HC-FR3 “14G12D7” DNA

<400> SEQUENCE: 113
agctacaacc catctctcaa aagtcgaatc tctatcactc gagacacatc caagaaccag 60
ttcttcctgc agttgaattc tgtgactact gaggacacag ccacatatta ctgt 114

<210> SEQ ID NO 114
<211> LENGTH: 114
<212> TYPE: DNA
<213> ORGANISM: Mus <mouse, genus>
<220> FEATURE:
<223> OTHER INFORMATION: HC-FR3 “11A12C6” DNA

<400> SEQUENCE: 114
aattataatt cagctttcat gtccagactg agcatcagca gggacaactc caagagccag 60
gttttcttaa aaatgaacag tctgcaaact gatgacacag ccatatatta ctgt 114

<210> SEQ ID NO 115
<211> LENGTH: 114
<212> TYPE: DNA
<213> ORGANISM: Mus <mouse, genus>
<220> FEATURE:
<223> OTHER INFORMATION: HC-FR3 “15E11B7” DNA

<400> SEQUENCE: 115
ttcaacaacc agaagttcaa ggacaaggcc acattgactg tagacaaatc ctcgagcaca 60
gcccacatgg agctcctgag cctgacatct gaggactctg cagtctatta ttgt 114

<210> SEQ ID NO 116
<211> LENGTH: 120
<212> TYPE: DNA
<213> ORGANISM: Mus <mouse, genus>
<220> FEATURE:
<223> OTHER INFORMATION: HC-FR4 “18B4D5” DNA

<400> SEQUENCE: 116
tggggccaag gcaccactct cacagtctcc tcagccaaaa caacagcccc atcggtctat 60
ccactggccc ctgtgtgtgg agatacaact ggctcctcgg tgactctagg atgcctggtc 120

<210> SEQ ID NO 117
<211> LENGTH: 64
<212> TYPE: DNA
<213> ORGANISM: Mus <mouse, genus>
<220> FEATURE:
<223> OTHER INFORMATION: HC-FR4 “17F7B2” DNA

<400> SEQUENCE: 117
tggggccaag ggactctggt cactgtctct gcagccaaaa cgacaccccc atctgtctat 60
tcca 64

<210> SEQ ID NO 118
<211> LENGTH: 126
<212> TYPE: DNA
<213> ORGANISM: Mus <mouse, genus>
<220> FEATURE:
<223> OTHER INFORMATION: HC-FR4 “11B6E6” DNA

<400> SEQUENCE: 118
tggggtcaag gaacctcagt caccgtctcc tcagccaaaa caacagcccc atcggtctat 60
ccactggccc ctgtgtgtgg agatacaact ggctcctcgg tgactctagg atgcctggtc 120
aagtcc 126

<210> SEQ ID NO 119
<211> LENGTH: 64
<212> TYPE: DNA
<213> ORGANISM: Mus <mouse, genus>
<220> FEATURE:
<223> OTHER INFORMATION: HC-FR4 “14G12D7” DNA

<400> SEQUENCE: 119
tggggccaag gcaccactct cacagtctcc tcagccaaaa cgacaccccc atctgtctat 60
tcca 64

<210> SEQ ID NO 120
<211> LENGTH: 64
<212> TYPE: DNA
<213> ORGANISM: Mus <mouse, genus>
<220> FEATURE:
<223> OTHER INFORMATION: HC-FR4 “11A12C6” DNA

<400> SEQUENCE: 120
tggggcgcag ggaccacggt caccgtctcc tcagccaaaa cgacaccccc atctgtctat 60
tcca 64

<210> SEQ ID NO 121
<211> LENGTH: 127
<212> TYPE: DNA
<213> ORGANISM: Mus <mouse, genus>
<220> FEATURE:
<223> OTHER INFORMATION: HC-FR4 “15E11B7” DNA

<400> SEQUENCE: 121
tggggccaag ggactctggt cactgtctct gaagccaaaa caacagcccc atcggtctat 60
ccactggccc ctgtgtgtgg agatacaact ggctcctcgg tgactctagg atgcctggtc 120
aagtcca 127

<210> SEQ ID NO 122
<211> LENGTH: 78
<212> TYPE: DNA
<213> ORGANISM: Mus <mouse, genus>
<220> FEATURE:
<223> OTHER INFORMATION: LC-FR1 “18B4D5” DNA

<400> SEQUENCE: 122
gatattgtga tgacacagtc tccagcaatc atgtctgcat ctcttgggga acgggtcacc 60
atgacctgca ctgccagc 78

<210> SEQ ID NO 123
<211> LENGTH: 78
<212> TYPE: DNA
<213> ORGANISM: Mus <mouse, genus>
<220> FEATURE:
<223> OTHER INFORMATION: LC-FR1 “17F7B2” DNA

<400> SEQUENCE: 123
gatgttgtga tgacccaaac tccactctcc ctgcctgtca gtcttggaga tcaagcctcc 60
atctcttgca gatctagt 78

<210> SEQ ID NO 124
<211> LENGTH: 78
<212> TYPE: DNA
<213> ORGANISM: Mus <mouse, genus>
<220> FEATURE:
<223> OTHER INFORMATION: LC-FR1 “11B6E6” DNA

<400> SEQUENCE: 124
gatattgtgc tgacacagtc tccatcctcc ctggctgtgt cagcaggaga gaaggtcact 60
atgaggtgca aatccagt 78

<210> SEQ ID NO 125
<211> LENGTH: 78
<212> TYPE: DNA
<213> ORGANISM: Mus <mouse, genus>
<220> FEATURE:
<223> OTHER INFORMATION: LC-FR1 “14G12D7” DNA

<400> SEQUENCE: 125
gaaattgtga tcacccagtc tccagcaatc atgtctgcat ctccagggga aaaggtcacc 60
atgacctgca gggccagc 78

<210> SEQ ID NO 126
<211> LENGTH: 78
<212> TYPE: DNA
<213> ORGANISM: Mus <mouse, genus>
<220> FEATURE:
<223> OTHER INFORMATION: LC-FR1 “11A12C6” DNA

<400> SEQUENCE: 126
gatattgtga tgacacagtc tccatcctcc ctggctgtgt cagcaggaga gaaggtcact 60
atgagctgca aatccagt 78

<210> SEQ ID NO 127
<211> LENGTH: 78
<212> TYPE: DNA
<213> ORGANISM: Mus <mouse, genus>
<220> FEATURE:
<223> OTHER INFORMATION: LC-FR1 “15E11B7” DNA

<400> SEQUENCE: 127
gatattgtgc tgacacagtc tacaacttcc ttagctgtgt ctctgggcca gagggccacc 60
atctcatgca gggccagc 78

<210> SEQ ID NO 128
<211> LENGTH: 51
<212> TYPE: DNA
<213> ORGANISM: Mus <mouse, genus>
<220> FEATURE:
<223> OTHER INFORMATION: HC-FR2 “18B4D5” DNA

<400> SEQUENCE: 128
ttgtactggt accagcagaa gccaggatcc tcccccaaac tctggattta t 51

<210> SEQ ID NO 129
<211> LENGTH: 51
<212> TYPE: DNA
<213> ORGANISM: Mus <mouse, genus>
<220> FEATURE:
<223> OTHER INFORMATION: LC-FR2 “17F7B2” DNA

<400> SEQUENCE: 129
ttacattggt acctgcagaa gccaggccag tctccaaagc tcctgatcta c 51

<210> SEQ ID NO 130
<211> LENGTH: 51
<212> TYPE: DNA
<213> ORGANISM: Mus <mouse, genus>
<220> FEATURE:
<223> OTHER INFORMATION: LC-FR2 “11B6E6” DNA

<400> SEQUENCE: 130
ttggcttggt accagcagaa accagggcag tctcctaaac tgctgatcta c 51

<210> SEQ ID NO 131
<211> LENGTH: 51
<212> TYPE: DNA
<213> ORGANISM: Mus <mouse, genus>

<400> SEQUENCE: 131
ttgcactggt accagcagaa gtcaggtgcc tcccccaaac tctggattta t 51

<210> SEQ ID NO 132
<211> LENGTH: 51
<212> TYPE: DNA
<213> ORGANISM: Mus <mouse, genus>
<220> FEATURE:
<223> OTHER INFORMATION: LC-FR2 “11A12C6” DNA

<400> SEQUENCE: 132
ttggcttggt accagcagag accagggcag tctcctaaac tgctgatcta c 51

<210> SEQ ID NO 133
<211> LENGTH: 51
<212> TYPE: DNA
<213> ORGANISM: Mus <mouse, genus>
<220> FEATURE:
<223> OTHER INFORMATION: LC-FR2 “15E11B7” DNA

<400> SEQUENCE: 133
atgcactggt accaacagaa accaggacag ccacccaaac tcctcatcta t 51

<210> SEQ ID NO 134
<211> LENGTH: 108
<212> TYPE: DNA
<213> ORGANISM: Mus <mouse, genus>
<220> FEATURE:
<223> OTHER INFORMATION: LC-FR3 “18B4D5” DNA

<400> SEQUENCE: 134
aacctggctt ctggagtccc agctcgcttc agtggcagtg ggtctgggac ctcttactct 60
ctcacaatca gcagcatgga ggctgaagat gctgccactt attactgc 108

<210> SEQ ID NO 135
<211> LENGTH: 108
<212> TYPE: DNA
<213> ORGANISM: Mus <mouse, genus>
<220> FEATURE:
<223> OTHER INFORMATION: LC-FR3 “17F7B2” DNA

<400> SEQUENCE: 135
aaccgatttt ctggggtccc agacaggttc agtggcagtg gatctgggac agatttcaca 60
ctcaagatca gcagagtgga ggctgaggat ctgggagttt atttctgc 108

<210> SEQ ID NO 136
<211> LENGTH: 108
<212> TYPE: DNA

<213> ORGANISM: Mus <mouse, genus>
<220> FEATURE:
<223> OTHER INFORMATION: LC-FR3 “11B6E6” DNA

<400> SEQUENCE: 136
actagggaat ctggggtccc tgatcgcttc acaggcagtg gatctgggac agatttcact 60
ctcaccatca gcagtgtgca ggctgaagac ctggcagttt attactgc 108

<210> SEQ ID NO 137
<211> LENGTH: 108
<212> TYPE: DNA
<213> ORGANISM: Mus <mouse, genus>
<220> FEATURE:
<223> OTHER INFORMATION: LC-FR3 “14G12D7” DNA

<400> SEQUENCE: 137
aacttggctt ctggagtccc tgctcgcttc agtggcagtg ggtctgggac ctcttactct 60
ctcacaatca gcagtgtgga ggctgaagat gctgccactt attactgc 108

<210> SEQ ID NO 138
<211> LENGTH: 108
<212> TYPE: DNA
<213> ORGANISM: Mus <mouse, genus>
<220> FEATURE:
<223> OTHER INFORMATION: LC-FR3 “11A12C6” DNA

<400> SEQUENCE: 138
accagggaat ctggggtccc tgatcgcttc acaggcagtg gatctgggac agatttcact 60
ctcaccatcg gcagtgtgca ggctgaagac ctggcagttt attactgc 108

<210> SEQ ID NO 139
<211> LENGTH: 108
<212> TYPE: DNA
<213> ORGANISM: Mus <mouse, genus>
<220> FEATURE:
<223> OTHER INFORMATION: LC-FR3 “15E11B7” DNA

<400> SEQUENCE: 139
aacctcgaat ctggggtccc tgccaggttc agtggcagtg ggtctgggac agacttcacc 60
ctcaacatcc atcctgtgga ggaggaggat gctgcaacct attactgt 108

<210> SEQ ID NO 140
<211> LENGTH: 60
<212> TYPE: DNA
<213> ORGANISM: Mus <mouse, genus>
<220> FEATURE:
<223> OTHER INFORMATION: LC-FR4 “18B4D5” DNA

<400> SEQUENCE: 140
ttcggtggag gcaccaagct ggaaatcaaa cgggctgatg ctgcaccaac tgtatccacc 60

<210> SEQ ID NO 141
<211> LENGTH: 60
<212> TYPE: DNA
<213> ORGANISM: Mus <mouse, genus>
<220> FEATURE:
<223> OTHER INFORMATION: LC-FR4 “17F7B2” DNA

<400> SEQUENCE: 141
ttcggctcgg ggacaaagtt ggaaataaaa cgggctgatg ctgcaccaac tgtatccacc 60

<210> SEQ ID NO 142
<211> LENGTH: 61

<212> TYPE: DNA
<213> ORGANISM: Mus <mouse, genus>
<220> FEATURE:
<223> OTHER INFORMATION: LC-FR4 “11B6E6” DNA

<400> SEQUENCE: 142
ttcggctcgg ggacaaagtt ggaaataaaa cgggctgatg ctgcaccaac tgtatccacc 60
a 61

<210> SEQ ID NO 143
<211> LENGTH: 60
<212> TYPE: DNA
<213> ORGANISM: Mus <mouse, genus>
<220> FEATURE:
<223> OTHER INFORMATION: LC-FR4 “14G12D7” DNA

<400> SEQUENCE: 143
ttcggagggg ggaccaagct ggaaataaaa cgggctgatg ctgcaccaac tgtatccacc 60

<210> SEQ ID NO 144
<211> LENGTH: 60
<212> TYPE: DNA
<213> ORGANISM: Mus <mouse, genus>
<220> FEATURE:
<223> OTHER INFORMATION: LC-FR4 “11A12C6” DNA

<400> SEQUENCE: 144
ttcggctcgg ggacaaagtt ggaaataaaa cgggctgatg ctgcaccaac tgtatccacc 60

<210> SEQ ID NO 145
<211> LENGTH: 60
<212> TYPE: DNA
<213> ORGANISM: Mus <mouse, genus>
<220> FEATURE:
<223> OTHER INFORMATION: LC-FR4 “15E11B7” DNA

<400> SEQUENCE: 145
ttcggagggg ggaccaagct ggaaataaaa cgggctgatg ctgcaccaac tgtatccacc 60

<210> SEQ ID NO 146
<211> LENGTH: 18
<212> TYPE: DNA
<213> ORGANISM: Mus <mouse, genus>
<220> FEATURE:
<223> OTHER INFORMATION: HC-CDR3 “18B4D5” DNA

<400> SEQUENCE: 146
gcaagagggc tcgactac 18

<210> SEQ ID NO 147
<211> LENGTH: 33
<212> TYPE: DNA
<213> ORGANISM: Mus <mouse, genus>
<220> FEATURE:
<223> OTHER INFORMATION: HC-CDR3 “17F7B2” DNA

<400> SEQUENCE: 147
acaaagggct ataggtacga ctggtttgct tat 33

<210> SEQ ID NO 148
<211> LENGTH: 36
<212> TYPE: DNA
<213> ORGANISM: Mus <mouse, genus>
<220> FEATURE:
<223> OTHER INFORMATION: HC-CDR3 “11B6E6” DNA

```
<400> SEQUENCE: 148

gtgagagctc acggctatta ctttgctatg gactac                                 36


<210> SEQ ID NO 149
<211> LENGTH: 18
<212> TYPE: DNA
<213> ORGANISM: Mus <mouse, genus>
<220> FEATURE:
<223> OTHER INFORMATION: HC-CDR3 “14G12D7” DNA

<400> SEQUENCE: 149

acaagggggg ttgactac                                                     18


<210> SEQ ID NO 150
<211> LENGTH: 36
<212> TYPE: DNA
<213> ORGANISM: Mus <mouse, genus>
<220> FEATURE:
<223> OTHER INFORMATION: HC-CDR3 “11A12C6” DNA

<400> SEQUENCE: 150

gtaagaggtg atggttacta ctggtacttc gatgtc                                 36


<210> SEQ ID NO 151
<211> LENGTH: 33
<212> TYPE: DNA
<213> ORGANISM: Mus <mouse, genus>
<220> FEATURE:
<223> OTHER INFORMATION: HC-CDR3 “15E11B7” DNA

<400> SEQUENCE: 151

ggaggggggg tacgaggggc ctggtttgct ttc                                    33


<210> SEQ ID NO 152
<211> LENGTH: 21
<212> TYPE: DNA
<213> ORGANISM: Mus <mouse, genus>
<220> FEATURE:
<223> OTHER INFORMATION: HC-CDR2 “18B4D5” DNA

<400> SEQUENCE: 152

ataagcttca gtggtagcac t                                                 21


<210> SEQ ID NO 153
<211> LENGTH: 24
<212> TYPE: DNA
<213> ORGANISM: Mus <mouse, genus>
<220> FEATURE:
<223> OTHER INFORMATION: HC-CDR2 “17F7B2” DNA

<400> SEQUENCE: 153

ttttatcctg gaaaaagtga tact                                              24


<210> SEQ ID NO 154
<211> LENGTH: 21
<212> TYPE: DNA
<213> ORGANISM: Mus <mouse, genus>
<220> FEATURE:
<223> OTHER INFORMATION: HC-CDR2 “11B6E6” DNA

<400> SEQUENCE: 154

atatggactg gtggaggcac a                                                 21


<210> SEQ ID NO 155
<211> LENGTH: 21
```

<212> TYPE: DNA
<213> ORGANISM: Mus <mouse, genus>
<220> FEATURE:
<223> OTHER INFORMATION: HC-CDR2 "14G12D7" DNA

<400> SEQUENCE: 155
ataatctaca gtggtaccac t 21

<210> SEQ ID NO 156
<211> LENGTH: 21
<212> TYPE: DNA
<213> ORGANISM: Mus <mouse, genus>
<220> FEATURE:
<223> OTHER INFORMATION: HC-CDR2 "11A12C6" DNA

<400> SEQUENCE: 156
atatggactg gtggaggcac a 21

<210> SEQ ID NO 157
<211> LENGTH: 24
<212> TYPE: DNA
<213> ORGANISM: Mus <mouse, genus>
<220> FEATURE:
<223> OTHER INFORMATION: HC-CDR2 "15E11B7" DNA

<400> SEQUENCE: 157
attaatcctt acaatgatta tact 24

<210> SEQ ID NO 158
<211> LENGTH: 27
<212> TYPE: DNA
<213> ORGANISM: Mus <mouse, genus>
<220> FEATURE:
<223> OTHER INFORMATION: HC-CDR1 "18B4D5" DNA

<400> SEQUENCE: 158
ggctactcaa tcaccagtga ttatacc 27

<210> SEQ ID NO 159
<211> LENGTH: 24
<212> TYPE: DNA
<213> ORGANISM: Mus <mouse, genus>
<220> FEATURE:
<223> OTHER INFORMATION: HC-CDR1 "17F7B2" DNA

<400> SEQUENCE: 159
ggctacagct ttaccagcta ctgg 24

<210> SEQ ID NO 160
<211> LENGTH: 24
<212> TYPE: DNA
<213> ORGANISM: Mus <mouse, genus>
<220> FEATURE:
<223> OTHER INFORMATION: HC-CDR1 "11B6E6" DNA

<400> SEQUENCE: 160
gggttctcat taaccagcta tgat 24

<210> SEQ ID NO 161
<211> LENGTH: 27
<212> TYPE: DNA
<213> ORGANISM: Mus <mouse, genus>
<220> FEATURE:
<223> OTHER INFORMATION: HC-CDR1 "14G12D7" DNA

<400> SEQUENCE: 161
ggctactcag tcaccagtga ttatgcc 27

<210> SEQ ID NO 162
<211> LENGTH: 24
<212> TYPE: DNA
<213> ORGANISM: Mus <mouse, genus>
<220> FEATURE:
<223> OTHER INFORMATION: HC-CDR1 “11A12C6” DNA

<400> SEQUENCE: 162
gggttctcat taaccagcta tgat 24

<210> SEQ ID NO 163
<211> LENGTH: 24
<212> TYPE: DNA
<213> ORGANISM: Mus <mouse, genus>
<220> FEATURE:
<223> OTHER INFORMATION: HC-CDR1 “15E11B7” DNA

<400> SEQUENCE: 163
ggttactcat ttactggcta cttt 24

<210> SEQ ID NO 164
<211> LENGTH: 27
<212> TYPE: DNA
<213> ORGANISM: Mus <mouse, genus>
<220> FEATURE:
<223> OTHER INFORMATION: LC-CDR3 “18B4D5” DNA

<400> SEQUENCE: 164
caccagttgc atcgttcccc gtggacg 27

<210> SEQ ID NO 165
<211> LENGTH: 27
<212> TYPE: DNA
<213> ORGANISM: Mus <mouse, genus>
<220> FEATURE:
<223> OTHER INFORMATION: LC-CDR3 “17F7B2” DNA

<400> SEQUENCE: 165
tctcaaaata cacatgttcc attcacg 27

<210> SEQ ID NO 166
<211> LENGTH: 24
<212> TYPE: DNA
<213> ORGANISM: Mus <mouse, genus>
<220> FEATURE:
<223> OTHER INFORMATION: LC-CDR3 “11B6E6” DNA

<400> SEQUENCE: 166
aagcaatctt ataatctatt cacg 24

<210> SEQ ID NO 167
<211> LENGTH: 27
<212> TYPE: DNA
<213> ORGANISM: Mus <mouse, genus>
<220> FEATURE:
<223> OTHER INFORMATION: LC-CDR3 “14G12D7” DNA

<400> SEQUENCE: 167
ctgcagttca gtggttaccc gttcacg 27

<210> SEQ ID NO 168
<211> LENGTH: 24
<212> TYPE: DNA
<213> ORGANISM: Mus <mouse, genus>

<220> FEATURE:
<223> OTHER INFORMATION: LC-CDR3 “11A12C6” DNA

<400> SEQUENCE: 168
aagcaatctt atagtctatt cacg 24

<210> SEQ ID NO 169
<211> LENGTH: 27
<212> TYPE: DNA
<213> ORGANISM: Mus <mouse, genus>
<220> FEATURE:
<223> OTHER INFORMATION: LC-CDR3 “15E11B7” DNA

<400> SEQUENCE: 169
cagcacagtg cggatcttcc ttacacg 27

<210> SEQ ID NO 170
<211> LENGTH: 21
<212> TYPE: DNA
<213> ORGANISM: Mus <mouse, genus>
<220> FEATURE:
<223> OTHER INFORMATION: LC-CDR1 “18B4D5” DNA

<400> SEQUENCE: 170
tcaagtataa gttccagtta c 21

<210> SEQ ID NO 171
<211> LENGTH: 33
<212> TYPE: DNA
<213> ORGANISM: Mus <mouse, genus>
<220> FEATURE:
<223> OTHER INFORMATION: LC-CDR1 “17F7B2” DNA

<400> SEQUENCE: 171
cagagccttg tacacagtaa tggaatcacc tat 33

<210> SEQ ID NO 172
<211> LENGTH: 37
<212> TYPE: DNA
<213> ORGANISM: Mus <mouse, genus>
<220> FEATURE:
<223> OTHER INFORMATION: LC-CDR1 “11B6E6” DNA

<400> SEQUENCE: 172
cagagtctgc tcaacagtag cacccgaaag aactact 37

<210> SEQ ID NO 173
<211> LENGTH: 21
<212> TYPE: DNA
<213> ORGANISM: Mus <mouse, genus>
<220> FEATURE:
<223> OTHER INFORMATION: LC-CDR1 “14G12D7” DNA

<400> SEQUENCE: 173
tcaagtgtac gttccagtta c 21

<210> SEQ ID NO 174
<211> LENGTH: 36
<212> TYPE: DNA
<213> ORGANISM: Mus <mouse, genus>
<220> FEATURE:
<223> OTHER INFORMATION: LC-CDR1 “11A12C6” DNA

<400> SEQUENCE: 174
cagagtctgt tcagcagtag tgcccgaaag aactac 36

```
<210> SEQ ID NO 175
<211> LENGTH: 30
<212> TYPE: DNA
<213> ORGANISM: Mus <mouse, genus>
<220> FEATURE:
<223> OTHER INFORMATION: LC-CDR1 "15E11B7" DNA

<400> SEQUENCE: 175

aaaagtgtca gtacatctgg ctataattat                                    30
```